US012630515B2

(12) United States Patent
Schuster et al.

(10) Patent No.: US 12,630,515 B2
(45) Date of Patent: May 19, 2026

(54) SMALL MOLECULE PROSTAGLADIN TRANSPORT INHIBITORS

(71) Applicant: ALBERT EINSTEIN COLLEGE OF MEDICINE, Bronx, NY (US)

(72) Inventors: Victor L. Schuster, New York, NY (US); William Greenlee, Bronx, NY (US); Evripidis Gavathiotis, Roslyn, NY (US)

(73) Assignee: ALBERT EINSTEIN COLLEGE OF MEDICINE, Bronx, NY (US)

( * ) Notice: Subject to any disclaimer, the term of this patent is extended or adjusted under 35 U.S.C. 154(b) by 897 days.

(21) Appl. No.: 17/774,364

(22) PCT Filed: Nov. 2, 2020

(86) PCT No.: PCT/US2020/058533
§ 371 (c)(1),
(2) Date: May 4, 2022

(87) PCT Pub. No.: WO2021/091823
PCT Pub. Date: May 14, 2021

(65) Prior Publication Data

US 2022/0402881 A1 Dec. 22, 2022

Related U.S. Application Data

(60) Provisional application No. 63/069,404, filed on Aug. 24, 2020, provisional application No. 62/931,513, filed on Nov. 6, 2019.

(51) Int. Cl.

| | |
|---|---|
| ***C07D 239/42*** | (2006.01) |
| ***C07D 241/20*** | (2006.01) |
| ***C07D 263/48*** | (2006.01) |
| ***C07D 271/113*** | (2006.01) |
| ***C07D 277/28*** | (2006.01) |
| ***C07D 403/12*** | (2006.01) |
| ***C07D 413/12*** | (2006.01) |
| ***C07D 417/12*** | (2006.01) |

(52) U.S. Cl.
CPC ......... *C07D 239/42* (2013.01); *C07D 241/20* (2013.01); *C07D 263/48* (2013.01); *C07D 271/113* (2013.01); *C07D 277/28* (2013.01); *C07D 403/12* (2013.01); *C07D 413/12* (2013.01); *C07D 417/12* (2013.01)

(58) Field of Classification Search
CPC .. C07D 239/42; C07D 241/20; C07D 263/48; C07D 271/113; C07D 277/28; C07D 403/12; C07D 413/12; C07D 417/12
USPC .......................................................... 514/275
See application file for complete search history.

(56) References Cited

U.S. PATENT DOCUMENTS

| | | | |
|---|---|---|---|
| 9,359,345 | B2 | 6/2016 | Huby et al. |
| 10,351,554 | B2 | 7/2019 | Walensky et al. |
| 2004/0092497 | A1 | 5/2004 | Nagarajan et al. |

FOREIGN PATENT DOCUMENTS

| | | | |
|---|---|---|---|
| WO | 2007136638 | A2 | 11/2007 |
| WO | 2011037610 | A1 | 3/2011 |

OTHER PUBLICATIONS

International Search Report; International Application No. PCT/US2020/058533; International Filing Date—Nov. 2, 2020; Date of Mailing—Feb. 2, 2021; 3 pages.
PUBCHEM CID 1949215, (2005), 1-9.
Written Opinion; International Application No. PCT/US2020/058533; International Filing Date—Nov. 2, 2020; Date of Mailing—Feb. 2, 2021; 6 pages.
Esteve-Turrillar et al., "Monoclonal Antibody-based Immunoassays for Cyprodinil Residue Analysis in QuEChERS-based Fruit Extracts," Food Chemistry, (2015), vol. 187, 530-536.
Fairwell et al., "Quantitative Protein Sequencing Using Mass Spectrometry: Mass Spectral Analysis of 2-Anilino-5-Thiazolinone Derivatives of Amino Acids Without Prior Conversion to the Phenyl Thiohydantoins," Biochemical and Biophysical Research, (1971), vol. 43, (No. 6), 1-11.
International Preliminary Report on Patentability; International Application No. PCT/US2020/058533; International Filing Date—Nov. 2, 2020; Date of Issuance May 10, 2022, 7 pages.

(Continued)

*Primary Examiner* — Kristin A Vajda
(74) *Attorney, Agent, or Firm* — CANTOR COLBURN LLP

(57) ABSTRACT

The disclosure provides compounds of Formula 1, and the pharmaceutically acceptable salts thereof. The variables in Formula 1, e.g. $X^1$-$X^5$, $A^1$, $A^2$, and $R^1$-$R^4$ are described herein. Such compounds are useful as prostaglandin transport (PGT) inhibitors. The disclosure further includes pharmaceutical compositions comprising a compound of Formula 1 or salt thereof and methods of using compounds of Formula 1 and salts thereof to treat diseases and disorders mediated, at least in part, by prostaglandin levels or cyclooxygenase activity. Such diseases and disorders include painful and inflammatory conditions.

Formula (1)

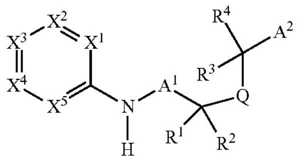

15 Claims, No Drawings

(56) References Cited

OTHER PUBLICATIONS

PubChem CID 1949215, "(4R)-4-ethoxycarbonyl-4-[2-(4-methylanilino -1, 3-thiazol-4-yl] hexanoic acid," (2005), 1-11.
PubChem CID 3100693, "2-Butyl-2-(2-p-tolylamino-thiazol-4-yl)-pentanedioic acid 1-ethyl ester," (2005), 1-14.
PubChem CID 3100701, "4-(Ethxycarbonyl)-4-{2-[(4-methylphenyl)amino]-1, 3-thiazol-4-yl}hexanoic acid," (2005), 1-15.
PubChem CID 3145193, "2-Butyl-2-(2-phenylamino-thiazol-4-yl), pentanedioic acid 1-ethyl ester," (2005), 1-13.
PubChem CID 3699087, "4-Ethoxycarbonyl)-4-{2-[(4-ethoxyphenyl)amino]-1,3-thiazol-4-yl}octanoic acid," (2005), 1-12.
Solankee et al., "Potential Antitubercular Agents, Part I: 4-Thiazolidinone Derivatives," Asian Journal of Chemistry, (1994), vol. 6, (No. 1), 169-171.
Solankee et al., "Thiazolidinones: 2-Phenylimino-5-(a-Carboxy Propyl Pentyl)-4-Thiazolidinones," J. Inst. Chemists (India), (1993), vol. 65, 1-3.
Turrillas et al., "A Class-Selective Immunoassay for Simultaneous Analysis of Anilinopyrimidine Fungicides Using a Rationally Designed Hapten," The Royal Society of Chemistry, (2017), vol. 142, 3975-3985.
Nikolaychuk et al., "Exogenous effect of substituted 1,3,4-thiadiazoles on growth processes of bird's-foot trefoil," Dopovidi Akademii Nauk Ukraini, (1994), (No. 4), Original and English Language Abstract.
Extended European Search Report for Application 20884239.3 [PCT/US2020/058533] dated Jan. 23, 2024; 10 pages.

SMALL MOLECULE PROSTAGLADIN TRANSPORT INHIBITORS

CROSS REFERENCE TO RELATED APPLICATIONS

This application is a National Stage application of PCT/US2020/058533, filed Nov. 2, 2020. This application claims priority to U.S. Provisional Application No. 62/931,513, filed Nov. 6, 2019 and U.S. Provisional Application No. 63/069,404, filed Aug. 24, 2020, the entire contents of which are incorporated herein by reference.

BACKGROUND

Prostaglandins (PGs) play an important role in physiology and clinical settings. Prostaglandins (PGs) are synthesized from arachidonic acid by cyclooxygenases (COX1 and COX2) and corresponding synthases. Their biological effects include triggering inflammation, fever and pain; induction of labor; modulation of renal hemodynamics and of water and solute reabsorption; arterial vasodilatation; stimulation of cell proliferation and angiogenesis; and mediating sensitization of sensory neurons. At the cellular level, PGs are involved in several major signaling pathways, including the mitogen-activated protein (MAP) kinase and protein kinase A pathways by upregulation of cAMP.

The magnitude of PG effects depends not only on their production but also their metabolism. The prostaglandin transporter (PGT) removes PGs from the extracellular compartment and thereby terminates their interactions with receptors on cell membranes. PGT delivers PGs to cytoplasmic 15-OH PG dehydrogenase, resulting in oxidation and inactivation. Because PGT is highly expressed in the tissues and organs where PGs are synthesized, and because PGT regulates a broad and complex PG signaling system, inhibitors of PGT are important for manipulating signaling. Inhibition of PGT lowers blood pressure by vasodilation and natriuresis and inhibits platelet aggregation.

Inhibition of PGT is also useful for dampening dysregulated hyperinflammation that can occur during a SARS-CoV-2 (COVID 19) viral infection. In severe SARS-CoV-2 cases, fatality can be caused by the rapid development of severe lung injury characteristic of acute respiratory distress syndrome (ARDS). Although ARDS is a complication of SARS-CoV-2 infection, it is not viral replication or infection that causes tissue injury; rather, it is the result of dysregulated hyperinflammation in response to viral infection. This pathology is characterized by intense, rapid stimulation of the innate immune response that triggers activation of the Nod-like receptor family, pyrin domain-containing 3 (NLRP3) inflammasome pathway and release of its products including the proinflammatory cytokines IL-6 and IL-1β.

Systemic levels of prostaglandin E2 (PGE2) are elevated by inhibiting PGT. The NLRP3 inflammasome activation is inhibited by PGE 2 in human primary monocyte-derived macrophages. Constitutive interleukin 1-beta (IL-1β) secretion from lipopolysaccharide-primed peripheral blood monocytes is substantially reduced by high doses of PGE2. These data indicate that PGE2 can serve as an autocrine and paracrine regulator to dampen the dysregulated hyperinflammation in response to SARS-CoV-2 viral infection.

Furthermore, it has been shown that endogenous prostacyclin is increased by PGT inhibition. Currently pulmonary arterial hypertension, a rare and deadly disorder, is managed by administering agonists of the prostacyclin signaling pathway. Advanced cases of PAH are managed by continuous intravenous delivery of prostacyclin analogs via an indwelling catheter and external pump. Increasing prostacyclin through PGT inhibition is promising as a less invasive and more effective treatment for PAH.

Known PGT inhibitors include inhibitors of the organic anion transporters (OATs), such as bromcresol green and bromosulfophthalein, and some COX2 inhibitors, such as indomethacin and ibuprofen. These inhibitors are not specific for PGT leading to off-target effects.

Target specific and efficacious PGT inhibitors are desired for treating a number of conditions associated with prostaglandin levels and COX1 and COX2 activity, for increasing systemic levels of prostaglandin E2 (PGE2), increasing endogenous prostacyclin, and for increasing the levels of PGs available for major signaling pathways including the mitogen-activated protein (MAP) kinase and protein kinase A pathways. This disclosure provides PCT inhibitors capable of these functions and having other advantages, as discussed herein.

SUMMARY

In a first embodiment the disclosure includes compounds of Formula 1 and the pharmaceutically acceptable salts thereof.

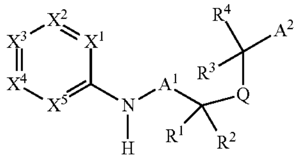

(1)

Within Formula 1 the variables $R^1$-$R^5$, $A^1$, $A^2$, and $X^1$ to $X^5$ carry the following definitions.

$R^1$ and $R^2$ are independently chosen from hydrogen, $C_1$-$C_6$alkyl, ($C_1$-$C_4$alkoxy)($C_1$-$C_4$alkyl), ($C_3$-$C_7$cycloalkyl)$C_0$-$C_2$alkyl, —$CO_2C_1$-$C_6$alkyl, and —$CO_2C_0$-$C_2$alkyl($C_3$-$C_7$cycloalkyl), or $R^1$ and $R^2$ together may be a 3-6 membered carbocyclic ring or a 4-6-membered heterocycloalkyl ring containing one heteroatom or substituted heteroatom chosen from NH, N—$C_1$-$C_6$alkyl, NCO—$C_1$-$C_0$-alkyl, $NCO_2$—$C_1$-$C_6$-alkyl, $NSO_2$—$C_1$-$C_6$-alkyl, O, S and $SO_2$.

$R^3$ and $R^4$ are independently chosen from hydrogen, fluoro, and methyl or $R^3$ and $R^4$ can be taken together to form a $C_3$-$C_5$ saturated or partially unsaturated carbocyclic ring or an oxetanyl ring which is optionally 2,2 or 3,3 disubstituted with halogen or $C_1$-$C_2$alkyl.

$A^1$ is a 5-6-membered heteroarylene group containing 1-3 heteroatoms independently chosen from N, O, and S and optionally substituted with one or more substituents independently chosen from halogen, hydroxyl, cyano, $C_1$-$C_0$-alkyl, $C_1$-$C_6$alkoxy, ($C_3$-$C_7$-cycloalkyl)$C_0$-$C_2$alkyl, $C_1$-$C_2$haloalkyl, and $C_1$-$C_2$haloalkoxy.

$A^2$ is —$CO_2H$, —$Si(CH_3)_2$—$CO_2H$, —$CO_2NHSO_2$—$R^5$, —$SO_2NH$—CO—$R^5$, where $R^5$ is $C_1$-$C_6$alkyl, $C_3$-$C_7$-cycloalkyl, or a 4-6 membered heterocycloalkyl group containing one oxygen atom, or $A^2$ is a 5-membered heteroaryl group containing up to 4 heteroatoms independently chosen from N, O, and S and optionally substituted with one or two oxo groups.

$X^1$, $X^2$, $X^3$, $X^4$, and $X^5$ are aromatic ring atoms chosen from N and C, where up to 3 of $X^1$, $X^2$, $X^3$, $X^4$, and $X^5$ are N ring atoms and each C ring atom is optionally substituted with $R^6$ where each $R^6$ is independently chosen from halogen, hydroxyl, cyano, amino, —$CONH_2$, $C_1$-$C_6$alkyl, $C_1$-$C_6$alkoxy, $C_1$-$C_2$haloalkyl, $C_1$-$C_2$haloalkoxy, mono- or di-($C_1$-$C_6$alkylamino)$C_0$-$C_2$alkyl, ($C_3$-$C_7$cycloalkyl)$C_0$-$C_2$alkyl, ($C_3$-$C_7$cycloalkyl)$C_0$-$C_2$alkoxy, ($C_1$-$C_6$alkyl$SO_2$)$C_0$-$C_2$alkyl, $C_1$-$C_6$alkylNHCO—, and ($C_1$-$C_6$ alkyl)$_2$NCO—.

Q is absent or is —$CH_2$—, —$CH_2CH_2$— —$OCH_2$—, —$CH_2C(CH_2CH_2)CH_2$—, or —$CH_2C(CH_2OCH_2)CH_2$—.

The disclosure also provides pharmaceutical compositions comprising a compound of Formula 1 or salt thereof, together with a pharmaceutically acceptable carrier.

The disclosure further includes methods of treating diseases and disorders mediated, at least in part, by prostaglandin levels or cyclooxygenase activity (COX1 or COX2).

DETAILED DESCRIPTION

Terminology

In order for the present disclosure to be more readily understood, certain terms and phrases are defined below and throughout the specification.

The articles "a" and "an" are used herein to refer to one or to more than one (i.e., to at least one) of the grammatical object of the article. By way of example, "an element" means one element or more than one element.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," or the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03. The open-end phrases such as "comprising" include and encompass the close-ended phrases. Comprising may be amended to the more limiting phrases "consisting essentially of" of "consisting of" as needed.

The definition of each expression, e.g., alkyl, m, n, or the like, when it occurs more than once in any structure, is intended to be independent of its definition elsewhere in the same structure.

It will be understood that "substitution" or "substituted with" includes the implicit proviso that such substitution is in accordance with permitted valence of the substituted atom and the substituent, and that the substitution results in a stable compound, e.g., a compound which does not spontaneously undergo transformation such as by rearrangement, cyclization, elimination, or other reaction.

The term "substituted" is also contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein below. The permissible substituents may be one or more and the same or different for appropriate organic compounds. For purposes of this disclosure, the heteroatoms such as nitrogen may have hydrogen substituents and/or any permissible substituents of organic compounds described herein which satisfy the valences of the heteroatoms. This disclosure is not intended to be limited in any manner by the permissible substituents of organic compounds. "H—" is not considered a substituent.

Suitable groups that may be present on a "substituted" or "optionally substituted" position include, but are not limited to, e.g., halogen; cyano; —OH; oxo; —$NH_2$; nitro; azido; alkanoyl (such as a $C_2$-$C_6$ alkanoyl group); $C(O)NH_2$; alkyl groups (including cycloalkyl and (cycloalkyl)alkyl groups) having 1 to about 8 carbon atoms, or 1 to about 6 carbon atoms; alkenyl and alkynyl groups including groups having one or more unsaturated linkages and from 2 to about 8, or 2 to about 6 carbon atoms; alkoxy groups having one or more oxygen linkages and from 1 to about 8, or from 1 to about 6 carbon atoms; aryloxy such as phenoxy; alkylthio groups including those having one or more thioether linkages and from 1 to about 8 carbon atoms, or from 1 to about 6 carbon atoms; alkylsulfinyl groups including those having one or more sulfinyl linkages and from 1 to about 8 carbon atoms, or from 1 to about 6 carbon atoms; alkylsulfonyl groups including those having one or more sulfonyl linkages and from 1 to about 8 carbon atoms, or from 1 to about 6 carbon atoms; aminoalkyl groups including groups having one or more N atoms and from 1 to about 8, or from 1 to about 6 carbon atoms; mono- or dialkylamino groups including groups having alkyl groups from 1 to about 6 carbon atoms; mono- or dialkylcarboxamido groups (i.e. alkylNHC(O)—, ($alkyl_1$)($alkyl_2$)NC(O)—, alkylC(O)NH—, or $alkyl_1$C(O)N($alkyl_2$)—) having alkyl groups from about 1 to about 6 carbon atoms; carbocyclyl such as aryl having 6 or more carbons and one or more rings, (e.g., phenyl, biphenyl, naphthyl, or the like, each ring either substituted or unsubstituted aromatic); or a saturated, unsaturated, or aromatic heterocycle having 1 to 3 separate or fused rings with 3 to about 8 members per ring and one or more N, O or S atoms, e.g. coumarinyl, quinolinyl, isoquinolinyl, quinazolinyl, pyridyl, pyrazinyl, pyrimidinyl, furanyl, pyrrolyl, thienyl, thiazolyl, triazinyl, oxazolyl, isoxazolyl, imidazolyl, indolyl, benzofuranyl, benzothiazolyl, tetrahydrofuranyl, tetrahydropyranyl, piperidinyl, morpholinyl, piperazinyl, and pyrrolidinyl. Such heterocycles may be further substituted, e.g. with hydroxy, alkyl, alkoxy, halogen and amino. In certain embodiments "optionally substituted" includes one or more substituents independently chosen from halogen, hydroxyl, oxo, amino, cyano, —CHO, —$CO_2H$, —$C(O)NH_2$, $C_1$-$C_6$-alkyl, $C_2$-$C_6$-alkenyl, $C_1$-$C_6$-alkoxy, $C_2$-$C_6$-alkanoyl, $C_1$-$C_6$-alkylester, (mono- and di-$C_1$-$C_6$-alkylamino)$C_0$-$C_2$-alkyl, (mono- and di-$C_1$-$C_6$-alkylamino)(CO)$C_0$-$C_2$-alkyl, $C_1$-$C_2$-haloalkyl, $C_1$-$C_2$haloalkoxy, and heterocyclic substituents of 5-6 members and 1 to 3 N, O or S atoms, i.e. pyridyl, pyrazinyl, pyrimidinyl, furanyl, pyrrolyl, thienyl, thiazolyl, triazinyl, oxazolyl, isoxazolyl, imidazolyl, tetrahydrofuranyl, tetrahydropyranyl, piperidinyl, morpholinyl, piperazinyl, and pyrrolidinyl, each of which heterocycle can be substituted by amino, $C_1$-$C_6$-alkyl, $C_1$-$C_6$-alkoxy, or —$CONH_2$. In certain embodiments "optionally substituted" includes halogen, hydroxyl, cyano, nitro, oxo, —$CONH_2$, amino, ono- or di-$C_1$-$C_4$alkylcarboxamide, and $C_1$-$C_6$hydrocarbyl, which $C_1$-$C_6$hydrocarbyl group, a hydrocarbon chain in which carbon atoms are joined by single, double or triple bonds, and any one carbon atom can be replaced by O, NH, or N($C_1$-$C_4$alkyl) and which hydrocarbyl group is optionally substituted with one or more substituents independently chosen from hydroxyl, halogen, and amino. When the substituent is oxo (═O) then 2 hydrogen atoms are replaced. When an oxo group substitutes an aryl or heteroaryl group, aromaticity of the group is lost. When an oxo group substitutes a heteroaryl group the resulting heterocyclic group can sometimes have tautomeric forms. For example a pyridyl group substituted by oxo at the 2- or 4-position can sometimes be written as a hydroxypyridine.

The convention of naming into the ring is used for substituents in this disclosure unless the context clearly indicates otherwise. For example, "(cycloalkyl)alkyl" indicates a cycloalkyl group with an alkyl linker, and the point of attachment is at the terminal carbon of the alkyl group.

A dash "-" is also used to indicate a point of attachment in a substituent.

The term "saturated," as used herein, pertains to compounds and/or groups which do not have any carbon-carbon double bonds or carbon-carbon triple bonds.

The term "unsaturated," as used herein, pertains to compounds and/or groups which have at least one carbon-carbon double bond or carbon-carbon triple bond.

Compounds of Formula 1 include compounds of the formula having isotopic substitutions at any position. Isotopes include those atoms having the same atomic number but different mass numbers. By way of general example, and without limitation, isotopes of hydrogen include tritium and deuterium and isotopes of carbon include $^{11}C$, $^{13}C$, and $^{14}C$.

The term "aromatic" refers to a planar or polycyclic structure characterized by a cyclically conjugated molecular moiety containing 4n+2 electrons, wherein n is the absolute value of an integer. Aromatic molecules containing fused, or joined, rings also are referred to as bicyclic aromatic rings. For example, bicyclic aromatic rings containing heteroatoms in a hydrocarbon ring structure are referred to as bicyclic heteroaryl rings.

For purposes of this disclosure, the chemical elements are identified in accordance with the Periodic Table of the Elements, CAS version, Handbook of Chemistry and Physics, 67th Ed., 1986-87, inside cover.

The term "alkyl" means a branched or unbranched aliphatic radical containing the indicated number of carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 2-methylcyclopentyl, and 1-cyclohexylethyl. When alkyl is used in conjunction with another group, e.g. ($C_3$-$C_7$cycloalkyl)$C_0$-$C_2$alkyl, cycloalkyl and alkyl have the definitions set forth in this disclosure and the point of attachment is on the alkyl group. $C_0$alkyl is a covalent bond, in this example between the cycloalkyl group and the group it substitutes.

The term "cyclic," as used herein, pertains to compounds and/or groups which have one ring, or two or more rings (e.g., spiro, fused, bridged).

"Cyclolalkyl" is a saturated carbocyclic ring having the indicated number of carbon ring atoms, for example $C_3$-$C_7$cycloalkyl is a cyclopropyl, cyclobutyl, cyclopentyl, cyclohexyl, or cycloheptanyl group.

The term "carbocyclyl" as used herein means monocyclic or multicyclic (e.g., bicyclic, tricyclic, etc.) hydrocarbons containing from 3 to 12 carbon atoms that is completely saturated or has one or more unsaturated bonds, and for the avoidance of doubt, the degree of unsaturation does not result in an aromatic ring system (e.g. phenyl). Examples of carbocyclyl groups include 1-cyclopropyl, 1-cyclobutyl, 2-cyclopentyl, 1-cyclopentenyl, 3-cyclohexyl, 1-cyclohexenyl and 2-cyclopentenylmethyl.

A "carbocyclic acid isostere" is a substituent group with a similar shape, electronic properties, and biological properties to a carboxylic acid substituent at the same position.

A non-limiting list of carboxylic acid isosteres includes —$Si(CH_3)_2$—$CO_2H$, —$CO_2NHSO_2$—R, —$SO_2NH$—CO—R, hydroxamic acids (e.g. —CONHOH, —N(OH)COR), hydroxamic esters (e.g. —CONHOR', —ONHCOR'), —$PO(OH)_2$, —PO(OH)H, —$SO_2OH$, —$SO_2H$, —$SO_2NH_2$, —$NHSO_2R'$, acylsulfonamides (e.g. —$CONHSO_2R'$, —$CONHSO_2NR_2$), sulfonylureas (e.g. —$NHCONHSO_2R'$), acylureas (e.g. —NHCONHCOR'), tetrazole, Thiazolidine dione, oxazolidine dione, oxadiazol-5(4H)-one, oxathiadiazole-2-oxide, oxadiazol-5(4H)-thione, isoxazole, tetramic acid, cyclopentane-1,3-diones, cyclpentane-1,2-diones, squaric acids (e.g. 3-hydroxy-cyclobut-3-ene-1,2-dione, 3-hydroxy-4-amino-cyclobut-3-ene-1,2-dione), substituted phenols (e.g. —S-phenol, fluorophenol, di-fluorophenol, —SO-phenyl, —$SO_2$phenyl). Where R is hydrogen, alkyl, including cycloalkyl and (cycloalkyl)alkyl, and heterocycloalkyl and R' is alkyl, including cycloalkyl and (cycloalkyl)alkyl). A "heterocylic group" a cyclic group containing at least on ring heteroatom chosen from N, O, and S. The heterocyclic group can be fully saturated, i.e. a heterocycloalkyl group, partially unsaturated, e.g. a heterocycloalkenyl group, or aromatic, e.g. a heteroaryl group. The heterocyclic group can contain one ring having 4 to 7 ring members and one, two, three, or four heteroatoms independently chosen from N, O, and S. It is preferred that not more than two heteroatoms are O or S and O and S atoms are not adjacent.

A "heteroaryl" is a stable monocyclic aromatic ring having the indicated number of ring atoms which contains from 1 to 4, or in some embodiments from 1 to 2, heteroatoms chosen from N, O, and S, with remaining ring atoms being carbon, or a stable bicyclic system containing at least one 5- to 7-membered aromatic ring which contains from 1 to 4, or in some embodiments from 1 to 2, heteroatoms chosen from N, O, and S, with remaining ring atoms being carbon. Monocyclic heteroaryl groups typically have from 5 to 7 ring atoms. In certain embodiments the heteroaryl group is a 5- or 6-membered heteroaryl group having 1, 2, 3, or 4 heteroatoms chosen from N, O, and S, with no more than 2 O atoms and 1 S atom. A "heteroarylene" group is a heteroaryl group which has hydrogen removed from two of its ring positions permitting it to serve as a bivalent linker. Non-limiting examples of suitable heteroaryl groups include furanyl, thiopheneyl, pyrrolyl, pyrazolyl, imidazolyl, 1,2,3-triazolyl, 1,2,4-triazolyl, isoxazolyl, oxazolyl, oxadiazolyl, isothiazolyl, thiazolyl, pyridinyl, pyrimidinyl, pyrazinyl, triazinyl, benzofuranyl, benzothiopheneyl, indolyl, quinolinyl, isoquinolinyl, benzimidazolyl, benzoxazolinyl, benzothiazolinyl, and quinazolinyl. The heteroaryl group is optionally substituted with 1, 2, 3, 4, or 5 substituents as recited herein, wherein the optional substituent can be present at any open position on the heteroaryl group. The heteroaryl group may be substituted with 1, 2, 3, 4, or 5 independently chosen substituents as recited herein, wherein the substituents can be present at any open position on the heteroaryl group.

The term "heterocycloalkyl," means a saturated ring group usually having 4- to 7-ring atoms with 1 or 2 ring atoms independently chosen from N, O, and S: Examples of heterocycloalkyl groups includes azepines, azetidinyl, morpholinyl, pyranyl, oxopiperidinyl, oxopyrrolidinyl, piperazinyl, piperidinyl, pyrrolidinyl, quinicludinyl, thiomorpholinyl, tetrahydropyranyl and tetrahydrofuranyl.

The term "aryl," as used herein means a phenyl group, naphthyl or anthracenyl group. The aryl groups of the present disclosure can be optionally substituted with 1, 2, 3, 4 or 5 substituents.

The term "halo" or "halogen" means —Cl, —Br, —I or —F.

The term "haloalkyl" means an alkyl group, as defined herein, wherein at least one hydrogen is replaced with a halogen, as defined herein. Representative examples of haloalkyl include, but are not limited to, chloromethyl, 2-fluoroethyl, trifluoromethyl, pentafluoroethyl, and 2-chloro-3-fluoropentyl.

"Haloalkoxy" is a haloalkyl group linked through an oxygen atom.

The term "hydroxyl" as used herein means an —OH group.

The term "alkoxy" as used herein means an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

The term "cyano" as used herein means a —C≡N group.

"Mono- or di-alkylamino" is bound to the group it substitutes via a nitrogen atom and the nitrogen atom is substituted with one or two alkyl groups as defined herein, having the indicated number of carbon atoms. The alkyl groups of a dialkylamino may be the same or different.

The abbreviations Me, Et, Ph, Tf, Nf, Ts, and Ms represent methyl, ethyl, phenyl, trifluoromethanesulfonyl, nonafluorobutanesulfonyl, p-toluenesulfonyl and methanesulfonyl, respectively. A more comprehensive list of the abbreviations utilized by organic chemists of ordinary skill in the art appears in the first issue of each volume of the *Journal of Organic Chemistry*; this list is typically presented in a table entitled *Standard List of Abbreviations*.

As used herein, the term "administering" means providing a pharmaceutical agent or composition to a subject, and includes, but is not limited to, administering by a medical professional and self-administering.

As used throughout this disclosure, the term "pharmaceutically effective amount of a compound for pharmaceutical use" means an amount of compound that exhibits the intended pharmaceutical or therapeutic or diagnostic effect when administered.

"Pharmaceutically acceptable salt" refers to a salt of a compound that is pharmaceutically acceptable and that possesses the desired pharmacological activity of the parent compound. Such salts may include: (i) acid addition salts, formed with inorganic acids such as hydrochloric acid, hydrobromic acid, sulfuric acid, nitric acid, phosphoric acid, or the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl) benzoic acid, cinnamic acid, mandelic acid, methanesulfonic acid, or the like; or (ii) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, N-methylglucamine, dicyclohexylamine, or the like.

"Therapeutically effective amount" or "effective amount" refers to the amount of a compound that, when administered to a subject for treating or diagnosing or monitoring a disease, or at least one of the clinical symptoms of a disease or disorder, is sufficient to affect such treatment for the disease, disorder, or symptom. The "therapeutically effective amount" can vary depending on the compound, the disease, disorder, and/or symptoms of the disease or disorder, severity of the disease, disorder, and/or symptoms of the disease or disorder, the age of the subject to be treated, and/or the weight of the subject to be treated. An appropriate amount in any given instance can be readily apparent to those skilled in the art or capable of determination by routine experimentation.

"Treating" or "treatment" of any disease or disorder refers to arresting or ameliorating a disease, disorder, or at least one of the clinical symptoms of a disease or disorder, reducing the risk of acquiring a disease, disorder, or at least one of the clinical symptoms of a disease or disorder, mitigating (making less severe) at least one of the clinical symptoms of a disease or disorder, reducing the development of a disease, disorder or at least one of the clinical symptoms of the disease or disorder, or reducing the risk of developing a disease or disorder or at least one of the clinical symptoms of a disease or disorder. "Treating" or "treatment" also refers to inhibiting the disease or disorder, either physically, (e.g., stabilization of a discernible symptom), physiologically, (e.g., stabilization of a physical parameter), or both, or inhibiting at least one physical parameter which may not be discernible to the subject. Further, "treating" or "treatment" refers to monitoring, delaying or preventing the onset or reoccurrence of the disease or disorder or at least symptoms thereof in a subject which may be exposed to or predisposed to or may have previously suffered from a disease or disorder even though that subject does not yet experience or display symptoms of the disease or disorder.

Preventing means effecting a statistically significant decrease in the likelihood of developing a disease or disorder.

As used herein, the term "subject" means a human or non-human animal selected for treatment or therapy.

As used herein, the phrase "subject suspected of having" means a subject exhibiting one or more clinical indicators of a disease or condition.

Chemical Description

In certain embodiments, the disclosure relates to compounds of Formula 1. In certain embodiments, these compounds inhibit a prostaglandin transporter. In certain embodiments, the compounds demonstrate low-nM inhibition and excellent selectivity. In certain embodiments, the disclosure relates to a method of treating pain, inflammation, or obesity comprising administering to a patient (human or non-human animal) in need thereof an effective amount of a compound of Formula 1.

In addition to the compounds of Formula 1 and salts thereof as discussed in the SUMMARY section the disclosure also includes the compounds and salts of Formula 1 in which the variables, e.g. $X^1$-$X^5$, $A^1$, $A^2$, and $R^1$-$R^4$ carry the following definitions. Any combination of variables is permitted so long as a stable compound results.

(1)

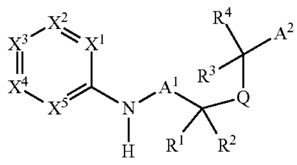

(1) The disclosure includes compounds and salts of Formula 1 in which $R^1$ and $R^2$ are independently chosen from hydrogen, $C_1$-$C_0$alkyl, and —$CO_2$—$C_1$-$C_6$alkyl.

$R^3$ and $R^4$ are independently chosen from hydrogen, fluoro, and methyl.

$A^1$ is a 5-6-membered heteroarylene group containing 1-3 heteroatoms independently chosen from N, O, and S and optionally substituted with one or more substituents independently chosen from halogen, hydroxyl, cyano, $C_1$-$C_6$alkyl, $C_1$-$C_6$alkoxy, ($C_3$-$C_7$-cycloalkyl)$C_0$-$C_2$alkyl, $C_1$-$C_2$haloalkyl, and $C_1$-$C_2$haloalkoxy.

$A^2$ is —$CO_2H$, —$Si(CH_3)_2$—$CO_2H$, —$CO_2NHSO_2$—$R^5$, —$SO_2NH$—CO—$R^5$, where $R^5$ is $C_1$-$C_6$alkyl, $C_3$-$C_7$-cycloalkyl, an oxetanyl group, or a tetrahydrofuranyl group, or $A^2$ is a tetrazolyl, thiadiazolyl, or oxathiadiazolyl group, each of which is optionally substituted with one or two oxo groups. In certain embodiments $A^2$ is a carboxylic acid isostere, such as a group selected from the carboxylic acid isosteres listed in the "terminology" section.

$X^1$, $X^2$, $X^3$, $X^4$, and $X^5$ are aromatic ring atoms chosen from N and C, where up to 3 of $X^1$, $X^2$, $X^3$, $X^4$, and $X^5$ are N ring atoms and each C ring atom is optionally substituted with $R^6$ where each $R^6$ is independently chosen from halogen, hydroxyl, cyano, amino, —$CONH_2$, $C_1$-$C_6$alkyl, $C_1$-$C_6$-alkoxy, $C_1$-$C_2$haloalkyl, $C_1$-$C_2$haloalkoxy, $C_3$-$C_7$-cycloalkyl, $C_3$-$C_7$-cycloalkyl-O—, ($C_1$-$C_6$alkyl$SO_2$)$C_0$-$C_2$alkyl, $C_1$-$C_6$alkylNHCO—, and ($C_1$-$C_6$alkyl)$_2$NCO.

Q is absent or is —CH2, —CH2CH2- or —OCH2.

(2) The disclosure also includes compounds and salts of Formula 1 in which:

$R^1$ is —$CO_2$—$C_1$-$C_6$alkyl or $C_1$-$C_6$alkyl and $R^2$ is $C_1$-$C_6$alkyl.

$A^1$ is a thiazolyl, oxazolyl, imidazolyl, 1,3,4-oxadiazolyl, pyrimidinyl, pyridyl, or pyrazinyl heteroarylene group, each of which is optionally substituted with one or more substituents independently chosen $^3$ and $R^4$ are hydrogen or methyl.

$A^2$ is —$CO_2H$, —$Si(CH_3)_2$—$CO_2H$, —$CO_2NHSO_2$—$R^5$, or —$SO_2NH$—CO—$R^5$, where $R^5$ is $C_1$-$C_6$alkyl.

$X^1$, $X^2$, $X^3$, $X^4$, and $X^5$ are aromatic ring atoms chosen from N and C, where 0 or 1 of $X^1$, $X^2$, $X^3$, $X^4$, and $X^5$ are N ring atoms and each C ring atom is optionally substituted with $R^6$ where each $R^6$ is independently chosen from fluoro, chloro, hydroxyl, cyano, —$CONH_2$, $C_1$-$C_2$alkyl, $C_1$-$C_2$alkoxy, trifluoromethyl, trifluoromethoxy, $C_1$-$C_2$alkyl$SO_2$-, $C_1$-$C_2$alkylNHCO—, and ($C_1$-$C_2$ alkyl)$_2$NCO—.

Q is —$CH_2$—.

The disclosure includes compounds and salts of Formula 1 in which $A^2$ has any of the following definitions.

(1) $A^2$ is —$CO_2H$, —$Si(CH_3)_2$—$CO_2H$, —$CO_2NHSO_2$—$R^5$, —$SO_2NH$—CO—$R^5$, where $R^5$ is $C_1$-$C_6$alkyl, $C_3$-$C_7$-cycloalkyl, oxetan-3-yl, or tetrahydrofuran-3-yl.

(2) $A^2$ is 5-oxo-1,3,4-oxadiazol-2-yl, 5-oxo-1,2,4-thiadiazol-3-yl, or 2,2-dioxo-1,2,3,5-oxathiadiazol-4-yl.

(3) $A^2$ is —$CO_2H$, —$Si(CH_3)_2$—$CO_2H$, —$CO_2NHSO_2$—$R^5$, —$SO_2NH$—CO—$R^5$, where $R^5$ is $C_1$-$C_6$alkyl, $C_3$-$C_7$-cycloalkyl, or a 4-6 membered heterocycloalkyl group containing one oxygen atom, or $A^2$ is a 5-membered heteroaryl group containing up to 4 heteroatoms independently chosen from N, O, and S and optionally substituted with one or two oxo groups.

The disclosure includes compounds and salts of Formula 1 of subformulae —Formula 1A, 1B, 1C, 1D, or 1E (1A)

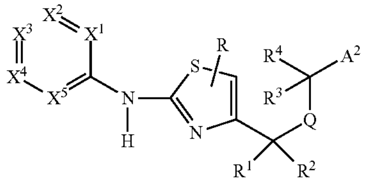

(1B)

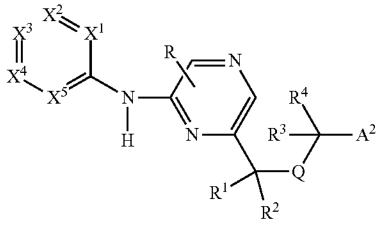

(1C)

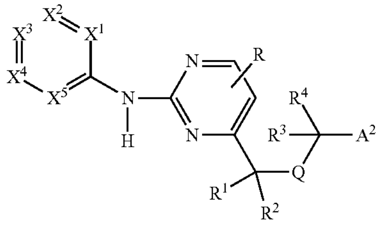

-continued (1D)

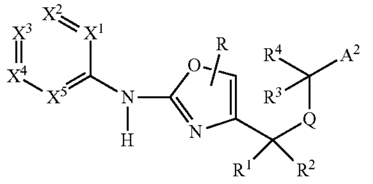

(1E)

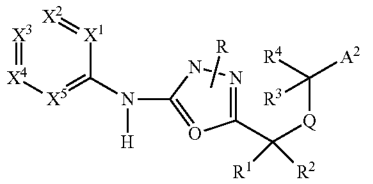

In Formula 1A, 1B, 1C, 1D, and 1E in which R is absent or is one or more substituents independently chosen from halogen, cyano, and $C_1$-$C_2$alkyl, or $C_1$-$C_2$alkoxy.

In certain embodiments the disclosure includes compounds and salts of Formula 1 in which $X^1$-$X^5$ have the following definitions.

(1) $X^1$-$X^5$ containing ring is a phenyl or pyridyl and is optionally substituted with 1, 2, or 3 substituents independently chosen from fluoro, chloro, bromo, hydroxyl, cyano, $CH_3SO_2$— $C_1$-$C_3$alkyl, $C_1$-$C_3$alkoxy, trifluoromethyl, and trifluromethoxy.

(2) $X^1$-$X^5$ containing ring is a phenyl or 2-pyridyl and is optionally substituted with 1, 2, or 3 substituents independently chosen from fluoro, chloro, hydroxyl, methyl, methoxy, and $CH_3SO_2$—.

The disclosure includes compounds and salts of Formula 1 in which the variables $R^1$—$R^4$ and $A^2$ have the following definitions.

(1) $R^1$ is ethyl, —$CO_2$-ethyl, or —$CO_2$-t-butyl; and $R^2$ is ethyl.

(2) Q is —$CH_2$— and $R^3$ and $R^4$ are both hydrogen.

(3) $A^2$ is —$CO_2H$.

The disclosure includes compounds and salts of Formula 1 in which the group

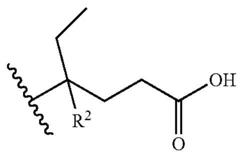

is

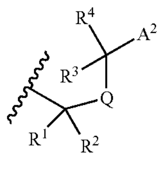

where $R^2$ is $C_1$-$C_3$alkyl, ($C_1$-$C_3$alkoxy)($C_1$-$C_3$alkyl), (cyclopropyl)$C_0$-$C_2$alkyl, —$CO_2C_1$-$C_6$alkyl, or —$CO_2C_0$-$C_2$alkyl ($C_3$-$C_7$cyclopropyl).

Pharmaceutical Compositions

The disclosure includes pharmaceutical compositions in which one or more compounds are an admixture or otherwise combined with one or more compounds and may be in the presence or absence of commonly used excipients (or "pharmaceutically acceptable carriers"); for example, but not limited to: i) diluents and carriers such as starch, mannitol, lactose, dextrose, sucrose, sorbitol, cellulose, or the like; ii) binders such as starch paste, gelatin, magnesium aluminum silicate, methylcellulose, alginates, gelatin, sodium carboxymethyl-cellulose, polyvinylpyrrolidone or the like; iii) lubricants such as stearic acid, talcum, silica, polyethylene glycol, polypropylene glycol or the like; iv) absorbents, colorants, sweeteners or the like; v) disintegrates, (e.g., calcium carbonate and sodium bicarbonate) such as effervescent mixtures or the like; vi) excipients (e.g. cyclodextrins or the like); vii) surface active agents (e.g., cetyl alcohol, glycerol monostearate), adsorptive carriers (e.g., kaolin and bentonite), emulsifiers or the like. Examples of carriers include, without limitation, any liquids, liquid crystals, solids or semi-solids, such as water or saline, gels, creams, salves, solvents, diluents, fluid ointment bases, ointments, pastes, implants, liposomes, micelles, giant micelles, or the like, which are suitable for use in the compositions.

It should be understood that the ingredients particularly mentioned above are merely examples and that some embodiments of formulations comprising the compositions of the present disclosure include other suitable components and agents. The invention further includes packages, vessels, or any other type of container that contain a compound of the present invention.

Furthermore, the disclosure includes compositions prepared using conventional mixing, granulating, or coating methods and may contain 0.01 to 90% of the active ingredients. In some embodiments, the one or more compounds are for pharmaceutical use or for diagnostic use. Such methods can be used, for example, to prepare a bio-enhanced pharmaceutical composition in which the solubility of the compound(s) is (are) enhanced. In some embodiments, the resulting compositions contain a pharmaceutically effective amount of a compound for pharmaceutical or diagnostic use. The resulting compositions (formulations) may be presented in unit dosage form and may be prepared by methods known in the art of pharmacy. All methodology includes the act of bringing the active ingredient(s) into association with the carrier which constitutes one or more ingredients. Therefore, compositions (formulations) are prepared by blending active ingredient(s) with a liquid carrier or a finely divided solid carrier, and/or both, and then, if needed, shaping the product into a desired formulation.

In some embodiments, the compositions can be combined with other components. Examples include, but are not limited to, coatings, depots, matrices for time release and osmotic pump components.

Typical compositions of the disclosure contain compound from about 90 to about 80% by weight, from about 80 to about 70% by weight, from about 70 to about 60% by weight, from about 60 to about 50% by weight, from about 50 to about 40% by weight, from about 40 to about 30% by weight, from about 30 to 20% by weight, from about 20 to about 10% by weight, from about 10 to about 4% by weight, from about 4.0% to about 2.0% by weight, from about 2.0% to about 1.0% by weight, and even from about 1.0% to about 0.01% by weight of a compound of Formula 1. The effective amount of compounds or compositions of the disclosure may range from about 0.1 to 100 milligrams (mg) per kilogram (kg) of subject weight. In certain embodiments, the compounds or compositions of the disclosure are administered at from about 0.0001 mg/kg to 0.1 mg/kg (e.g. diagnostic monitoring), or from 0.1 mg/kg to 2 mg/kg, or from about 2 mg/kg to 5 mg/kg; in other embodiments, from about 5 mg/kg to 10 mg/kg, from about 10 mg/kg to 20 mg/kg, from about 20 mg/kg to 30 mg/kg, from about 30 mg/kg to 40 mg/kg, from about 40 mg/kg to 50 mg/kg, from about 50 mg/kg to 75 mg/kg or from about 75 mg/kg to 100 mg/kg.

Methods of Treatment

Examples of methods of administration include, but are not limited to, oral administration (e.g., ingestion, buccal or sublingual administration), anal or rectal administration, topical application, aerosol application, inhalation, intraperitoneal administration, intravenous administration, transdermal administration, intradermal administration, subdermal administration, intramuscular administration, intrauterine administration, vaginal administration, administration into a body cavity, surgical administration, administration into the lumen or parenchyma of an organ, and parenteral administration. The compositions can be administered in any form by any means. Examples of forms of administration include, but are not limited to, injections, solutions, creams, gels, implants, ointments, emulsions, suspensions, microspheres, powders, particles, microparticles, nanoparticles, liposomes, pastes, patches, capsules, suppositories, tablets, transdermal delivery devices, sprays, suppositories, aerosols, or other means familiar to one of ordinary skill in the art.

In some embodiments, the one or more compounds, or compositions of the present disclosure, are administered to persons or animals to provide substances in any dose range that will produce desired physiological or pharmacological results. Dosage will depend upon the substance or substances administered, the therapeutic endpoint desired, the diagnostic endpoint desired, the desired effective concentration at the site of action or in a body fluid, and the type of administration. In some embodiments, the compounds and compositions of the present disclosure may be administered to a subject. In certain embodiments, the subject is a mammal. Embodiments in which the subject is a human patient are within the scope of the disclosure. Embodiments in which the subject is a companion animal, e g cat, dog, or a livestock animal, e.g. sheep, bovine, or swine, are within the scope of the disclosure.

The disclosure provides a method of inhibiting prostaglandin transporter (PGT) activity in a subject comprising administering to the subject any of the compounds disclosed herein in an amount effective to inhibit PGT activity.

The disclosure also provides a method of inhibiting cyclooxygenase 2 (COX2) activity in a subject comprising administering to the subject any of the compounds disclosed herein in an amount effective to inhibit COX2 activity.

The disclosure further provides a method of treating a disease or disorder in a subject associated with prostaglandin activity and/or COX2 activity comprising administering to the subject any of the compounds disclosed herein in an amount effective to inhibit prostaglandin transporter (PGT) activity and/or COX2 activity. The disease or disorder can be, for example, arthritis, fever, common cold, hypertension, glaucoma, a wound, initiation of labor, dysmenorrhea, menstrual cramps, inflammatory bowel disease, Crohn's disease, emphysema, acute respiratory distress syndrome, asthma, bronchitis, chronic obstructive pulmonary disease, Alzheimer's disease, organ transplant toxicity, cachexia, allergic reactions, allergic contact hypersensitivity, cancer, tissue ulceration, peptic ulcers, gastritis, regional enteritis, ulcerative colitis, diverticulitis, recurrent gastrointestinal lesion, gastrointestinal bleeding, coagulation, anemia, synovitis, gout, ankylosing spondylitis, inflammation, restenosis, periodontal disease, epidermolysis bullosa, osteoporosis, loosening of artificial joint implants; atherosclerosis, aortic aneurysm, periarteritis nodosa, congestive heart failure, myocardial infarction, stroke, cerebral ischemia, head trauma, spinal cord injury, neuralgia, neuro-degenerative disorders, autoimmune disorders, Huntington's disease, Parkinson's disease, migraine, depression, peripheral neuropathy, pain, gingivitis, cerebral amyloid angiopathy, nootropic or cognition enhancement, amyotrophic lateral sclerosis, multiple sclerosis, ocular angiogenesis, corneal injury, macular degeneration, conjunctivitis, abnormal wound healing, muscle or joint sprains or strains, tendonitis, skin disorders, myasthenia gravis, polymyositis, myositis, bursitis, burns, diabetes, tumor invasion, tumor growth, tumor metastasis, corneal scarring, scleritis, immunodeficiency diseases, sepsis, premature labor, hypoprothrombinemia, hemophilia, thyroiditis, sarcoidosis, Behcet's syndrome, hypersensitivity, kidney disease, rickettsial infections, protozoan diseases, reproductive disorders or septic shock. Diseases and disorders that can be treated with a compound of the disclosure particularly include obesity, Non-alcoholic fatty liver disease (NAFLD), Nonalcoholic steatohepatitis (NASH), pulmonary arterial hypertension, acute kidney injury, warm ischemia of organ transplants, arterial hypertension, inflammatory bowel disease, bone marrow engraftment, Raynaud's, disease, and atherosclerotic arterial insufficiency. Additionally, compounds of Formula 1 can be used to treat acute pain, rheumatoid arthritis, and osteoarthritis. Preferably, the disease or disorder is inflammation, pain, a wound, or a cardiovascular disease, such as hypertension or atherosclerosis.

Cisplatin is a widely used and effective chemotherapeutic agent. Unfortunately, cisplatin can cause nephrotoxicity. Cisplatin nephrotoxicity is marked by inflammation of renal epithelial cells, renal cell death, and, in some cases, acute renal failure. Cisplatin nephrotoxicity can be prevented, mitigated, or treated by administration of a compound of Formula 1 prior to cisplatin administration, concurrently with cisplatin administration, or after cisplatin administration. The compound of Formula 1 can be the only therapeutic agent administered (in addition to cisplatin) or may be administered in combination with mannitol. Compounds of Formula 1 can also be used to prevent, mitigate, or treat nephrotoxicity caused by other drugs, including but not limiting to acyclovir, aminoglycoside antibiotics (e.g. gentamicin), amphotericin B, atazanavir, beta-lactam antibiotics, cyclosporine, ifosfamide, indinavir, indomethacin, and tenofovir.

The disclosure provides a method of treating pulmonary hypertension in a subject. PAH is a rare and devastating disease with a current five-year survival rate that is lower than that of the five-year survival rate for cancer. About 15-30% of patients have an underlying genetic cause. PAH usually manifests itself in childhood and middle age but is also increasingly diagnosed in elderly patients.

Early symptoms of PAH include exertional dyspnea and fatigue. As the disease progresses, syncope, chest pain, palpitations, and peripheral edema develop. Advanced disease is characterized by severe dyspnea, fatigue, pain, anxiety, depression, and what has been termed "existential distress."

The pulmonary vasculature in PAH undergoes vasoconstriction, cell proliferation, proliferative vasculopathy of small pulmonary arterioles, fibrosis, and microthrombosis. These changes increase pulmonary vascular resistance, which increases pressure in the pulmonary circulation, causing hypertrophy of the heart's right ventricle with reduction cardiac output and progressive venous congestion. Cardiac output is also reduced because the dilated RV impinges on left ventricular filling through ventricular interdependence.

PAH is the cause or major contributor to death in 88% of patients diagnosed with this disorder. Current five-year survival of patients with PAH is 65%. The most common specific causes of death are progressive right heart failure, sudden death, or an intercurrent illness in which PAH predisposes to worse outcomes (most often respiratory failure). Patients with PAH who experience cardiac arrest rarely have a shockable rhythm and uncommonly survive.

PAH is managed by administering agonists of the prostacyclin signaling pathway. Advanced cases of PAH are managed by continuous intravenous delivery of prostacyclin analogs via an indwelling catheter and external pump.

Endogenous prostacyclin is increased when the prostaglandin transporter PGT (Slco2a1) is genetically or pharmacologically inhibited. Our preliminary data in an established rat model of PAH indicate that pharmacological PGT inhibition reduces PAH-induced right ventricular pressure and hypertrophy to the same degree as intravenous iloprost, a potent synthetic prostacyclin analogue.

Two established rodent models of PAH are used to confirm the efficacy of PGT inhibitors for treating PAH. Chronic hypoxia and VEGF Receptor blockage with a VEGF antagonist, such as Sugen's SU5416, is known to cause pronounced pulmonary hypertension in rats and mice. Another rat PAH model includes monocrotaline administered to Sprague-Dawley rats. Subcutaneous injection of monocrotaline in rodents induces an acute pulmonary artery injury with endothelial and type II pneumocyte damage and in situ thrombosis. Pulmonary edema follows. Reduction in PAH symptoms in rodents in either of these models is considered predictive of efficacy in humans.

The disclosure includes methods of treating PAH by administering an effective amount of a PGT inhibitor of the disclosure. An effective amount is an amount of a PGT inhibitor of the disclosure is an amount sufficient to eliminate or significantly decrease any symptom of PAH. An effective amount of a PGT inhibitor of the disclosure is also an amount effective to increase endogenous prostacyclin levels in a patient. An effective amount of a PGT inhibitor of the disclosure can also be an amount effective to changes the level of a marker for PAH, for example an amount effective to decrease a marker of lung pathology, an amount effective to reorient macrophages to the "M2" type, induction of SERCA2b, or an amount effective to modulate enothelin B receptor gene expression.

The disclosure includes methods of preventing or delaying PAH in a patient predisposed to PAH, for example a patient having a genetic mutation associated with PAH. Preventing in this context means significantly reducing the probability of developing PAH symptoms or significantly delaying the onset of PAH symptoms in a patient predisposed to developing PAH.

Methods of treatment include administering a PGT inhibitor of the disclosure as the only active agent and methods of treatment in which the PCT inhibitor of the disclosure is a first active agent and is administered in combination with one or more additional active agents. In the context of PAH treatment, suitable additional active agents include synthetic prostacyclins, phosphodiesterase type-5 inhibitors, endothelin receptor antagonists, anticoagulants (to prevent pulmonary embolism), diuretics, and nitric oxide elevating agents. Suitable additional active agents include currently used medications for treating PAH, such as ambrisentan, amlodipine, bosentan, bumetinide, dilitiazem, digoxin, epoprostenol, furosemide, iloprost, macitentan, nifedipine, riociguat, selexipag, sildenafil, spironolactone, tadalafil, treprostinil, and warfarin.

Methods of treatment of the disclosure include treating hyperinflammation associated with respiratory viral infections, including SARS-CoV-2 (COVID 19) infections. In severe SARS-CoV-2 cases, fatality can be caused by the rapid development of severe lung injury characteristic of acute respiratory distress syndrome (ARDS). Although ARDS is a complication of SARS-CoV-2 infection, it is not viral replication or infection that causes tissue injury; rather, it is the result of dysregulated hyperinflammation in response to viral infection. This pathology is characterized by intense, rapid stimulation of the innate immune response that triggers activation of the Nod-like receptor family, pyrin domain-containing 3 (NLRP3) inflammasome pathway and release of its products including the proinflammatory cytokines IL-6 and IL-1β. NLRP3 is inhibited and constitutive interleukin 1-beta (IL-1β) secretion from lipopolysaccharide-primed peripheral blood monocytes is substantially reduced by high doses of PGE2. PGT inhibition increases systemic PGE2. PGT inhibitors of the disclosure can be used to dampen the dysregulated hyperinflammation in response to SARS-CoV-2 viral infection.

The disclosure includes a method of treating ARDS or hyperinflammation associated with SARS-CoV-2 infection in a subject comprising administering an effective amount of a PGT inhibitor of the disclosure to the subject. An effective amount is an amount effective to reduce any symptom of ARDS or hyperinflammation associated with SARS-CoV-2 viral infection in a subject in need of such treatment including an amount sufficient to reduce a marker of hyperinflammation in the subject. The disclosure also includes a method of preventing ARDS or hyperinflammation associated with SARS-CoV-2 viral infection in a subject. Preventing, in the context of ARDS or hyperinflammation associated with SARS-CoV-2 viral infection, means significantly reducing the probability of developing these conditions or significantly lessening the probability of poor outcome from these conditions, in a subject at risk for developing ARDS or hyperinflammation associated with SARS-CoV-2 viral infection. For example, a PGT inhibitor of the disclosure may be given prophylactically to an asymptomatic or newly diagnosed SARS-CoV-2 patient or to a health care worker.

The disclosure includes an a method of treating hyperinflammation associated with SARS-CoV-2 viral infection in which the PGT inhibitor of the disclosure is the only active agent administered to the subject and in which the PCT inhibitor of the disclosure is a first active agent and is administered in combination with one or more additional active agents. In the context of treating hyperinflammation associated with SARS-CoV-2 viral infection suitable additional active agents include convalescent plasm, adrenaline, angiotensin receptor blockers, cyclosporine, dexamethasone, epinephrine, meplazumab, methylprednisolone, nafamostat and camstat mesylate, prednisolone, prednisone, tocilizumab, viral protease inhibitors, and viral polymerase inhibitors.

EXAMPLES

Abbreviations

ACN Acetonitrile
Boc tert-butoxy carbonyl
DBU 1,8-Diazabicyclo[5.4.0]undec-7-ene DCM Dichloromethane
DME Dimethoxyethane
DMF Dimethylformamide
DMSO Dimethyl Sulfoxide
EDTA Ethylenediaminetetraacetic acid
EtOAc Ethyl Acetate
EtOH Ethanol
FA Formic Acid
HPLC High pressure liquid chromatography
Hz Hertz
IPA Isopropyl alcohol
LAH Lithium aluminium hydride
LCMS Liquid Chromatography/Mass Spectrometry
LiHMDS Lithium bis(trimethylsilyl)amide
MHz Megahertz
NBS N-Bromosuccinimide
NCS N-Chlorosuccinimide
NMR Nuclear Magnetic Resonance
MeOH Methanol
MPLC Medium pressure liquid chromatography
MTBE Methyl tert-butyl ether
PE Petroleum ether
Psi Pound-force per square inch
SFC Supercritical fluid chromatography
TEA Triethylamine
THF Tetrahydrofuran
TFA Trifluoracetic acid
TLC Thin layer chromatography
General Methods All air- or moisture-sensitive reactions were performed under positive pressure of nitrogen with oven-dried glassware. Anhydrous solvents or reagents such as dichloromethane, N,N-dimethylformamide (DMF), acetonitrile, methanol, and triethylamine were commercially available reagent grade materials unless indicated otherwise. $^1H$ NMR spectra were recorded on a Bruker 400 MHz spectrometer. Chemical shifts are reported in ppm with non-deuterated solvent (DMSO-h6 at 2.50 ppm) as internal standard for DMSO-d6 solutions. All of the analogs tested in the biological assays have a purity greater than 95% based on LCMS analysis.

The LCMS gradient was 15-90% B in 3.40 min and 90-100% B at 3.40-3.85 min, 100-15% B in 0.01 min, and then held at 15% for 0.64 min, the flow rate was 0.80 ml/min Mobile phase A was 10 mM Ammonium bicarbonate, mobile phase B was HPLC grade acetonitrile. The column used for chromatography was a 2.1*50 mm Xbridge Shield RPC18 column (5 um particles). Detection methods are diode array (DAD) and evaporative light scattering (ELSD) detection as well as positive electrospray ionization. MS range was 100-1000.

Example 1. Synthesis of 4-Ethoxycarbonyl-4-[2-(2-Hydroxyanilino)Thiazol-4-yl]Hexanoic Acid (Cmp. 1 (RS))

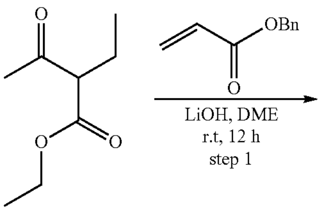

-continued

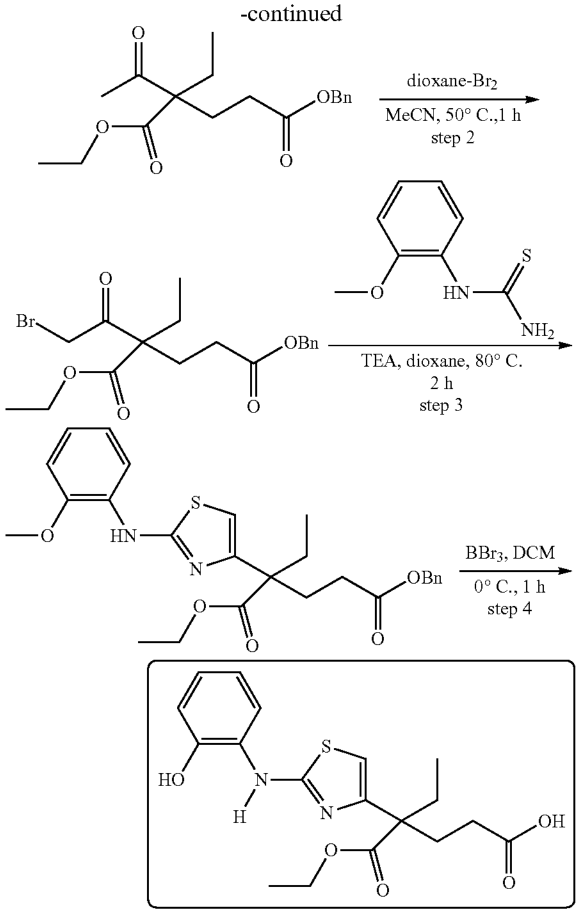

Cmp. 1, racemate

Step 1. Preparation of O5-benzyl O1-ethyl 2-acetyl-2-ethyl-pentanedioate

To a solution of ethyl 2-ethyl-3-oxo-butanoate (5 grams (g), 31.61 millimoles (mmol), 5.08 milliliters (mL), 1 equivalents (eq)) in DME (20 mL) was added $LiOH{\cdot}H_2O$ (2.65 g, 63.21 mmol, 2 eq). After 0.5 hours (h), benzyl prop-2-enoate (10.25 g, 63.21 mmol, 2 eq) was added and the mixture was stirred at 25° C. for 11.5 h. It was poured into water (200 mL). The aqueous phase was extracted with ethyl acetate (50 mL*3). The combined organic phase was washed with brine (100 mL*2), dried over anhydrous $Na_2SO_4$, filtered and concentrated under vacuum. The residue was purified by silica gel chromatography (100-200 mesh silica gel, Petroleum ether/Ethyl acetate=50/1, 5/1) to afford the title compound (3.4 g, 10.61 mmol, 33.58% yield) as colorless oil.

$^1H$ NMR: (400 MHz, CHLOROFORM-d) δ ppm 7.45-7.30 (m, 5H), 5.11 (s, 2H), 4.25-4.15 (m, 2H), 2.32-2.15 (m, 4H), 2.15-2.12 (m, 3H), 1.97-1.82 (m, 2H), 1.30-1.25 (m, 3H), 0.80 (t, J=7.5 Hz, 3H).

Step 2. Preparation of O5-benzyl O1-ethyl 2-(2-bromoacetyl)-2-ethyl-pentanedioate To a solution of O5-benzyl O1-ethyl 2-acetyl-2-ethyl-pentanedioate (0.7 g, 2.18 mmol, 1 eq) in $CH_3CN$ (10 mL) was added 1-bromo-1,4-dioxan-1-ium; bromide (541.67 milligrams (mg), 2.18 mmol, 1 eq). The mixture was stirred at 50° C. for 1 h. It was poured into water (10 mL). The aqueous phase was extracted with ethyl acetate (20 mL*3). The combined organic phase was washed with brine (30 mL*2), dried over anhydrous $Na_2SO_4$, filtered and concentrated under vacuum to afford the title compound (0.9 g, crude) as yellow oil and used directly.

LCMS: $(M+H^+)$: 401.1@1.291 min (10-90% ACN in $H_2O$, 2.0 min).

Preparation of Dioxane-$Br_2$ $Br_2$(9.35 g, 58.48 mmol, 3.01 mL, 1 eq) was added to dioxane (5.15 g, 58.48 mmol, 5.00 mL, 1 eq) at 25° C. and the mixture was stirred at 25° C. for 10 min. Yellow solid was formed, then Petroleum ether (PE) (10 mL) was added to the mixture and filtered. The filter cake was collected to afford the title compound (9 g crude) as yellow solid and stored in a refrigerator.

Step 3. Preparation of O5-benzyl O1-ethyl 2-ethyl-2-[2-(2-methoxyanilino)thiazol-4-yl]pentanedioate To a solution of O5-benzyl O1-ethyl 2-(2-bromoacetyl)-2-ethyl-pentanedioate (0.45 g, 1.13 mmol, 1 eq), (2-methoxyphenyl)thiourea (184.86 mg, 1.01 mmol, 0.9 eq) in dioxane (5 mL) was added TEA (171.07 mg, 1.69 mmol, 235.31 microliters (uL), 1.5 eq). The mixture was stirred at 80° C. for 2 h. It was filtered and the filtrate was concentrated under vacuum. The residue was purified by silica gel chromatography (1000 mesh silica gel, Petroleum ether/Ethyl acetate=10/1, 3/1) to afford the title compound (0.23 g, 26.22% yield, 62% purity) as yellow oil.

LCMS: $(M+H^+)$: 483.1@1.548 min (5-95% ACN in $H_2O$, 4.5 min).

Step 4. Preparation of 4-ethoxycarbonyl-4-[2-(2-hydroxyanilino)thiazol-4-yl]hexanoic acid (Cmp. 1)

To a solution of O5-benzyl O1-ethyl 2-ethyl-2-[2-(2-methoxyanilino)thiazol-4-yl]pentanedioate (0.2 g, 414.43 micromole (umol), 1 eq) in DCM (10 mL) was added $BBr_3$ (311.47 mg, 1.24 mmol, 119.80 uL, 3 eq) at 0° C. Then the mixture was stirred at 0° C. for 1 h. It was quenched with water (10 mL). The aqueous phase was extracted with DCM (10 mL*3). The combined organic phase was dried over anhydrous $Na_2SO_4$, filtered and concentrated under vacuum. The residue was purified by preparative (prep)-HPLC (HCl) to afford the title compound (15.8 mg, 97.04% purity, as a HCl salt) as white solid.

LCMS: $(M+H^+)$: 379.1@2.829 min (1-100% ACN in $H_2O$, 4.5 min).

$^1H$ NMR: (400 MHz, METHANOL-d4) δ ppm 7.36 (dd, J=1.5, 7.9 Hz, 1H), 7.26 (dt, J=1.5, 7.8 Hz, 1H), 7.03-6.92 (m, 3H), 4.25 (q, J=7.2 Hz, 2H), 2.36-2.16 (m, 4H), 2.13-2.00 (m, 2H), 1.29 (t, J=7.2 Hz, 3H), 0.88 (t, J=7.5 Hz, 3H).

Example 2. Synthesis of Methyl 4-ethyl-4-[2-(4-methylanilino)thiazol-4-yl]hexanoate (Cmp. 2)

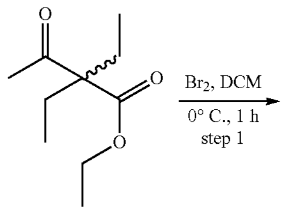

-continued

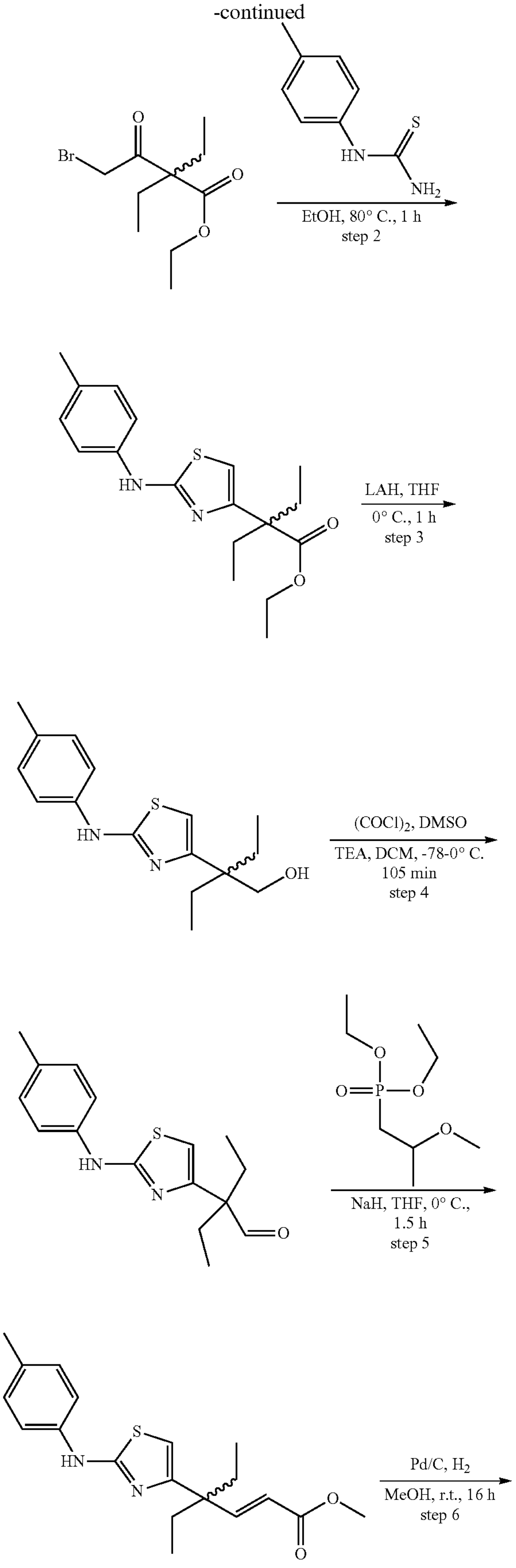

-continued

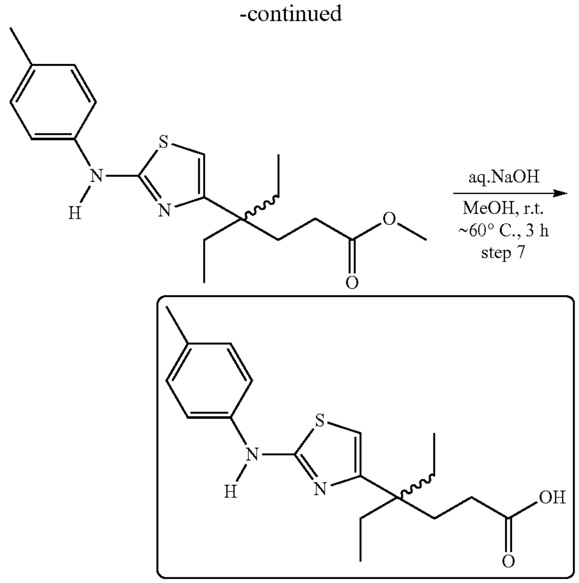

Cmp. 2

Step 1. Synthesis of Ethyl 4-bromo-2,2-diethyl-3-oxo-butanoate

To a solution of ethyl 2,2-diethyl-3-oxo-butanoate (1 g, 5.37 mmol, 1 eq) in DCM (10 mL) was added $Br_2$ (772.24 mg, 4.83 mmol, 249.11 uL, 0.9 eq) dropwise at 0° C. The mixture was stirred at 0° C. for 1 h. The pH was adjusted to 9 with saturated $NaHCO_3$ solution. The aqueous phase was extracted with ethyl acetate (20 mL*3). The combined organic phase was dried over anhydrous $Na_2SO_4$, filtered and concentrated under vacuum to afford the title compound (1.4 g, crude) as yellow oil which was directly in the next step without any further purification.

Step 2. Preparation of Ethyl 2-ethyl-2-[2-(4-methylanilino) thiazol-4-yl]butanoate To a solution of ethyl 4-bromo-2,2-diethyl-3-oxo-butanoate (1.4 g, 5.28 mmol, 1 eq), p-tolylthiourea (877.79 mg, 5.28 mmol, 1 eq) in EtOH (10 mL) was added TEA (801.45 mg, 7.92 mmol, 1.10 mL, 1.5 eq). The mixture was stirred at 80° C. for 1 h. It was concentrated under vacuum. The residue was purified by silica gel chromatography (column height: 250 mm, diameter: 100 mm, 100-200 mesh silica gel, Petroleum ether/Ethyl acetate=20/1, 5/1) to afford the title compound (1.2 g, 1.80 mmol, 34.18% yield, 50% purity) as yellow oil.

LCMS: ($M+H^+$): 333.2@1.290 min (10-90% ACN in $H_2O$, 2.0 min).

Step 3. Preparation of 2-ethyl-2-[2-(4-methylanilino) thiazol-4-yl]butan-1-ol

To a solution of ethyl 2-ethyl-2-[2-(4-methylanilino) thiazol-4-yl]butanoate (0.4 g, 1.20 mmol, 1 eq) in THF (10 mL) was added $LiAlH_4$ (105.03 mg, 2.77 mmol, 2.3 eq) at 0° C., then the mixture was stirred at 0° C. for 1 h. It was quenched with HCl (1 normal (N)), extracted with ethyl acetate (20 mL*3). The combined organic phase was dried over anhydrous $Na_2SO_4$, filtered and concentrated under vacuum to afford the title compound (0.4 g, crude) as yellow oil and used directly in the next step without any further purification.

Step 4. Preparation of 2-ethyl-2-[2-(4-methylanilino) thiazol-4-yl]butanal

To a solution of $(COCl)_2$ (349.63 mg, 2.75 mmol, 241.12 uL, 2 eq) in DCM (10 mL) was added DMSO (215.23 mg, 2.75 mmol, 215.23 uL, 2 eq) at −78° C. After the reaction was stirred for 15 min, 2-ethyl-2-[2-(4-methylanilino)thiazol-4-yl]butan-1-ol (0.4 g, 1.38 mmol, 1 eq) in DCM (1 mL) was added and the resulting mixture was stirred for 30 min. Then TEA (696.85 mg, 6.89 mmol, 958.52 uL, 5 eq) was added dropwise. The mixture was allowed to warm to 0° C. and stirred at this temperature for 1 h. It was poured into saturated (Sat.) $NH_4C_1$ solution (30 mL). The aqueous phase was extracted with ethyl acetate (30 mL*2). The combined organic phase was dried over anhydrous $Na_2SO_4$, filtered and concentrated under vacuum. The residue was purified by silica gel chromatography (1000 mesh silica gel, Petroleum ether/Ethyl acetate=20/1, 5/1) to afford the title compound (0.3 g, crude) as yellow oil.

Step 5. Preparation of Methyl (E)-4-ethyl-4-[2-(4-methylanilino) thiazol-4-yl]hex-2-enoate To a solution of methyl 2-diethoxyphosphorylacetate (437.22 mg, 2.08 mmol, 2 eq) in THF (10 mL) was added NaH (83.21 mg, 2.08 mmol, 60% purity, 2 eq) at 0° C. After 0.5 h, 2-ethyl-2-[2-(4-methylanilino) thiazol-4-yl]butanal (0.3 g, 1.04 mmol, 1 eq) was added and the resulting mixture was stirred at 0° C. for 1 h. It was quenched with Sat. $NH_4Cl$ solution (10 mL). The aqueous phase was extracted with ethyl acetate (30 mL*3). The combined organic phase was dried over anhydrous $Na_2SO_4$, filtered and concentrated under vacuum. The residue was purified by silica gel chromatography (100-200 mesh silica gel, Petroleum ether/Ethyl acetate=20/1, 5/1) to afford 0.19 g crude product. The crude product was purified by prep-HPLC (FA condition) to afford the title compound (30 mg, 68.37 umol, 6.57% yield, 89% purity, FA salt) as colorless oil.

Step 6. Preparation of Methyl 4-ethyl-4-[2-(4-methylanilino) thiazol-4-yl]hexanoate To a solution of methyl (E)-4-ethyl-4-[2-(4-methylanilino) thiazol-4-yl]hex-2-enoate (20 mg, 51.22 umol, 1 eq, FA salt) in MeOH (5 mL) was added Pd/C (50 mg, 10% purity) under $N_2$. The suspension was degassed under vacuum and purged with $H_2$ several times. The mixture was stirred under $H_2$ (15 psi) at 25° C. for 16 h. It was filtered and the filtrate was concentrated under vacuum to afford the title compound (30 mg, crude) as colorless oil which was used in next step directly.

LCMS: ($M+H^+$): 347.0@1.491 min (5-95% ACN in $H_2O$, 2.0 min).

Step 7. Preparation of 4-ethyl-4-[2-(4-methylanilino) thiazol-4-yl]hexanoic acid (Cmp. 2)

A mixture of methyl 4-ethyl-4-[2-(4-methylanilino)thiazol-4-yl]hexanoate (30 mg, 86.58 umol, 1 eq) and NaOH (2 molar (M), 432.92 uL, 10 eq) in MeOH (2 mL) was stirred at 25° C. for 2 h. LCMS show 50% reactant was remained. Then the mixture was stirred at 60° C. for 1 h. It was concentrated in vacuum. The residue was adjusted pH to 3 with HCl (1N). The aqueous phase was extracted with ethyl acetate (10 mL*3). The combined organic phase dried over anhydrous $Na_2SO_4$, filtered and concentrated under vacuum. The residue was purified by prep-HPLC (FA) to afford the title compound (Cmp. 2) (6.9 mg, 17.11 umol, 19.76% yield, 93.84% purity, FA salt) as a white solid.

LCMS: $(M+H^+)$: 333.1@2.260 min (10-80% ACN in $H_2O$, 4.5 min).

$^1H$ NMR: (400 MHz, METHANOL-d4) δ ppm 7.43 (d, J=8.6 Hz, 2H), 7.09 (d, J=8.4 Hz, 2H), 6.29 (s, 1H), 2.28 (s, 3H), 2.11-1.90 (m, 4H), 1.79-1.60 (m, 4H), 0.74 (t, J=7.5 Hz, 6H).

Example 3. Synthesis of 4-ethoxycarbonyl-4-[2-(4-methylanilino)thiazol-4-yl]hexanoic acid (Cmp. 3 (RS))

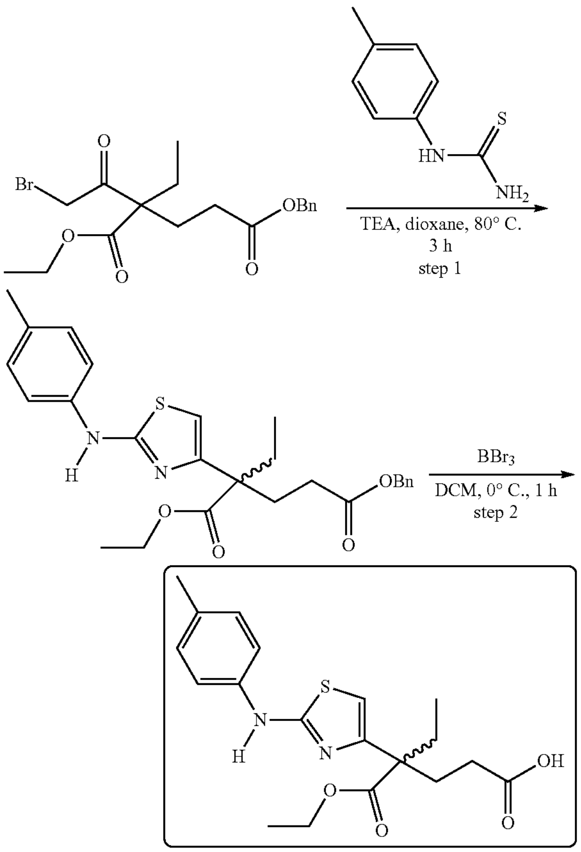

Cmp. 3

Step 1. Synthesis of O5-benzyl O1-ethyl 2-ethyl-2-[2-(4-methylanilino)thiazol-4-yl]pentanedioate To a solution of O5-benzyl O1-ethyl 2-(2-bromoacetyl)-2-ethyl-pentanedioate (350 mg, 876.59 umol, 1 eq) in dioxane (4.5 mL) was added p-tolylthiourea (131.15 mg, 788.93 umol, 0.9 eq) and TEA (266.11 mg, 2.63 mmol, 366.03 uL, 3 eq). The mixture was stirred at 80° C. for 3 h. It was cooled to the room temperature. The combined mixture was filtered and the filtrate was concentrated under vacuum. The residue was purified by MPLC ($SiO_2$, PE/EtOAc=10/1 to 4:1) to afford the title compound (380 mg, 651.53 umol, 37.16% yield, 80% purity) as brown oil.

Step 2. 4-ethoxycarbonyl-4-[2-(4-methylanilino) thiazol-4-yl]hexanoic acid (Cmp. 3)

To a solution of O5-benzyl O1-ethyl 2-ethyl-2-[2-(4-methylanilino)thiazol-4-yl]pentanedioate (330 mg, 707.26 umol, 1 eq) in DCM (4 mL) was added $BBr_3$ (531.55 mg, 2.12 mmol, 204.44 uL, 3 eq) at 0° C. The mixture was stirred at 0° C. for 1 h. The mixture was concentrated and washed with PE (50 mL) to collect the cake. The residue was purified by prep-HPLC (HCl condition) to afford the title compound (60 mg, 98.07% purity, HCl salt) as yellow solid.

LCMS: $(M+H^+)$: 377.1@2.862 min (10-100% ACN in $H_2O$, 4.5 min).

$^1H$ NMR: (400 MHz, METHANOL-d4) δ ppm 7.40 (d, J=8.4 Hz, 2H), 7.12 (d, J=8.2 Hz, 2H), 6.60 (s, 1H), 4.23-4.13 (m, 2H), 2.42-2.22 (m, 5H), 2.20-2.11 (m, 2H), 2.11-1.97 (m, 2H), 1.24 (t, J=7.2 Hz, 3H), 0.83 (t, J=7.4 Hz, 3H).

Example 4. Synthesis of 4-ethoxycarbonyl-4-[2-(4-methylsulfonylanilino)thiazol-4-yl]hexanoic acid (Cmp. 4a) and 4-[5-bromo-2-(4-methylsulfonylanilino)thiazol-4-yl]-4-ethoxycarbonyl-hexanoic acid (Cmp. 4b)

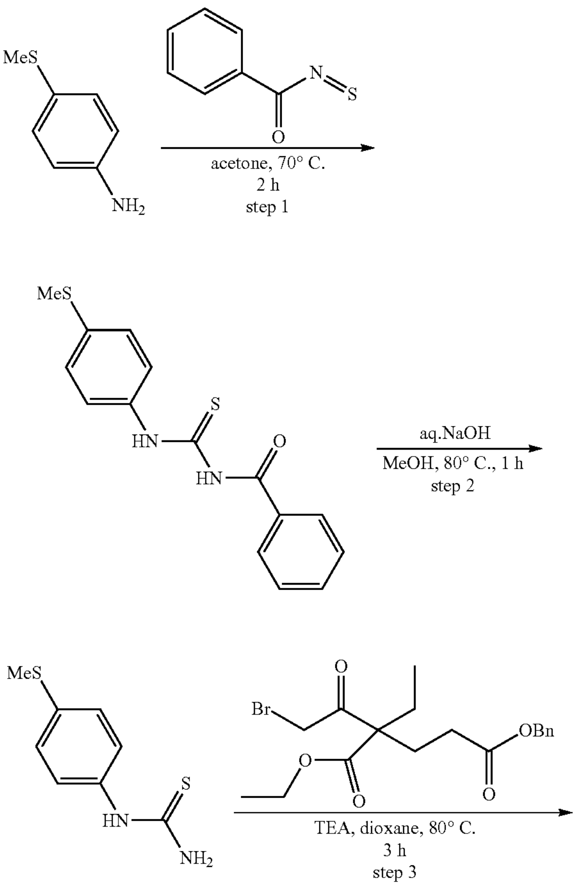

-continued

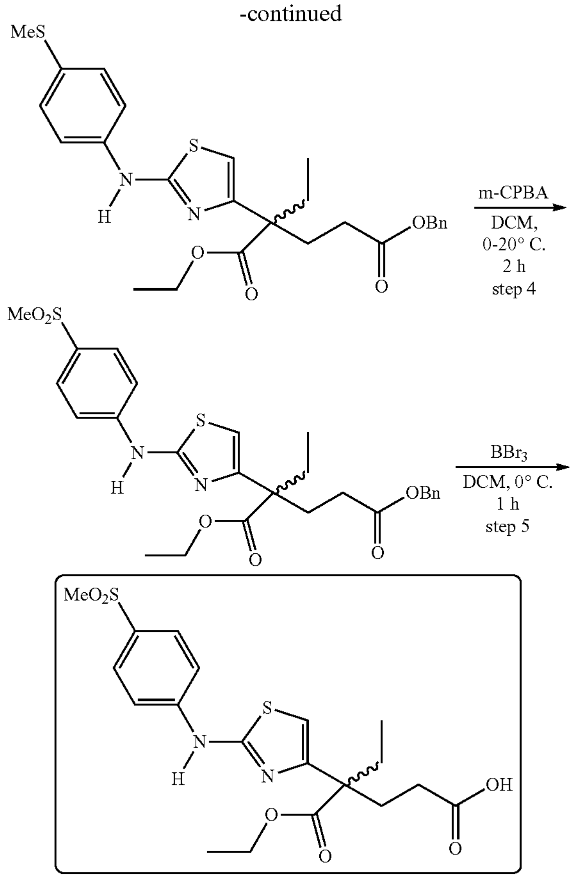

Cmp. 4a

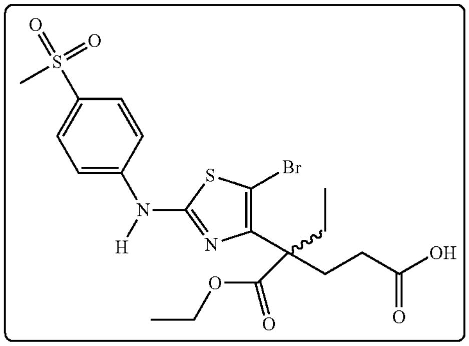

Cmp. 4b

Step 1. Synthesis of N-[(4-methylsulfanylphenyl) carbamothioyl]benzamide

To a solution of benzoyl isothiocyanate (2.58 g, 15.80 mmol, 2.13 mL, 1.1 eq) in acetone (20 mL) was added 4-methylsulfanylaniline (2 g, 14.37 mmol, 1.75 mL, 1 eq). The mixture was stirred at 70° C. for 2 h. It was cooled to the room temperature and poured in to water (100 mL). The gray solid was formed and filtered to afford the title compound (2.8 g, crude) as gray solid which was used in next step directly.

$^1$H NMR: (400 MHz, DMSO-d6) δ ppm 12.55 (s, 1H), 11.55 (s, 1H), 7.98 (d, J=7.3 Hz, 2H), 7.71-7.62 (m, 3H), 7.59-7.51 (m, 2H), 7.31 (d, J=8.6 Hz, 2H), 2.50 (br s, 3H).

Step 2. Synthesis of (4-methylsulfanylphenyl)thiourea

To a solution of N-[(4-methylsulfanylphenyl)carbamothioyl]benzamide (1 g, 3.31 mmol, 1 eq) in MeOH (10 mL) was added NaOH (1 M, 9.92 mL, 3 eq). The mixture was stirred at 80° C. for 1 h. It was cooled to room temperature and adjusted pH to 2 with aqueous (aq.) HCl (1 mole (M)). The gray solid was formed. It was filtered to afford the title compound (800 mg, crude) as gray solid.

Step 3. Synthesis of O5-benzyl O1-ethyl 2-ethyl-2-[2-(4-methylsulfanylanilino)thiazol-4-yl]pentanedioate To a solution of (4-methylsulfanylphenyl)thiourea (450 mg, 2.27 mmol, 1 eq) in dioxane (3 mL) was added O5-benzyl O1-ethyl 2-(2-bromoacetyl)-2-ethyl-pentanedioate (906.03 mg, 2.27 mmol, 1 eq) and TEA (688.86 mg, 6.81 mmol, 947.54 uL, 3 eq). The mixture was stirred at 80° C. for 3 h. It was cooled to the room temperature and poured into water (30 mL), extracted with EtOAc (3x30 mL), washed with brine, dried over anhydrous $Na_2SO_4$ and concentrated under vacuum. The residue was purified by column chromatography ($SiO_2$, PE:EtOAc=5:1 to 2:1) to afford the title compound (350 mg, 540.45 umol, 23.82% yield, 77% purity) as yellow oil.

LCMS: (M+H$^+$): 499.2@1.137 min (5-95% ACN in $H_2O$, 2 min).

Step 4. Synthesis of O5-benzyl O1-ethyl 2-ethyl-2-[2-(4-methylsulfonylanilino)thiazol-4-yl]pentanedioate To a solution of O5-benzyl O1-ethyl 2-ethyl-2-[2-(4-methylsulfanylanilino)thiazol-4-yl]pentanedioate (300 mg, 601.62 umol, 1 eq) in DCM (10 mL) was added m-CPBA (324.44 mg, 1.50 mmol, 80% purity, 2.5 eq) at 0° C. The mixture was stirred at 20° C. for 2 h. It was poured into sat. $NaHCO_3$ solution (10 mL). The aqueous phase was extracted with EtOAc (10 mL*3). The combined organic phase was washed with brine (10 mL*2), dried over anhydrous $Na_2SO_4$, filtered and concentrated under vacuum. The residue was purified by MPLC ($SiO_2$, PE:EtOAc=10/1 to 3/1) to afford the title compound (100 mg, 146.99 umol, 24.43% yield, 78% purity) as brown solid.

LCMS: (M+H$^+$): 531.1@2.617 min (5-95% ACN in $H_2O$, 4.5 min).

Step 5. Synthesis of 4-ethoxycarbonyl-4-[2-(4-methylsulfonylanilino)thiazol-4-yl]hexanoic acid (Cmp. 4a)

To a solution of O5-benzyl O1-ethyl 2-ethyl-2-[2-(4-methylsulfonylanilino)thiazol-4-yl]pentanedioate (20 mg, 37.69 umol, 1 eq) in DCM (1 mL) was added $BBr_3$ (28.33 mg, 113.07 umol, 10.89 uL, 3 eq) at 0° C. The mixture was stirred at 0° C. for 1 h. The mixture was concentrated and washed with PE (20 mL). The residue was purified by prep-HPLC (neutral condition) to afford the title compound (2 mg, 4.31 umol, 11.43% yield, 94.86% purity) as white solid.

LCMS: (M−H$^+$): 441.1@2.466 min (10-60% ACN in $H_2O$, 7 min).

$^1$H NMR: (400 MHz, METHANOL-d4) δ ppm 7.93-7.78 (m, 4H), 6.81-6.77 (m, 1H), 4.26-4.12 (m, 2H), 3.13-3.08 (m, 3H), 2.52-2.27 (m, 2H), 2.19-2.01 (m, 4H), 1.30-1.18 (m, 3H), 0.92-0.79 (m, 3H).

Step 6. Synthesis of 4-[5-bromo-2-(4-methylsulfonylanilino)thiazol-4-yl]-4-ethoxycarbonyl-hexanoic acid (Cmp. 4b)

To a solution of O5-benzyl O1-ethyl 2-ethyl-2-[2-(4-methylsulfonylanilino)thiazol-4-yl]pentanedioate (60 mg, 113.07 umol, 1 eq) in DCM (6 mL) was added $BBr_3$ (84.98 mg, 339.20 umol, 32.68 uL, 3 eq) at 0° C. The mixture was stirred at 0° C. for 1 h. The mixture was concentrated and washed with PE (20 mL) to obtain crude compound 4-ethoxycarbonyl-4-[2-(4-methylsulfonylanilino)thiazol-4-yl]hexanoic acid. On standing, the residue converts to the title compound, as a crude product. It was purified by prep-HPLC (neutral condition) to afford the title product (10.2 mg, 19.52 umol, 17.26% yield, 99.41% purity) as white solid.

LCMS: $(M+H^+)$: 520.9@3.094 min (10-60CD % ACN in $H_2O$, 7 min).

$^1$H NMR: (400 MHz, METHANOL-d4) δ ppm 7.92-7.80 (m, 4H), 4.29-4.17 (m, 2H), 3.11 (s, 3H), 2.53-2.39 (m, 2H), 2.37-2.09 (m, 4H), 1.29 (t, J=7.2 Hz, 3H), 0.88 (t, J=7.5 Hz, 3H).

Example 5. Synthesis of 4-ethoxycarbonyl-4-[6-(4-methylanilino)pyrazin-2-yl]hexanoic acid (Cmp. 5 (RS))

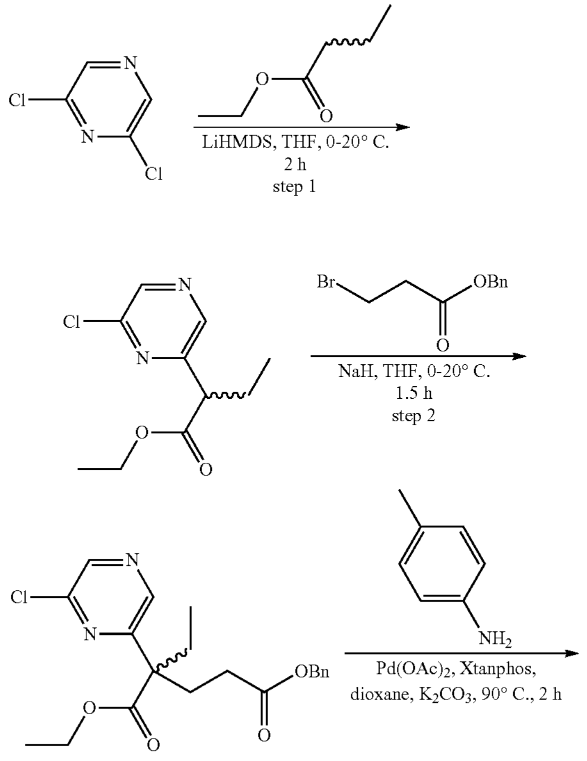

-continued

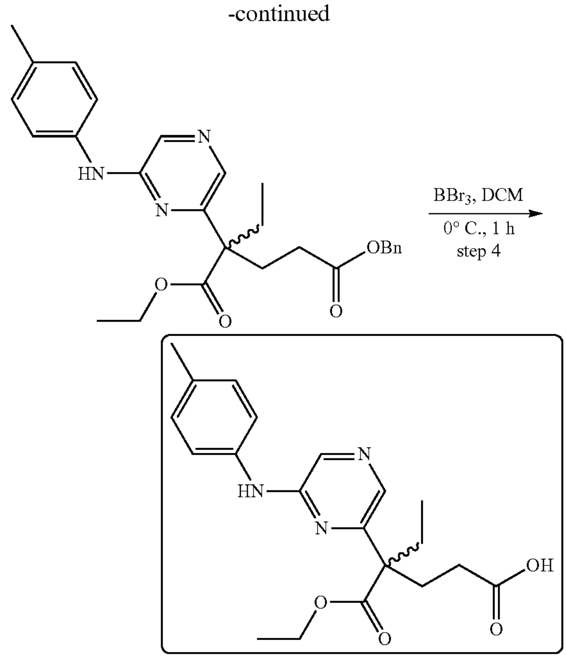

Cmp. 5

Step 1. Synthesis of ethyl 2-(6-chloropyrazin-2-yl)butanoate

To a solution of LiHMDS (1 M, 14.77 mL, 2.2 eq) in THF (15 mL) was added 2,6-dichloropyrazine (1 g, 6.71 mmol, 1 eq) and ethyl butanoate (857.67 mg, 7.38 mmol, 985.82 uL, 1.1 eq) under $N_2$ at 0° C. The mixture was stirred for 2 h, allowing the ice bath to warm to 20° C. The mixture was poured into saturated $NH_4Cl$ (50 mL), and extracted with EtOAc (3×50 mL), washed with brine, dried over anhydrous $Na_2SO_4$ and concentrated under vacuum. The residue was purified by MPLC ($SiO_2$, PE:EtOAc=20/1 to 5/1) to afford the title compound (1.1 g, 4.67 mmol, 69.51% yield, 97% purity) as brown oil.

$^1$H NMR: (400 MHz, METHANOL-d4) δ ppm 8.60-8.52 (m, 2H), 4.19-4.08 (m, 2H), 3.82 (t, J=7.6 Hz, 1H), 2.15 (quintet, J=7.3, 14.2 Hz, 1H), 2.03-1.86 (m, 1H), 1.19 (t, J=7.2 Hz, 3H), 0.91 (t, J=7.4 Hz, 3H).

Step 2. Synthesis of O5-benzyl O1-ethyl 2-(6-chloropyrazin-2-yl)-2-ethyl-pentanedioate To a solution of ethyl 2-(6-chloropyrazin-2-yl)butanoate (900 mg, 3.94 mmol, 1 eq) in THF (25 mL) was added NaH (236.12 mg, 5.90 mmol, 60% purity, 1.5 eq) at 0° C. The mixture was stirred at 0° C. for 0.5 h. Then benzyl 3-bromopropanoate (1.15 g, 4.72 mmol, 1.2 eq) was added. The mixture was stirred at 20° C. for 1 h. The mixture was poured into water (30 mL), extracted with EtOAc (3×30 mL), washed with brine, dried over anhydrous $Na_2SO_4$ and concentrated under vacuum. The residue was purified by MPLC ($SiO_2$, PE:EtOAc=20/1 to 4/1) to afford the title compound (1 g, 70% purity) as yellow oil.

$^1$H NMR: (400 MHz, METHANOL-d4) δ ppm 8.55 (d, J=19.6 Hz, 2H), 7.37-7.24 (m, 5H), 5.04 (s, 2H), 4.21-4.13 (m, 2H), 2.50-2.35 (m, 2H), 2.28-2.21 (m, 2H), 2.18-2.07 (m, 2H), 1.22-1.16 (m, 3H), 0.80 (t, J=7.5 Hz, 3H).

Step 3. Synthesis of O5-benzyl O1-ethyl 2-ethyl-2-[6-(4-methylanilino)pyrazin-2-yl]pentanedioate To a solution of O5-benzyl O1-ethyl 2-(6-chloropyrazin-2-yl)-2-ethyl-pentanedioate (600 mg, 1.54 mmol, 1 eq) in dioxane (12 mL) was added 4-methylaniline (205.61 mg, 1.92 mmol, 211.32 uL, 1.25 eq), $K_2CO_3$ (636.49 mg, 4.61 mmol, 3 eq), $Pd(OAc)_2$ (34.46 mg, 153.51 umol, 0.1 eq) and (5-diphenylphosphanyl-9,9-dimethyl-xanthen-4-yl)-diphenyl-phosphane (222.06 mg, 383.77 umol, 0.25 eq). The mixture was stirred at 90° C. for 2 h under $N_2$ atmosphere. It was cooled to the room temperature and poured into water (30 mL), extracted with EtOAc (3x30 mL), washed with brine, dried over anhydrous $Na_2SO_4$ and concentrated under vacuum. The residue was purified by MPLC ($SiO_2$, PE:EtOAc=20/1 to 4/1) to afford the title compound (600 mg, 1.13 mmol, 73.67% yield, 87% purity) as yellow oil.

LCMS: $(M+H^+)$: 462.4@3.148 min (10-80% ACN in $H_2O$, 4.5 min).

$^1H$ NMR: (400 MHz, CHLOROFORM-d) δ ppm 8.05 (s, 1H), 7.93 (s, 1H), 7.37-7.28 (m, 6H), 7.14 (d, J=8.2 Hz, 2H), 6.58-6.46 (m, 1H), 6.52 (s, 1H), 5.07 (s, 2H), 4.24-4.12 (m, 2H), 2.54-2.35 (m, 2H), 2.31-2.21 (m, 2H), 2.18-2.05 (m, 2H), 1.20 (t, J=7.1 Hz, 3H), 0.84 (t, J=7.5 Hz, 3H).

Step 4. Synthesis of 4-ethoxycarbonyl-4-[6-(4-methylanilino)pyrazin-2-yl]hexanoic acid (Cmp. 5)

To a solution of O5-benzyl O1-ethyl 2-ethyl-2-[6-(4-methylanilino)pyrazin-2-yl]pentanedioate (200 mg, 433.32 umol, 1 eq) in DCM (4 mL) was added $BBr_3$ (325.67 mg, 1.30 mmol, 125.26 uL, 3 eq) at 0° C. The mixture was stirred at 0° C. for 1 h. The mixture was concentrated and washed with PE (50 mL) to collect the cake. The residue was purified by prep-HPLC (HCl condition) to afford the title compound (21 mg, 51.12 umol, 11.80% yield, 99.30% purity, HCl salt) as yellow solid.

LCMS: $(M+H^+)$: 372.2@1.804 min (5-100% ACN in $H_2O$, 3 min).

$^1H$ NMR: (400 MHz, METHANOL-d4) δ ppm 8.13-7.81 (m, 2H), 7.53 (d, J=8.3 Hz, 2H), 7.12 (d, J=8.3 Hz, 2H), 4.18 (q, J=7.0 Hz, 2H), 2.51-2.32 (m, 2H), 2.30 (s, 3H), 2.26-2.08 (m, 4H), 1.24-1.11 (m, 3H), 0.85 (t, J=7.5 Hz, 3H).

Example 6. Synthesis of 4-[2-(2,4-difluoroanilino)thiazol-4-yl]-4-ethoxycarbonyl-hexanoic acid (Cmp. 6 (RS))

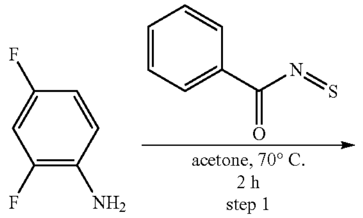

-continued

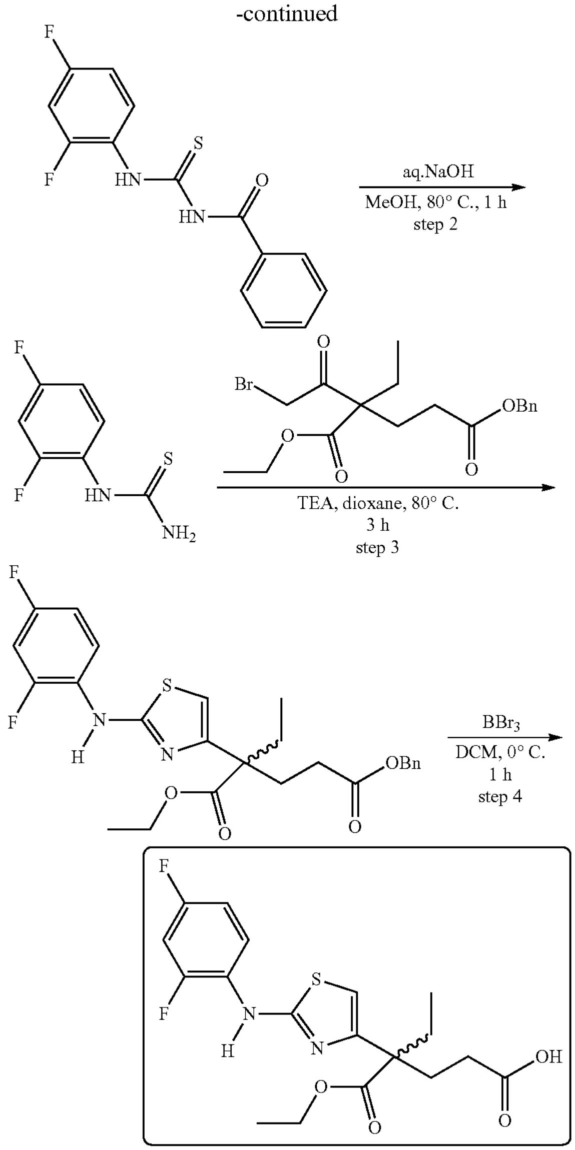

Cmp. 6

Step 1. Synthesis of N-[(2,4-difluorophenyl)carbamothioyl]benzamide

To a solution of 2,4-difluoroaniline (2 g, 15.49 mmol, 1 eq) in acetone (20 mL) was added benzoyl isothiocyanate (2.78 g, 17.04 mmol, 2.30 mL, 1.1 eq). The mixture was stirred at 70° C. for 2 h. It was cooled to the room temperature and poured in to water (100 mL). The yellow solid was formed. It was filtered to afford the title compound (4.1 g, crude) as yellow solid and used directly without further purification.

Step 2. Synthesis of (2,4-difluorophenyl)thiourea

To a mixture of N-[(2,4-difluorophenyl)carbamothioyl]benzamide (2 g, 6.84 mmol, 1 eq) in MeOH (30 mL) was added NaOH (1 M, 20.53 mL, 3 eq). The mixture was stirred at 80° C. for 1 h. It was cooled to the room temperature and poured into water (30 mL) and adjusted pH to 7 with aq. HCl (1M), extracted with EtOAc (3x30 mL). The combined organic layers was washed with brine, dried over anhydrous $Na_2SO_4$ and concentrated under vacuum to afford the title compound (1.1 g, crude) as white solid and used directly in the next step.

Step 3. Synthesis of O5-benzyl O1-ethyl 2-[2-(2,4-difluoroanilino)thiazol-4-yl]-2-ethyl-pentanedioate To a solution of O5-benzyl O1-ethyl 2-(2-bromoacetyl)-2-ethyl-pentanedioate (300 mg, 751.36 umol, 1 eq) in dioxane (3 mL) was added (2,4-difluorophenyl)thiourea (141.40 mg, 751.36 umol, 1 eq) and TEA (228.09 mg, 2.25 mmol, 313.74 uL, 3 eq). The mixture was stirred at 80° C. for 3 h. It was cooled to the room temperature and poured into water (30 mL), extracted with EtOAc (3×30 mL), washed with brine, dried over anhydrous $Na_2SO_4$ and concentrated under vacuum. The residue was purified by column chromatography ($SiO_2$, PE:EtOAc=5:1 to 2:1) to afford the title compound (200 mg, crude) as yellow solid.

LCMS: $(M+H^+)$: 489.0@1.603 min (5-95% ACN in $H_2O$,2 min).

$^1H$ NMR: (400 MHz, CHLOROFORM-d4) δ ppm 8.15-8.04 (m, 1H), 7.41-7.28 (m, 5H), 6.93-6.81 (m, 2H), 6.57 (s, 1H), 5.08 (s, 2H), 4.26-4.14 (m, 2H), 2.52-2.28 (m, 2H), 2.28-2.17 (m, 2H), 2.14-1.83 (m, 2H), 1.29-1.20 (m, 3H), 0.91-0.72 (m, 3H).

Step 4. Synthesis of 4-[2-(2,4-difluoroanilino)thiazol-4-yl]-4-ethoxycarbonyl-hexanoic acid (Cmp. 6)

To a solution of O5-benzyl O1-ethyl 2-[2-(2,4-difluoroanilino)thiazol-4-yl]-2-ethyl-pentanedioate (150 mg, 307.03 umol, 1 eq) in DCM (3 mL) was added $BBr_3$ (230.76 mg, 921.10 umol, 88.75 uL, 3 eq) at 0° C. The mixture was stirred at 0° C. for 1 h. The combined mixture was concentrated and the residue was washed with PE (50 mL) to remove BnBr. The crude product was purified by prep-HPLC (HCl condition) to afford the title compound (20.3 mg, 98.67% purity, HCl salt) as yellow solid.

LCMS: $(M+H^+)$: 399.1@1.868 min (5-100% ACN in $H_2O$, 3 min).

$^1H$ NMR: (400 MHz, METHANOL-d4) δ ppm 8.08 (dt, J=6.0, 9.2 Hz, 1H), 7.11 (ddd, J=2.9, 8.5, 11.3 Hz, 1H), 7.04-6.96 (m, 1H), 6.80 (s, 1H), 4.20 (q, J=7.1 Hz, 2H), 2.41-2.28 (m, 2H), 2.28-2.14 (m, 2H), 2.13-1.97 (m, 2H), 1.28-1.21 (m, 3H), 0.85 (t, J=7.4 Hz, 3H).

Example 7. Synthesis of 4-ethyl-4-[2-(2-methoxyanilino)thiazol-4-yl]hexanoic acid (Cmp. 7 (RS))

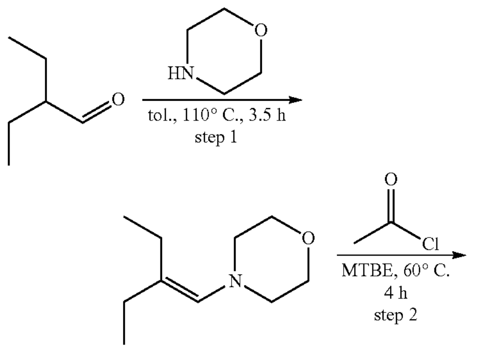

-continued

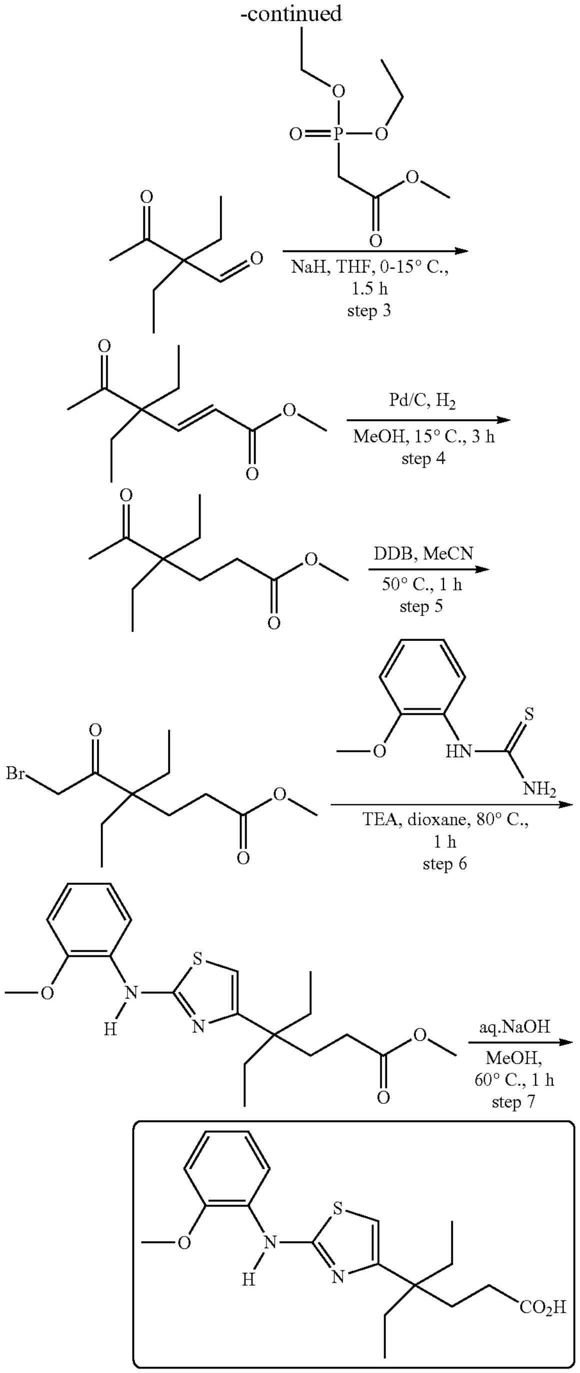

Cmp. 7

Step 1. Synthesis of 4-(2-ethylbut-1-enyl)morpholine

To a mixture of 2-ethylbutanal (20 g, 199.68 mmol, 1 eq), morpholine (17.40 g, 199.68 mmol, 17.57 mL, 1 eq) in toluene (40 mL) was stirred at 110° C. for 3.5 h over a Dean-Stark water separator. The mixture was concentrated to remove the solvent. The concentrated mixture was distilled to obtain the title compound (20 g, 112.25 mmol, 56.21% yield, 95% purity) as a colorless oil and used directly in the next step.

$^1$H NMR: (400 MHz, CHLOROFORM-d) δ ppm 5.27 (s, 1H), 3.74-3.68 (m, 4H), 2.60-2.50 (m, 4H), 2.18 (q, J=7.5 Hz, 2H), 1.95 (q, J=7.5 Hz, 2H), 0.97 (t, J=7.6 Hz, 6H).

Step 2. Synthesis of 2,2-diethyl-3-oxo-butanal

To a solution of 4-(2-ethylbut-1-enyl)morpholine (20 g, 118.16 mmol, 1 eq) in MTBE (30 mL) was added acetyl chloride (18.55 g, 236.32 mmol, 16.86 mL, 2 eq). The mixture was stirred at 60° C. for 4 h, and then it was allowed to cool to the room temperature, the solid was filtered by filtration and washed with MTBE (50 mL). The solid was dissolved in water (200 mL) and the heterogeneous mixture was stirred for 1 h. After extraction with MTBE (100 mL*2), the combined organic layers were washed with saturated aq. $NaHCO_3$(50 mL) and brine (50 mL). The organic layers were dried over anhydrous $Na_2SO_4$ and concentrated under vacuum. The residue was distilled to afford the title compound (3.9 g, 24.68 mmol, 20.89% yield, 90% purity) as a yellow oil.

$^1$H NMR: (400 MHz, CHLOROFORM-d) δ ppm 9.86-9.69 (m, 1H), 2.21-2.15 (m, 3H), 2.07-1.75 (m, 4H), 0.83 (t, J=7.6 Hz, 6H).

Step 3. Synthesis of methyl (E)-4,4-diethyl-5-oxo-hex-2-enoate

To a solution of methyl 2-diethoxyphosphorylacetate (1.77 g, 8.44 mmol, 1.2 eq) in THF (10 mL) was added NaH (421.96 mg, 10.55 mmol, 60% purity, 1.5 eq) at 0° C. After addition, the mixture was stirred at this temperature for 0.5 h, and then 2,2-diethyl-3-oxo-butanal (1 g, 7.03 mmol, 1 eq) was added dropwise at 0° C. The resulting mixture was stirred at 15° C. for 1 h. It was quenched by addition water (50 mL), and then extracted with EtOAc (20 mL*3). The combined organic layers were washed with brine (50 mL), dried over anhydrous $Na_2SO_4$, filtered and concentrated under reduced pressure to give a residue. The residue was purified by column chromatography ($SiO_2$, PE/EtOAc=0/1 to 10:1) to afford the title compound (0.87 g, 4.17 mmol, 59.28% yield, 95% purity) as a colorless oil.

$^1$H NMR: (400 MHz, CHLOROFORM-d) δ ppm 7.01 (d, J=16.3 Hz, 1H), 5.86 (d, J=16.3 Hz, 1H), 3.78-3.67 (m, 3H), 2.11-2.03 (m, 3H), 1.82-1.66 (m, 4H), 0.75 (t, J=7.5 Hz, 6H).

Step 4. Preparation of methyl 4,4-diethyl-5-oxo-hexanoate

To a solution of methyl (E)-4,4-diethyl-5-oxo-hex-2-enoate (0.87 g, 4.39 mmol, 1 eq) in MeOH (10 mL) was added Pd/C (10%, 0.1 g) under $N_2$. The suspension was degassed under vacuum and purged with $H_2$ several times. The mixture was stirred under $H_2$ (15 psi) at 15° C. for 3 h. It was filtered and concentrated to afford the title compound (0.83 g, crude) as a colorless oil and used directly in the next step.

Step 5. Preparation of methyl 6-bromo-4,4-diethyl-5-oxo-hexanoate

To a solution of methyl 4,4-diethyl-5-oxo-hexanoate (0.1 g, 499.32 umol, 1 eq) in ACN (1 mL) was added 1-bromo-1,4-dioxan-1-ium (83.89 mg, 499.32 umol, 1 eq). The mixture was stirred at 50° C. for 1 h. It was cooled to the room temperature and quenched by addition of saturated $NaHCO_3$ solution (50 mL), and extracted with DCM (20 mL*3). The combined organic layers were washed with brine (50 mL), dried over anhydrous $Na_2SO_4$, filtered and concentrated under reduced pressure to afford the title compound (0.15 g, crude) as a yellow oil and used directly in the next step.

$^1$H NMR: (400 MHz, CHLOROFORM-d) δ ppm 4.20-4.10 (m, 1H), 3.69 (d, J=2.0 Hz, 3H), 2.24-2.08 (m, 3H), 2.00-1.83 (m, 2H), 1.72-1.50 (m, 4H), 0.79 (td, J=7.5, 14.4 Hz, 6H).

Step 6. Synthesis of methyl 4-ethyl-4-[2-(2-methoxyanilino)thiazol-4-yl]hexanoate A mixture of methyl 6-bromo-4,4-diethyl-5-oxo-hexanoate (0.13 g, 465.67 umol, 1 eq), (2-methoxyphenyl)thiourea (84.86 mg, 465.67 umol, 1 eq), TEA (94.24 mg, 931.33 umol, 129.63 uL, 2 eq) in dioxane (2 mL) was stirred at 80° C. for 1 h. The mixture was filtered and concentrated under vacuum. The residue was purified by MPLC ($SiO_2$, PE:EtOAc=5:1 to 2:1) to afford the title compound (60 mg, 155.59 umol, 33.41% yield, 94% purity) as colorless oil.

LCMS: ($M+H^+$): 363.2@1.007 min (5-95% ACN in $H_2O$, 2 min).

Step 7. Synthesis of 4-ethyl-4-[2-(2-methoxyanilino)thiazol-4-yl]hexanoic acid (Cmp. 7)

To a solution of methyl 4-ethyl-4-[2-(2-methoxyanilino) thiazol-4-yl]hexanoate (40 mg, 110.35 umol, 1 eq) in MeOH (1 mL) was added NaOH (2 M, 275.87 uL, 5 eq). The mixture was stirred at 60° C. for 1 h. It was cooled to the room temperature. The pH of the mixture was adjusted to 3 with HCl (1 M). The aqueous phase was extracted with EtOAc (10 mL*3). The combined organic phase was washed with brine (10 mL*2), dried over anhydrous $Na_2SO_4$, filtered and concentrated under vacuum. The residue was purified by prep-HPLC (HCl condition) to afford the title compound (8.4 mg, 21.82 umol, 19.78% yield, 100% purity, HCl) as yellow solid.

LCMS: ($M+H^+$): 349.1@2.898 min (1-100% ACN in $H_2O$,4.5 min).

$^1$H NMR: (400 MHz, METHANOL-d4) δ ppm 7.52 (br d, J=7.7 Hz, 1H), 7.41-7.31 (m, 1H), 7.19 (d, J=8.3 Hz, 1H), 7.08 (dt, J=1.2, 7.7 Hz, 1H), 6.64 (s, 1H), 3.92 (s, 3H), 2.24-2.10 (m, 2H), 2.03-1.91 (m, 2H), 1.72 (q, J=7.5 Hz, 4H), 0.81 (t, J=7.5 Hz, 6H).

Example 8. Synthesis of 4-[2-(2-chloroanilino)thiazol-4-yl]-4-ethyl-hexanoic acid (Cmp. 8)

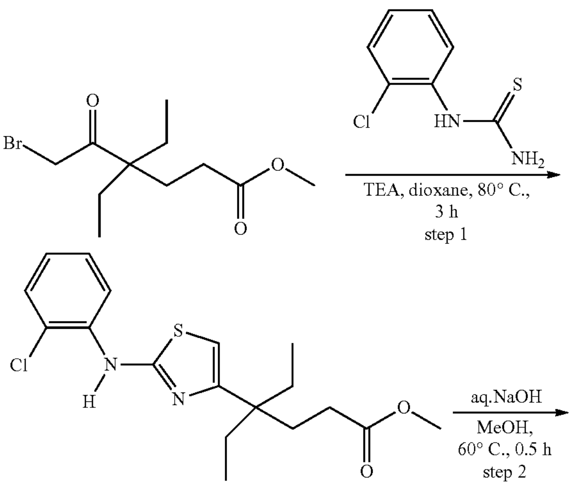

-continued

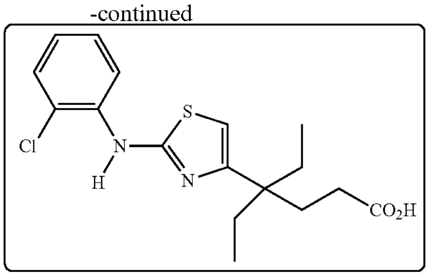

Cmp. 8

Step 1. Synthesis of methyl 4-[2-(2-chloroanilino) thiazol-4-yl]-4-ethyl-hexanoate To a solution of (2-chlorophenyl)thiourea (100.29 mg, 537.31 umol, 1 eq) in dioxane (2 mL) was added methyl 6-bromo-4,4-diethyl-5-oxo-hexanoate (150 mg, 537.31 umol, 1 eq) and TEA (163.11 mg, 1.61 mmol, 224.36 uL, 3 eq). The mixture was stirred at 80° C. for 3 h. The combined mixture was filtered and the filtrate was concentrated under vacuum. The residue was purified by MPLC ($SiO_2$, PE/EtOAc=10/1 to 4:1) to afford the title compound (110 mg 93% purity) as yellow oil.

LCMS: $(M+H^+)$: 367.3@2.980 min (10-80% ACN in $H_2O$, 4.5 min).

Step 2. Synthesis of 4-[2-(2-chloroanilino)thiazol-4-yl]-4-ethyl-hexanoic acid (Cmp. 8)

To a solution of methyl 4-[2-(2-chloroanilino)thiazol-4-yl]-4-ethyl-hexanoate (90 mg, 245.30 umol, 1 eq) in MeOH (3 mL) was added NaOH (2 M, 613.24 uL, 5 eq). The mixture was stirred at 60° C. for 0.5 h. The pH of the mixture was adjusted to 2 with aq. HCl (1M). The mixture was poured into water (10 mL), extracted with EtOAc (3×10 mL), washed with brine, dried over anhydrous $Na_2SO_4$ and concentrated under vacuum. The residue was purified by prep-HPLC (HCl condition) to afford the title compound (18.6 mg, 47.48 umol, 19.36% yield, 99.39% purity, HCl salt) as yellow solid.

LCMS: $(M+H^+)$: 353.1@3.101 min (10-100% ACN in $H_2O$, 4.5 min).

$^1H$ NMR: (400 MHz, DMSO-d6) δ ppm 9.62-9.36 (m, 1H), 8.37-8.23 (m, 1H), 7.48-7.40 (m, 1H), 7.31-7.22 (m, 1H), 7.03-6.93 (m, 1H), 6.57-6.41 (m, 1H), 1.98-1.78 (m, 4H), 1.65-1.50 (m, 4H), 0.75-0.57 (m, 6H).

Example 9. Synthesis of 4-ethyl-4-[2-(3-methoxyanilino)thiazol-4-yl]hexanoic acid (Cmp. 9)

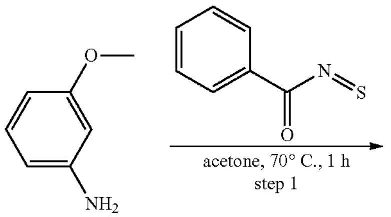

-continued

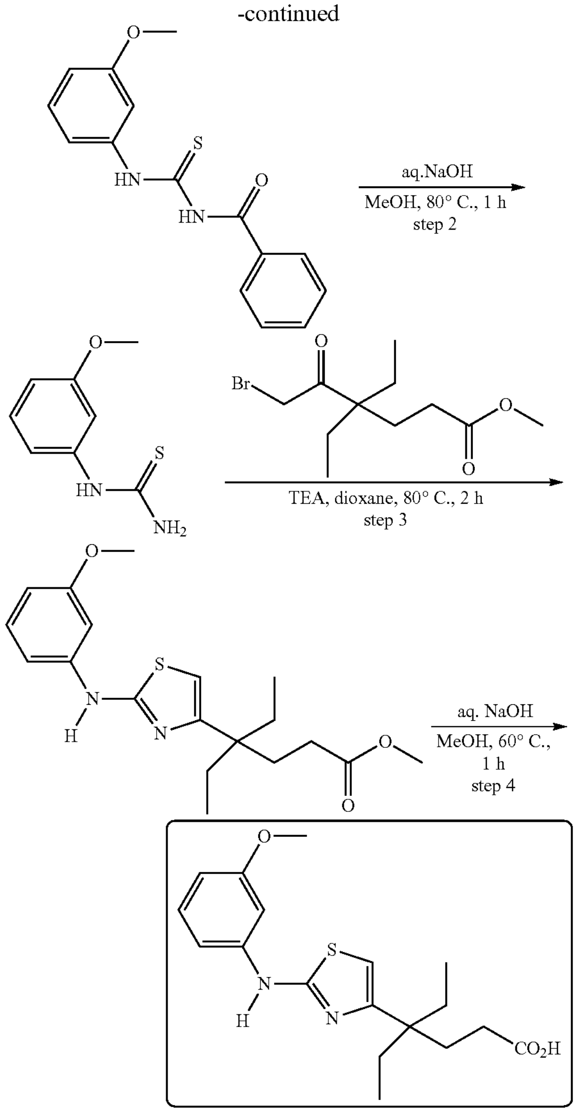

Cmp. 9

Step 1. Synthesis of N-[(3-methoxyphenyl)carbamothioyl]benzamide

To a solution of 3-methoxyaniline (1.66 g, 13.48 mmol, 1.51 mL, 1.1 eq) in acetone (20 mL) was added benzoyl isothiocyanate (2 g, 12.26 mmol, 1.65 mL, 1 eq). The mixture was stirred at 70° C. for 2 h. It was cooled to the room temperature and poured in to water (100 mL). The resulting solid was filtered to afford the title compound (3.5 g, crude) as yellow solid.

Step 2. Synthesis of (3-methoxyphenyl)thiourea

To a solution of N-[(3-methoxyphenyl)carbamothioyl] benzamide (1.5 g, 5.24 mmol, 1 eq) in MeOH (20 mL) was added NaOH (1 M, 15.72 mL, 3 eq). The mixture was stirred at 80° C. for 1 h. It was cooled to the room temperature. The pH of the mixture was adjusted to 2 with aq·HCl (1M), the resulting solid was filtered to afford the title compound as yellow solid.

$^1$H NMR (400 MHz, DMSO-d6) δ ppm 9.70-9.63 (m, 1H), 7.25-7.18 (m, 1H), 7.12-7.08 (m, 1H), 6.93-6.88 (m, 1H), 6.73-6.64 (m, 1H), 3.78-3.66 (m, 3H).

Step 3. Synthesis of methyl 4-ethyl-4-[2-(3-methoxyanilino)thiazol-4-yl]hexanoate To a solution of (3-methoxyphenyl)thiourea (97.92 mg, 537.31 umol, 1 eq) in dioxane (2 mL) was added methyl 6-bromo-4,4-diethyl-5-oxo-hexanoate (150 mg, 537.31 umol, 1 eq) and TEA (163.11 mg, 1.61 mmol, 224.36 uL, 3 eq). The mixture was stirred at 80° C. for 2 h. The combined mixture was filtered and concentrated under vacuum. The residue was purified by column chromatography ($SiO_2$, PE:EtOAc=5:1 to 2:1) to afford the title compound (70 mg, 97% purity) as yellow oil.

LCMS: (M−$H^+$): 363.2@1.039 min (5-95% ACN in $H_2O$, 2 min).

Step 4. Synthesis of 4-ethyl-4-[2-(3-methoxyanilino)thiazol-4-yl]hexanoic acid (Cmp. 9)

To a solution of methyl 4-ethyl-4-[2-(3-methoxyanilino)thiazol-4-yl]hexanoate (50 mg, 137.94 umol, 1 eq) in MeOH (2 mL) was added NaOH (2 M, 344.84 uL, 5 eq). The mixture was stirred at 60° C. for 1 h. The pH of the mixture was adjusted to 2 with aq. HCl (1M). The mixture was poured into water (10 mL), extracted with EtOAc (3×10 mL), washed with brine (3×10 mL), dried over anhydrous $Na_2SO_4$ and concentrated under vacuum. The residue was purified by prep-HPLC (HCl condition) to afford the title compound (9.6 mg, 99.13% purity, HCl salt) as white solid.

LCMS: (M+$H^+$):349.2@3.018 min (1-100% ACN in $H_2O$, 4.5 min).

$^1$H NMR: (400 MHz, METHANOL-d4) δ ppm 7.42 (t, J=8.2 Hz, 1H), 7.07 (br d, J=2.2 Hz, 1H), 7.05-7.01 (m, 1H), 6.98-6.92 (m, 1H), 6.65 (d, J=2.1 Hz, 1H), 3.84 (s, 3H), 2.23-2.13 (m, 2H), 2.05-1.93 (m, 2H), 1.74 (q, J=7.4 Hz, 4H), 0.82 (t, J=7.5 Hz, 6H).

Example 10. Synthesis of 4-ethyl-4-[2-(2-hydroxyanilino)-5-methyl-thiazol-4-yl]hexanoic acid (Cmp. 10)

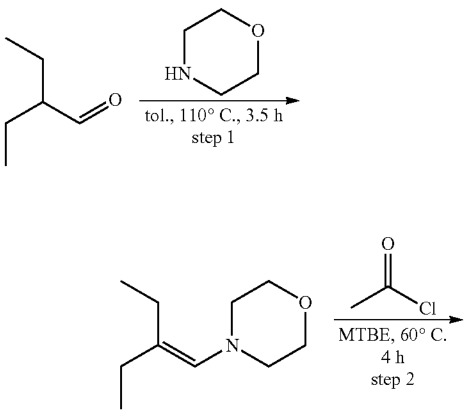

-continued

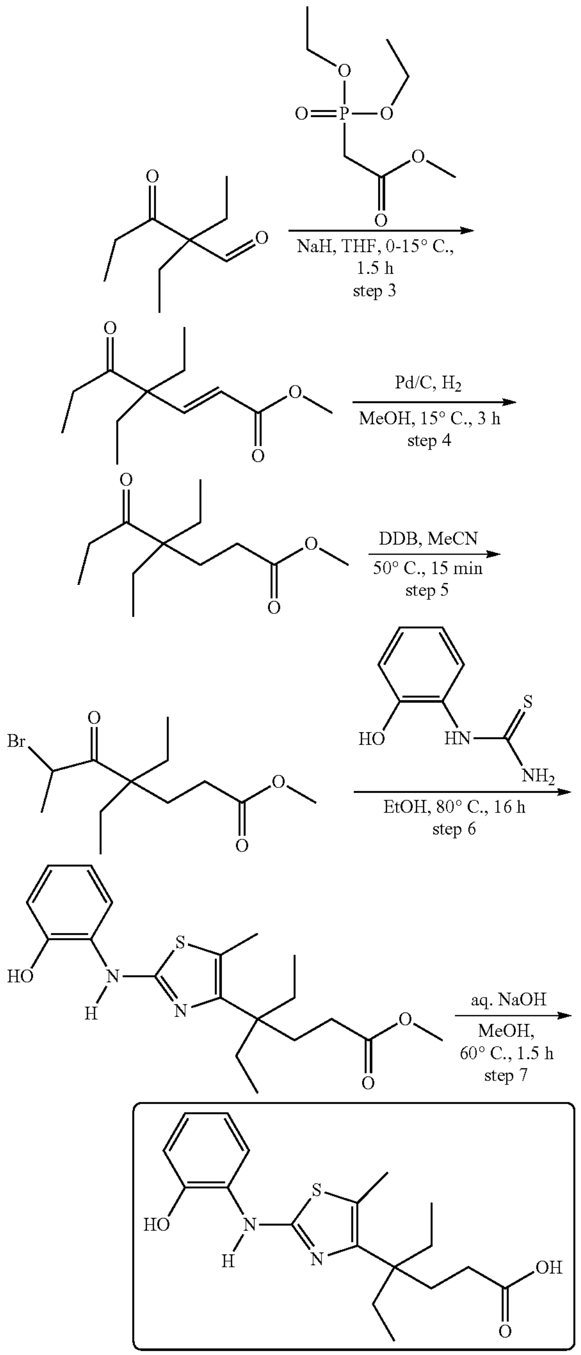

Cmp. 10

Step 1. Synthesis of 4-(2-ethylbut-1-enyl)morpholine

A mixture of 2-ethylbutanal (10 g, 99.84 mmol, 1 eq), morpholine (8.70 g, 99.84 mmol, 8.79 mL, 1 eq) in Toluene (40 mL) was stirred at 110° C. for 3.5 h over a Dean-Stark water separator. The mixture was concentrated to remove the solvent. The desired product (10 g, 56.13 mmol, 56.21% yield, 95% purity) as colorless oil was obtained by distillation. It was used in next step directly.

Step 2. Synthesis of 2,2-diethyl-3-oxo-pentanal

To a solution of 4-(2-ethylbut-1-enyl) morpholine (2 g, 11.82 mmol, 1 eq) in MTBE (5 mL) was added propionyl chloride (2.19 g, 23.63 mmol, 2.19 mL, 2 eq). The mixture was stirred at 60° C. for 4 h. A brown solid precipitated and the mixture became pasty. After cooling to room temperature, the solid was filtered and washed with MTBE (50 mL). The solid was dissolved in water (200.0 mL) and the heterogeneous mixture was stirred for 1 h. After extraction with MTBE (100 mL*2), the combined organic layers were washed with saturated aq. $NaHCO_3$ (50 mL) and brine (50 mL). The organic layers were dried over anhydrous $Na_2SO_4$ and concentrated. The residue was purified by column chromatography ($SiO_2$, Petroleum ether/Ethyl acetate=50/1 to 10/1) to afford the title compound (0.46 g, 2.80 mmol, 23.67% yield, 95% purity) as a yellow oil.

$^1H$ NMR: (400 MHz, CHLOROFORM-d) δ ppm 9.82-9.64 (m, 1H), 2.55-2.39 (m, 2H), 2.02-1.80 (m, 4H), 1.10-1.01 (m, 3H), 0.80 (t, J=7.6 Hz, 6H).

Step 3. Synthesis of Methyl (E)-4,4-diethyl-5-oxo-hept-2-enoate

To a solution of methyl 2-diethoxyphosphorylacetate (742.60 mg, 3.53 mmol, 1.2 eq) in THF (10 mL) was added portion wise NaH (176.67 mg, 4.42 mmol, 60% purity, 1.5 eq) at 0° C. After addition, the mixture was stirred at this temperature for 0.5 h, and then 2,2-diethyl-3-oxo-pentanal (0.46 g, 2.94 mmol, 1 eq) was added dropwise at 0° C. The resulting mixture was stirred at 15° C. for 1 h. The reaction mixture was quenched by addition water (50 mL), and then extracted with EtOAc (20 mL*3). The combined organic layers were washed with brine (50 mL), dried over anhydrous $Na_2SO_4$, filtered and concentrated under reduced pressure to give a residue. The residue was purified by column chromatography ($SiO_2$, Petroleum ether/Ethyl acetate=0/1 to 10:1) to afford the title compound (0.32, 1.36 mmol, 46.07% yield, 90% purity) as a colorless oil.

Step 4. Synthesis of Methyl 4,4-diethyl-5-oxo-heptanoate

To a solution of methyl (E)-4,4-diethyl-5-oxo-hept-2-enoate (0.32 g, 1.51 mmol, 1 eq) in MeOH (20 mL) was added Pd/C (0.05 g, 10% purity) under $N_2$. The suspension was degassed under vacuum and purged with $H_2$ several times. The mixture was stirred under $H_2$ (15 psi) at 15° C. for 3 h. It was filtered and concentrated to afford the title compound (0.18 g, crude) as colorless oil.

$^1H$ NMR: (400 MHz, CHLOROFORM-d) δ ppm 3.66 (s, 3H), 2.44 (q, J=7.1 Hz, 2H), 2.17-2.01 (m, 2H), 1.95-1.78 (m, 2H), 1.58 (q, J=7.5 Hz, 4H), 1.02 (t, J=7.2 Hz, 3H), 0.73 (t, J=7.5 Hz, 6H).

Step 5. Synthesis of Methyl 6-bromo-4,4-diethyl-5-oxo-heptanoate

To a solution of methyl 4,4-diethyl-5-oxo-heptanoate (0.16 g, 746.62 umol, 1 eq) in ACN (2 mL) was added 1-bromo-1,4-dioxan-1-ium; bromide (185.10 mg, 746.62 umol, 1 eq). The mixture was stirred at 50° C. for 15 min. The reaction mixture was quenched by addition saturated $NaHCO_3$ solution 50 mL, and extracted with DCM (20 mL*3). The combined organic layers were washed with brine (50 mL), dried over anhydrous $Na_2SO_4$, filtered and concentrated under reduced pressure to give a residue to afford the title compound (0.18 g, crude) as brown oil which was used in next step directly without further purification.

Step 6. Synthesis of Methyl 4-ethyl-4-[2-(2-hydroxyanilino)-5-methyl-thiazol-4-yl]hexanoate A mixture of methyl 6-bromo-4,4-diethyl-5-oxo-heptanoate (0.1 g, 341.07 umol, 1 eq) and (2-hydroxyphenyl) thiourea (68.85 mg, 409.28 umol, 1.2 eq) in EtOH (3 mL) was stirred at 80° C. for 16 h. It was concentrated under vacuum. The residue was purified by silica gel chromatography (100-200 mesh silica gel, Petroleum ether/Ethyl acetate=10/1, 2/1) to afford the title compound (40 mg) as yellow oil.

Step 7. Synthesis of 4-ethyl-4-[2-(2-hydroxyanilino)-5-methyl-thiazol-4-yl]hexanoic acid (Cmp. 10)

A mixture of methyl 4-ethyl-4-[2-(2-hydroxyanilino)-5-methyl-thiazol-4-yl]hexanoate (0.04 g, 110.35 umol, 1 eq) and NaOH (2 M, 275.87 uL, 5 eq) in MeOH (2 mL) was stirred at 60° C. for 1.5 h. It was diluted with water (30 mL), extracted with ethyl acetate (30 mL*2). The combined organic phase was discarded. The aqueous phase pH was adjusted to 5 with aq. HCl (2 N), and extracted with ethyl acetate (20 mL*3). The combined organic phase was dried over anhydrous $Na_2SO_4$, filtered and concentrated under vacuum. The residue was purified by prep-HPLC (HCl condition) to afford the title compound (7.5 mg, 18.90 umol, 17.13% yield, 97% purity, HCl) as yellow solid.

LCMS: (M+H$^+$): 349.2@2.215 min (10-100% ACN in $H_2O$, 4.5 min).

$^1H$ NMR: (400 MHz, METHANOL-d4) δ ppm 7.37 (dd, J=1.4, 7.9 Hz, 1H), 7.28-7.15 (m, 1H), 7.05-6.92 (m, 2H), 2.42 (s, 3H), 2.32-2.19 (m, 2H), 2.12-2.01 (m, 2H), 1.82 (q, J=7.4 Hz, 4H), 0.88 (t, J=7.4 Hz, 6H).

Example 11. Synthesis of 4-[6-(2,4-difluoroanilino) pyrazin-2-yl]-4-ethoxycarbonyl-hexanoic acid (Cmp. 11 (RS))

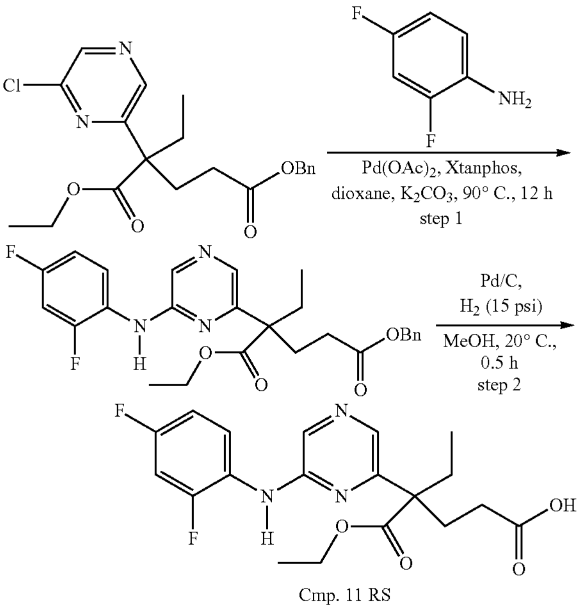

Cmp. 11 RS

Step 1. Synthesis of O5-benzyl O1-ethyl 2-[6-(2,4-difluoroanilino)pyrazin-2-yl]-2-ethyl-pentanedioate To a solution of O5-benzyl O1-ethyl 2-(6-chloropyrazin-2-yl)-2-ethyl-pentanedioate (300 mg, 767.54 umol, 1 eq) in dioxane (3 mL) was added 2,4-difluoroaniline (123.87 mg, 959.42 umol, 1.25 eq), Xantphos (111.03 mg, 191.88 umol, 0.25 eq), $K_2CO_3$ (318.24 mg, 2.30 mmol, 3 eq) and $Pd(OAc)_2$ (17.23 mg, 76.75 umol, 0.1 eq). The mixture was stirred at 90° C. for 12 h under $N_2$. It was cooled to the room temperature and poured into water (15 mL), extracted with EtOAc (3×15 mL), washed with brine (3×15 mL), dried over anhydrous $Na_2SO_4$ and concentrated. The residue was purified by MPLC ($SiO_2$, PE:EtOAc=10/1 to 2/1) to afford the title compound (280 mg, 306.92 umol, 39.99% yield, 53% purity) as brown oil.

LCMS: $(M+H^+)$: 484.2@1.273 min (5-95% ACN in $H_2O$, 2 min).

Step 2. Synthesis of 4-[6-(2,4-difluoroanilino)pyrazin-2-yl]-4-ethoxycarbonyl-hexanoic acid (Cmp. 11)

To a solution of O5-benzyl O1-ethyl 2-[6-(2,4-difluoroanilino)pyrazin-2-yl]-2-ethyl-pentanedioate (330 mg, 682.51 umol, 1 eq) in MeOH (5 mL) was added Pd/C (0.1 g, 10% purity) under $N_2$. The suspension was degassed under vacuum and purged with $H_2$ several times. The mixture was stirred at 20° C. for 0.5 h under $H_2$ (15 psi). The mixture was filtered and the filtrate was concentrated. The residue was purified by prep-HPLC (HCl condition) to afford the title compound (46 mg, 97.27% purity, HCl salt) as yellow solid.

LCMS: $(M+H^+)$: 394.1@2.991 min (1-100% ACN in $H_2O$, 4.5 min).

$^1H$ NMR: (400 MHz, METHANOL-d4) δ ppm 8.13-8.03 (m, 2H), 7.91 (s, 1H), 7.01 (ddd, J=2.9, 8.5, 11.3 Hz, 1H), 6.95-6.83 (m, 1H), 4.20-4.07 (m, 2H), 2.45-2.24 (m, 2H), 2.19-2.03 (m, 4H), 1.14 (t, J=7.1 Hz, 3H), 0.82 (t, J=7.4 Hz, 3H).

Example 12. Synthesis of (4R)-4-[2-(2,4-dichloroanilino)thiazol-4-yl]-4-ethoxycarbonyl-hexanoic acid (Cmp. 12a) and (4s)-4-[2-(2,4-dichloroanilino)thiazol-4-yl]-4-ethoxycarbonyl-hexanoic acid (Cmp. 12b)

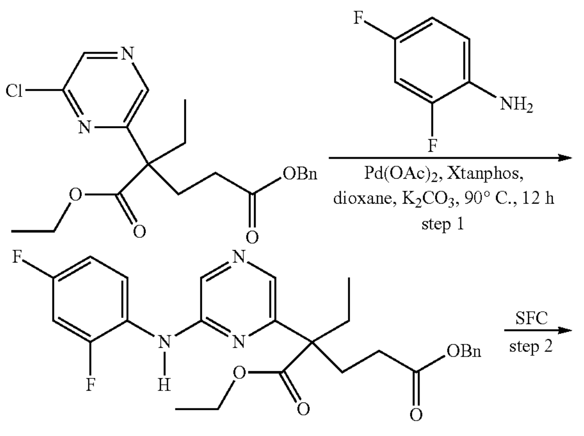

-continued

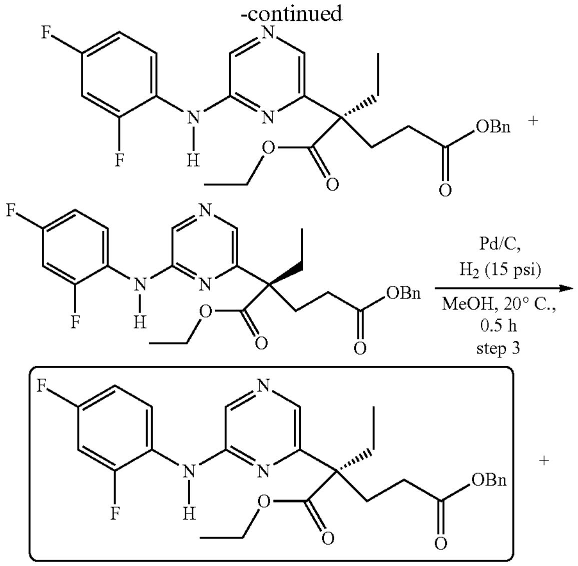

Cmp. 12a, temporary assignment

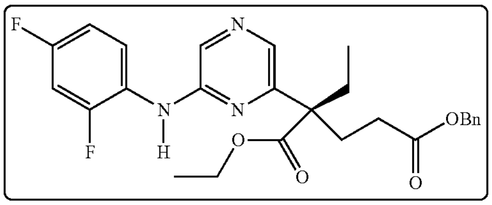

Cmp. 12b, temporary assignment

Step 1. Synthesis of O5-benzyl O1-ethyl(2R)-2-[6-(2,4-difluoroanilino)pyrazin-2-yl]-2-ethyl-pentanedioate and O5-benzyl O1-ethyl(2S)-2-[6-(2,4-difluoroanilino)pyrazin-2-yl]-2-ethyl-pentanedioate To a solution of O5-benzyl O1-ethyl 2-(6-chloropyrazin-2-yl)-2-ethyl-pentanedioate (400 mg, 1.02 mmol, 1 eq) in dioxane (3 mL) was added 2,4-difluoroaniline (165.16 mg, 1.28 mmol, 1.25 eq), Xantphos (148.04 mg, 255.85 umol, 0.25 eq), $K_2CO_3$ (424.31 mg, 3.07 mmol, 3 eq) and $Pd(OAc)_2$ (22.98 mg, 102.34 umol, 0.1 eq). The mixture was stirred at 90° C. for 12 h under $N_2$. It was poured into water (15 mL), extracted with EtOAc (15 mL*3), washed with brine (15 mL*3), dried over anhydrous $Na_2SO_4$ and concentrated. The residue was purified by MPLC ($SiO_2$, PE:EtOAc=10/1 to 2/1) to obtain the racemic product (360 mg, 90% purity). It was separated by SFC (column: DAICEL CHIRALPAK IC (250 mm*30 mm, 10 uM); mobile phase: [0.1% $NH_3H_2O$ IPA]; B %: 40%-40%, 5 min) to afford the title compound peak 1 (P1): (170 mg, 315.74 umol, 30.85% yield, 89.8% purity, 99.22% ee, Rt=3.485 min) as yellow solid; peak 2 (P2): (150 mg, 282.31 umol, 27.59% yield, 91% purity, 99.22% ee, Rt=4.102 min) as yellow solid.

P1: HPLC: (10-80% ACN in $H_2O$, 4.5 min), SFC: Rt=3.485 min

P2: HPLC: (10-80% ACN in $H_2O$, 4.5 min), SFC: Rt=4.102 min

Step 2. Synthesis of (4R)-4-[6-(2,4-difluoroanilino)pyrazin-2-yl]-4-ethoxycarbonyl-hexanoic acid (Cmp. 12a)

To a solution of O5-benzyl O1-ethyl(2R)-2-[6-(2,4-difluoroanilino)pyrazin-2-yl]-2-ethyl-pentanedioate (170.00 mg, 351.60 umol, 1 eq) in MeOH (5 mL) was added Pd/C (0.1 g, 10% purity) under $N_2$. The suspension was degassed under vacuum and purged with $H_2$ several times. The mixture was stirred at 20° C. for 0.5 h under $H_2$ (15 psi). The mixture was filtered and the filtrate was concentrated. The residue was purified by prep-HPLC (HCl condition) to afford the title compound (44.7 mg, 100.76 umol, 28.66% yield, 96.89% purity, HCl salt, 98.32% ee, Rt=2.682 min) as yellow solid.

LCMS: $(M+H^+)$: 394.1@2.738 min (0-100% ACN in $H_2O$, 4.5 min).

$^1H$ NMR: (400 MHz, METHANOL-d4) δ ppm 8.12 (s, 1H), 8.07-7.94 (m, 2H), 7.10-7.00 (m, 1H), 6.95 (br t, J=8.6 Hz, 1H), 4.14 (q, J=6.8 Hz, 2H), 2.46-2.26 (m, 2H), 2.19-2.06 (m, 4H), 1.16 (t, J=7.2 Hz, 3H), 0.83 (t, J=7.4 Hz, 3H).

SFC: Rt=2.682 min

Step 3. Synthesis of (4S)-4-[6-(2,4-difluoroanilino) pyrazin-2-yl]-4-ethoxycarbonyl-hexanoic acid (Cmp. 12b)

To a solution of O5-benzyl O1-ethyl(2S)-2-[6-(2,4-difluoroanilino)pyrazin-2-yl]-2-ethyl-pentanedioate (150.00 mg, 310.23 umol, 1 eq) in MeOH (5 mL) was added Pd/C (0.1 g, 10% purity) under $N_2$. The suspension was degassed under vacuum and purged with $H_2$ several times. The mixture was stirred at 20° C. for 0.5 h under $H_2$ (15 psi). The mixture was filtered and the filtrate was concentrated. The residue was purified by prep-HPLC (HCl condition) to afford the title compound (43.5 mg, 100.08 umol, 32.26% yield, 98.89% purity, HCl salt, 97.54% ee, Rt=2.579 min) as yellow solid.

LCMS: $(M+H^+)$: 394.2@2.735 min (0-100% ACN in $H_2O$, 4.5 min).

$^1H$ NMR: (400 MHz, METHANOL-d4) δ ppm 8.13 (s, 1H), 8.07-7.92 (m, 2H), 7.07 (ddd, J=2.8, 8.6, 11.1 Hz, 1H), 7.00-6.93 (m, 1H), 4.15 (q, J=7.1 Hz, 2H), 2.46-2.27 (m, 2H), 2.23-2.06 (m, 4H), 1.17 (t, J=7.2 Hz, 3H), 0.83 (t, J=7.4 Hz, 3H).

SFC: Rt=2.579 min.

Example 13. Synthesis of 4-ethoxycarbonyl-4-[2-(4-methylanilino)pyrimidin-4-yl]hexanoic acid (Cmp. 13)

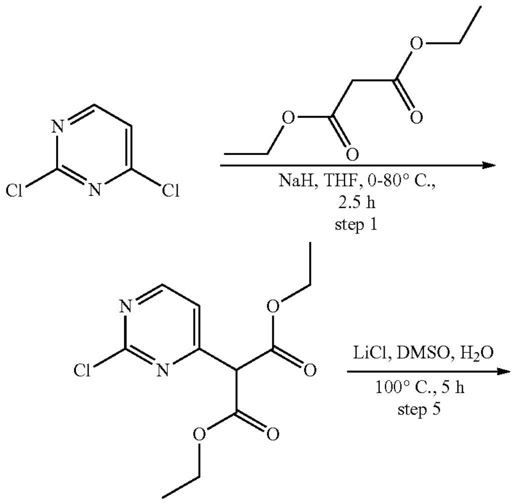

-continued

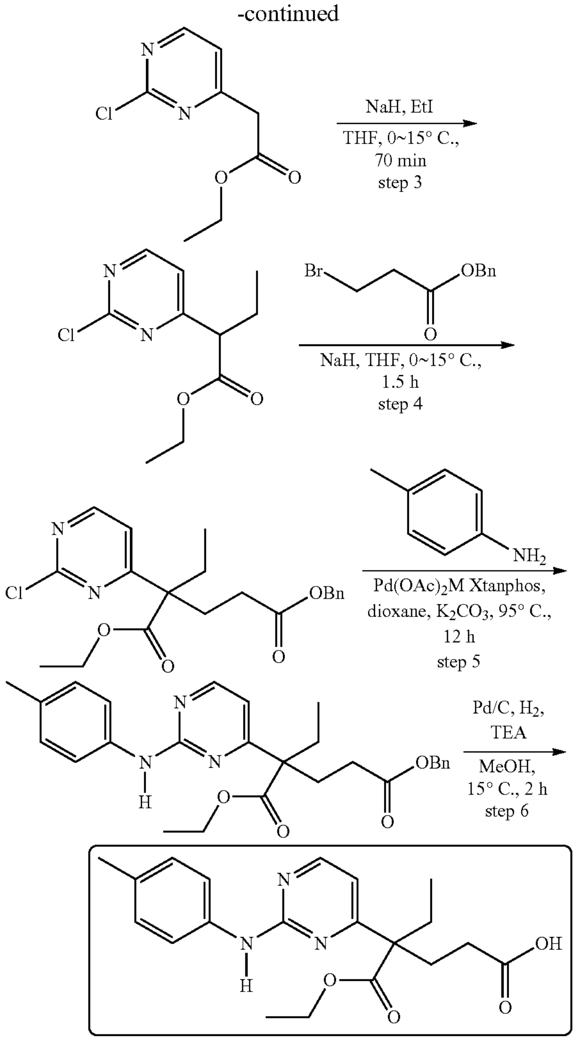

Cmp. 13, RS

Step 1. Synthesis of Diethyl 2-(2-chloropyrimidin-4-yl) propanedioate

To a solution of diethyl propanedioate (4.84 g, 30.21 mmol, 4.56 mL, 1.5 eq) in THF (50 mL) was added NaH (2.42 g, 60.41 mmol, 60% purity, 3 eq) at 0° C., the mixture was stirred at 0° C. for 0.5 h. Then 2,4-dichloropyrimidine (3 g, 20.14 mmol, 1 eq) in THF (10 mL) was added to the above mixture and the resulting mixture was stirred at 80° C. for 2 h. It was quenched with Sat. $NH_4Cl$ solution (30 mL), the aqueous phase was extracted with ethyl acetate (30 mL*2). The combined organic phase was washed with brine (30 mL*2), dried over anhydrous $Na_2SO_4$, filtered and concentrated under vacuum. The residue was purified by silica gel chromatography (100-200 mesh silica gel, Petroleum ether/Ethyl acetate=10/1, 3/1) to afford the title compound (4.5 g, 15.68 mmol, 77.85% yield, 95% purity) as yellow oil.

Step 2. Synthesis of Ethyl 2-(2-chloropyrimidin-4-yl)acetate

A mixture of diethyl 2-(2-chloropyrimidin-4-yl) propanedioate (1 g, 3.67 mmol, 1 eq), $H_2O$ (6.61 mg, 366.72 umol, 6.61 uL, 0.1 eq) and LiCl (621.88 mg, 14.67 mmol, 300.42 uL, 4 eq) in DMSO (5 mL) was stirred at 100° C. for 5 h. It was poured into water (20 mL). The aqueous phase was extracted with ethyl acetate (20 mL*3). The combined organic phase was washed with brine (30 mL*2), dried over anhydrous $Na_2SO_4$, filtered and concentrated under vacuum. The residue was purified by silica gel chromatography (100-200 mesh silica gel, Petroleum ether/Ethyl acetate=10/1, 3/1) to afford the title compound (0.46 g, 1.97 mmol, 53.77% yield, 86% purity) as yellow oil.

LCMS: $(M+H^+)$: 201.2@0.881 min (5-95% ACN in $H_2O$, 2.0 min).

Step 3. Synthesis of Ethyl 2-(2-chloropyrimidin-4-yl) butanoate

A mixture of ethyl 2-(2-chloropyrimidin-4-yl)acetate (0.36 g, 1.44 mmol, 1 eq) in DMF (5 mL) was added NaH (63.16 mg, 1.58 mmol, 60% purity, 1.1 eq) at 0° C. After addition, the mixture was stirred at 0° C. for 10 min, then ethyl iodide (235.09 mg, 1.51 mmol, 120.56 uL, 1.05 eq) was added to the above mixture and the resulting mixture was stirred at 15° C. for 1 h. It was quenched with water (30 mL), the aqueous phase was extracted with ethyl acetate (20 mL*3). The combined organic phase was washed with brine (30 mL*2), dried over anhydrous $Na_2SO_4$, filtered and concentrated under vacuum. The residue was purified by silica gel chromatography (100-200 mesh silica gel, Petroleum ether/Ethyl acetate=10/1, 3/1) to afford the title compound (0.3 g) as yellow oil.

Step 4. Synthesis of O5-benzyl O1-ethyl 2-(2-chloropyrimidin-4-yl)-2-ethyl-pentanedioate To a solution of ethyl 2-(2-chloropyrimidin-4-yl) butanoate (0.28 g, 1.22 mmol, 1 eq) in THF (8 mL) was added NaH (63.67 mg, 1.59 mmol, 60% purity, 1.3 eq) at 0° C. After the reaction was stirred at 0° C. for 0.5 h, benzyl 3-bromopropanoate (327.42 mg, 1.35 mmol, 1.1 eq) was added to the above mixture and it was stirred at 15° C. for additional 1 h. It was quenched with Sat. $NH_4Cl$ solution (20 mL), the aqueous phase was extracted with ethyl acetate (20 mL*3). The combined organic phase was washed with brine (25 mL*2), dried over anhydrous $Na_2SO_4$, filtered and concentrated under vacuum. The residue was purified by silica gel chromatography (100-200 mesh silica gel, Petroleum ether/Ethyl acetate=10/1, 3/1) to afford the title compound (0.35 g, 796.96 umol, 65.09% yield, 89% purity) as yellow oil.

$^1H$ NMR: (400 MHz, METHANOL-d4) δ ppm 8.62 (d, J=5.3 Hz, 1H), 7.48 (d, J=5.3 Hz, 1H), 7.41-7.21 (m, 4H), 5.06 (s, 2H), 4.25-4.10 (m, 2H), 2.54-2.32 (m, 2H), 2.30-2.20 (m, 2H), 2.10 (q, J=7.5 Hz, 2H), 1.24-1.12 (m, 3H), 0.80 (t, J=7.5 Hz, 3H).

Step 5. Synthesis of O5-benzyl O1-ethyl 2-ethyl-2-[2-(4-methylanilino)pyrimidin-4-yl]pentanedioate To a solution of O5-benzyl O1-ethyl 2-(2-chloropyrimidin-4-yl)-2-ethyl-pentanedioate (0.31 g, 793.12 umol, 1 eq) and 4-methylaniline (127.48 mg, 1.19 mmol, 131.02 uL, 1.5 eq) in dioxane (10 mL) was added $K_2CO_3$ (219.23 mg, 1.59 mmol, 2 eq), $Pd(OAc)_2$ (17.81 mg, 79.31 umol, 0.1 eq) and Xantphos (91.78 mg, 158.62 umol, 0.2 eq). The mixture was stirred at 95° C. under $N_2$ atmosphere for 12 h. It was poured into water (30 mL). The mixture was separated and the aqueous phase was extracted with ethyl acetate (30 mL*3). The combined organic phase was washed with brine (50 mL*2), dried over anhydrous $Na_2SO_4$, filtered and concentrated under vacuum. The residue was purified by silica gel chromatography (100-200 mesh silica gel, Petroleum ether/Ethyl acetate=10/1, 3/1) to afford the title compound (0.23 g, 97% purity) as yellow oil.

LCMS: $(M+H^+)$: 462.4@1.346 min (5-95% ACN in $H_2O$, 2.0 min).

Step 6. Synthesis of 4-ethoxycarbonyl-4-[2-(4-methylanilino)pyrimidin-4-yl]hexanoic acid (Cmp. 13)

To a solution of O5-benzyl O1-ethyl 2-ethyl-2-[2-(4-methylanilino)pyrimidin-4-yl]pentanedioate (0.2 g, 433.32 umol, 1 eq) and TEA (131.54 mg, 1.30 mmol, 180.94 uL, 3 eq) in MeOH (5 mL) was added Pd/C (0.02 g, 10% purity) under $N_2$. The suspension was degassed under vacuum and purged with $H_2$ several times. The mixture was stirred under $H_2$ (15 psi) at 15° C. for 2 h. The reaction mixture was filtered and the filtrate was concentrated. The residue was purified by prep-HPLC (HCl) to afford the title compound (78.1 mg, 98.94% purity, as a HCl salt) as yellow solid.

LCMS: $(M+H^+)$: 372.1@2.794 min (10-100% ACN in $H_2O$, 4.5 min).

1H NMR: (400 MHz, METHANOL-d4) δ ppm 8.30 (d, J=5.6 Hz, 1H), 7.47 (d, J=8.3 Hz, 2H), 7.15 (d, J=8.3 Hz, 2H), 6.86 (d, J=5.6 Hz, 1H), 4.24-4.10 (m, 2H), 2.44-2.34 (m, 2H), 2.36-2.28 (m, 3H), 2.20 (ddd, J=4.0, 6.2, 9.9 Hz, 2H), 2.11 (q, J=7.5 Hz, 2H), 1.19 (t, J=7.1 Hz, 3H), 0.85 (t, J=7.5 Hz, 3H).

Example 14. Synthesis of 4-[2-(2,4-dichloroanilino)thiazol-4-yl]-4-ethoxycarbonyl-hexanoic acid (Cmp. 14a (RS)) and 4-[5-Bromo-2-(2,4-dichloroanilino)thiazol-4-yl]-4-ethoxycarbonyl-hexanoic acid (Cmp. 14b (RS))

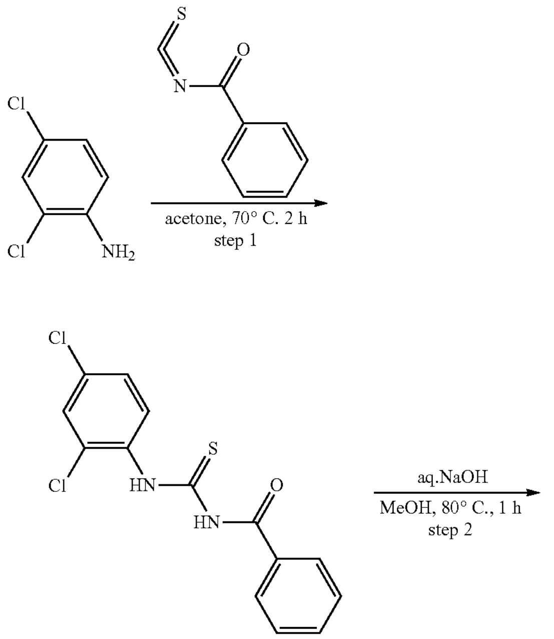

-continued

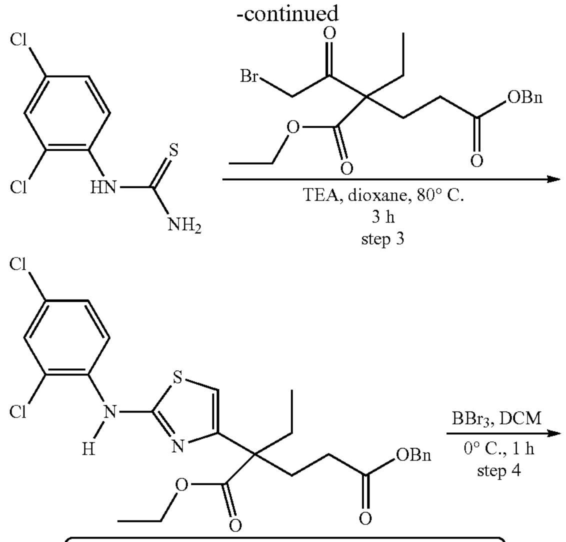

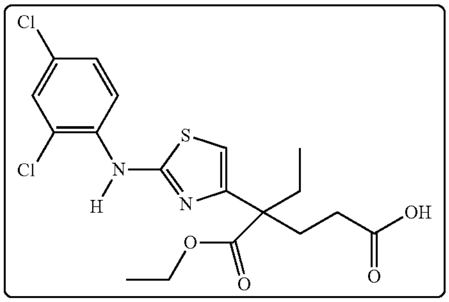

Cmp. 14a

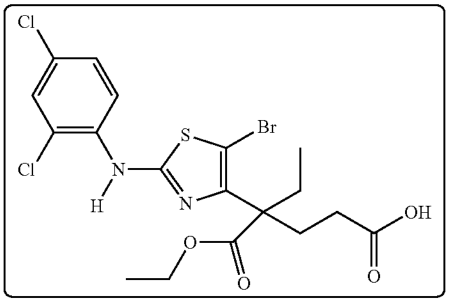

Cmp. 14b

Step 1. Synthesis of N-[(2,4-dichlorophenyl)carbamothioyl]benzamide

To a solution of benzoyl isothiocyanate (1.11 g, 6.79 mmol, 915.71 uL, 1.1 eq) in acetone (20 mL) was added 2,4-dichloroaniline (1.00 g, 6.17 mmol, 1 eq). The mixture was stirred at 70° C. for 2 h. It was cooled to the room temperature and poured into water (100 mL). The yellow solid formed. It was filtered to afford the title compound (3 g, crude) as yellow solid and used directly for the next step.

Step 2. Synthesis of (2,4-dichlorophenyl)thiourea

To a solution of N-[(2,4-dichlorophenyl)carbamothioyl] benzamide (3 g, 9.22 mmol, 1 eq) in MeOH (30 mL) was added NaOH (1 M, 27.67 mL, 3 eq). The mixture was stirred at 80° C. for 1 h. It was cooled to the room temperature and poured into water (30 mL) and adjusted pH to 2 with HCl (1M), extracted with EtOAc (3×30 mL). The combined organic layers were washed with brine (3×30 mL), dried over anhydrous $Na_2SO_4$ and concentrated to afford the title compound (1.6 g, crude) as yellow solid and used directly next step.

Step 3. Synthesis of O5-benzyl O1-ethyl 2-[2-(2,4-dichloroanilino)thiazol-4-yl]-2-ethyl-pentanedioate To a solution of O5-benzyl O1-ethyl 2-(2-bromoacetyl)-2-ethyl-pentanedioate (500 mg, 1.25 mmol, 1 eq) in dioxane (5 mL) was added (2,4-dichlorophenyl)thiourea (276.89 mg, 1.25 mmol, 1 eq) and TEA (380.15 mg, 3.76 mmol, 522.90 uL, 3 eq). The mixture was stirred at 80° C. for 3 h. The mixture was filtered and the filtrate was concentrated. The residue was purified by MPLC ($SiO_2$, PE:EtOAc=20/1 to 4/1) to afford the title compound (250 mg, 345.19 umol, 27.57% yield, 72% purity) as yellow oil.

LCMS: $(M+H^+)$:521.2@3.011 min (5-95% ACN in $H_2O$, 4.5 min).

Step 4. Synthesis of 4-[2-(2,4-dichloroanilino)thiazol-4-yl]-4-ethoxycarbonyl-hexanoic acid (Cmp. 14a, (RS))

To a solution of O5-benzyl O1-ethyl 2-[2-(2,4-dichloroanilino)thiazol-4-yl]-2-ethyl-pentanedioate (200 mg, 383.54 umol, 1 eq) in DCM (5 mL) was added $BBr_3$ (288.26 mg, 1.15 mmol, 110.87 uL, 3 eq) at 0° C. The mixture was stirred at 0° C. for 1 h. It was concentrated and washed with PE (100 mL). The residue dissolved in ACN (20 mL) and adjusted to pH to 9 with $NH_3.H_2O$ (25%). The residue was purified by prep-HPLC (neutral condition) to afford the title compound (24.8 mg, 98.75% purity) as yellow solid.

LCMS: $(M+H^+)$: 431.0@3.209 min (10-100% ACN in $H_2O$, 4.5 min).

$^1H$ NMR: (400 MHz, METHANOL-d4) δ ppm 8.42 (d, J=8.9 Hz, 1H), 7.44 (d, J=2.4 Hz, 1H), 7.27 (dd, J=2.4, 8.9 Hz, 1H), 6.76 (s, 1H), 4.18 (q, J=7.1 Hz, 2H), 2.43-2.28 (m, 2H), 2.14-2.02 (m, 4H), 1.24 (t, J=7.1 Hz, 3H), 0.83 (t, J=7.4 Hz, 3H).

Step 5. Synthesis of 4-[5-bromo-2-(2,4-dichloroanilino)thiazol-4-yl]-4-ethoxycarbonyl-hexanoic acid (Cmp. 14b, (RS))

To a solution of O5-benzyl O1-ethyl 2-[2-(2,4-dichloroanilino)thiazol-4-yl]-2-ethyl-pentanedioate (110 mg, 210.95 umol, 1 eq) in DCM (5 mL) was added $BBr_3$ (158.54 mg, 632.84 umol, 60.98 uL, 3 eq) at 0° C. The mixture was stirred at 0° C. for 1 h. The mixture was concentrated and the residue was washed with PE (100 mL) to afford the product 4-[2-(2,4-dichloroanilino)thiazol-4-yl]-4-ethoxycarbonyl-hexanoic acid. During preparation of sample for the purification of prep-HPLC, it was converted to the 4-[5-bromo-2-(2,4-dichloroanilino)thiazol-4-yl]-4-ethoxycarbonyl-hexanoic acid because of presence of residual HBr. It was purified by prep-HPLC (neutral condition) to afford the title compound (24.6 mg, 46.77 umol, 22.17% yield, 97% purity) as yellow solid.

LCMS: $(M+H^+)$: 510.8@2.453 min (CD15-100% ACN in $H_2O$, 4.5 min).

1H NMR: (400 MHz, METHANOL-d4) δ ppm 8.43 (d, J=8.8 Hz, 1H), 7.43 (d, J=2.4 Hz, 1H), 7.29 (dd, J=2.4, 8.8 Hz, 1H), 4.28-4.12 (m, 2H), 2.46-2.35 (m, 2H), 2.30-2.01 (m, 4H), 1.30-1.23 (m, 3H), 0.84 (t, J=7.5 Hz, 3H).

Example 15. Synthesis of (4R)-4-[2-(2,4-dichloroanilino)thiazol-4-yl]-4-ethoxycarbonyl-hexanoic acid (Cmp. 15a) and (4S)-4-[2-(2,4-dichloroanilino)thiazol-4-yl]-4-ethoxycarbonyl-hexanoic acid (Cmp. 15B)

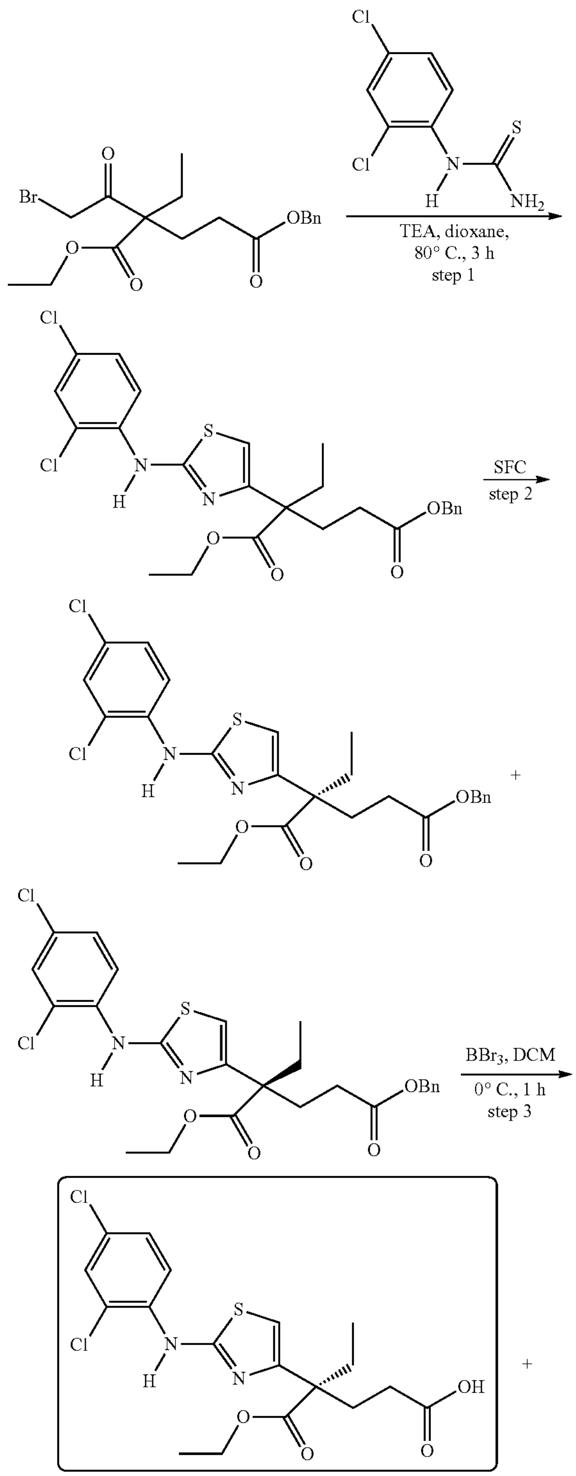

Cmp. 15a, temporarily assignment

-continued

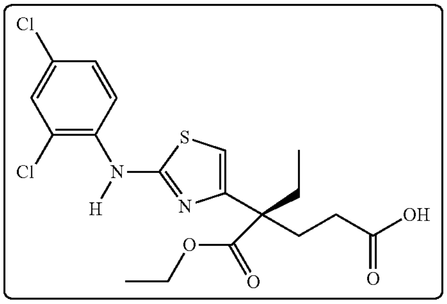

Cmp. 15b, temporarily assignment

Step 1. Synthesis of O5-benzyl O1-ethyl(2R)-2-[2-(2,4-dichloroanilino)thiazol-4-yl]-2-ethyl-pentanedioate and O5-benzyl O1-ethyl(2S)-2-[2-(2,4-dichloroanilino)thiazol-4-yl]-2-ethyl-pentanedioate To a solution of O5-benzyl O1-ethyl 2-(2-bromoacetyl)-2-ethyl-pentanedioate (1 g, 2.50 mmol, 1 eq) in dioxane (10 mL) was added (2,4-dichlorophenyl)thiourea (553.77 mg, 2.50 mmol, 1 eq) and TEA (760.30 mg, 7.51 mmol, 1.05 mL, 3 eq). The mixture was stirred at 80° C. for 3 h. The mixture was allowed to cool to the room temperature and then filtered and concentrated. The residue was purified by MPLC ($SiO_2$, PE:EtOAc=20/1 to 4/1) to obtain the racemic product (700 mg, not pure). It was re-purified by reversed-phase MPLC to obtain the racemic (390 mg, 97% purity). It was separated by SFC (column: DAICEL CHIRALPAK AD (250 mm*30 mm, 10 um); mobile phase: [0.1% $NH_3H_2O$ IPA]; B %: 30%-30%, 6 min) to afford the compound P1: (110 mg, 197.66 umol, 7.89% yield, 93.7% purity, 99.44% ee, Rt=2.870 min) as yellow oil; P2 (100 mg, 173.88 umol, 6.94% yield, 90.67% purity, 95.28% ee, Rt=2.970 min) as yellow oil.

P1: HPLC: (10-80% ACN in $H_2O$, 6 min), SFC: Rt=2.870 min.

P2: HPLC: (10-80% ACN in $H_2O$, 6 min), SFC: Rt=2.970 min.

Step 2. Synthesis of (4R)-4-[2-(2,4-dichloroanilino) thiazol-4-yl]-4-ethoxycarbonyl-hexanoic acid and (Cmp. 15a)

To a solution of O5-benzyl O1-ethyl(2R)-2-[2-(2,4-dichloroanilino)thiazol-4-yl]-2-ethyl-pentanedioate (110.00 mg, 210.95 umol, 1 eq) in DCM (2 mL) was added $BBr_3$ (158.54 mg, 632.84 umol, 60.98 uL, 3 eq) at 0° C. The mixture was stirred at 0° C. for 1 h. The mixture was concentrated and washed with PE (100 mL). The residue dissolved in ACN (20 mL). The mixture pH was adjusted to 9 with $NH_3.H_2O$ (25%) and purified by prep-HPLC (neutral condition) to afford the title compound (17.8 mg, 40.90 umol, 19.39% yield, 99.10% purity, 99.58% ee, Rt=2.752 min) as yellow solid.

LCMS: ($M-H^+$): 430.9@5.659 min (0-100% ACN in $H_2O$, 10 min).

$^1H$ NMR: (400 MHz, METHANOL-d4) δ ppm 8.40 (d, J=8.8 Hz, 1H), 7.41 (d, J=2.4 Hz, 1H), 7.24 (dd, J=2.4, 9.0 Hz, 1H), 6.73 (s, 1H), 4.15 (q, J=7.1 Hz, 2H), 2.44-2.21 (m, 2H), 2.14-1.95 (m, 4H), 1.21 (t, J=7.1 Hz, 3H), 0.80 (t, J=7.5 Hz, 3H).

SFC: Rt=2.752 min.

Step 3. Synthesis of (4S)-4-[2-(2,4-dichloroanilino) thiazol-4-yl]-4-ethoxycarbonyl-hexanoic acid (Cmp. 15b)

To a solution of O5-benzyl O1-ethyl(2S)-2-[2-(2,4-dichloroanilino)thiazol-4-yl]-2-ethyl-pentanedioate (100.00 mg, 191.77 umol, 1 eq) in DCM (5 mL) was added $BBr_3$ (144.13 mg, 575.31 umol, 55.43 uL, 3 eq) at 0° C. The mixture was stirred at 0° C. for 1 h. The mixture was concentrated and washed with PE (100 mL). The residue dissolved in ACN (20 mL). The mixture pH was adjusted to 9 with $NH_3.H_2O$ (25%) and purified by prep-HPLC (neutral condition) to afford the title compound (25.1 mg, 57.39 umol, 29.93% yield, 98.63% purity, 93.12% ee, Rt=2.894 min) as yellow solid.

LCMS: $(M-H^+)$: 430.9@5.654 min (0-100% ACN in $H_2O$, 10 min).

$^1H$ NMR: (400 MHz, METHANOL-d4) δ ppm 8.40 (d, J=9.0 Hz, 1H), 7.41 (d, J=2.4 Hz, 1H), 7.24 (dd, J=2.4, 9.0 Hz, 1H), 6.73 (s, 1H), 4.15 (q, J=7.1 Hz, 2H), 2.39-2.27 (m, 2H), 2.13-1.96 (m, 4H), 1.21 (t, J=7.2 Hz, 3H), 0.79 (t, J=7.4 Hz, 3H).

SFC: Rt=2.894 min.

Example 16. Synthesis of 4-Tert-Butoxycarbonyl-4-[6-(4-Methylanilino) Pyrazin-2-yl]Hexanoic Acid (Cmp. 16)

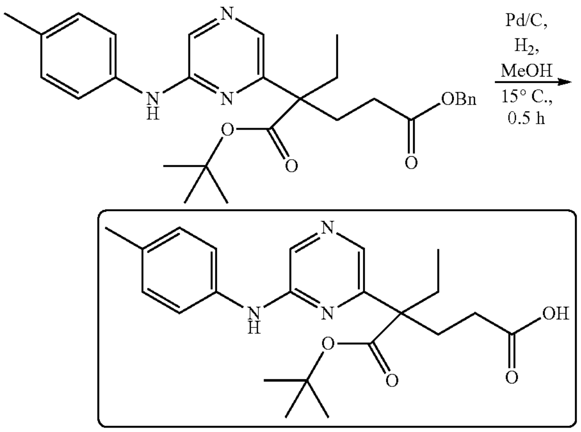

Cmp. 16, RS

Synthesis of 4-tert-butoxycarbonyl-4-[6-(4-methylanilino) pyrazin-2-yl]hexanoic acid (Cmp. 16)

To a solution of O5-benzyl O1-tert-butyl 2-ethyl-2-[6-(4-methylanilino) pyrazin-2-yl]pentanedioate (0.1 g, 204.25 umol, 1 eq) in MeOH (5 mL) was added Pd/C (0.1 g, 10% purity) under $N_2$. The suspension was degassed under vacuum and purged with $H_2$ several times. The mixture was stirred under $H_2$ (15 psi) at 15° C. for 0.5 h. It was filtered and the filtrate was concentrated under vacuum. The residue was purified by prep-HPLC (neutral condition) to afford the title compound (44.8 mg, 111.56 umol, 54.62% yield, 99.48% purity) as yellow solid.

LCMS: $(M+H^+)$: 400.1@2.120 min (15-100% ACN in $H_2O$, 4.5 min). $^1H$ NMR: (400 MHz, METHANOL-d4) δ ppm 7.95 (s, 1H), 7.80 (s, 1H), 7.57 (d, J=8.4 Hz, 2H), 7.09 (d, J=8.3 Hz, 2H), 2.46-2.31 (m, 2H), 2.29 (s, 3H), 2.19-2.05 (m, 4H), 1.38 (s, 9H), 0.85 (t, J=7.4 Hz, 3H).

Example 17. Synthesis of 4-ethoxycarbonyl-4-[6-(2-methoxyanilino)pyrazin-2-yl]hexanoic acid (Cmp. 17 (RS))

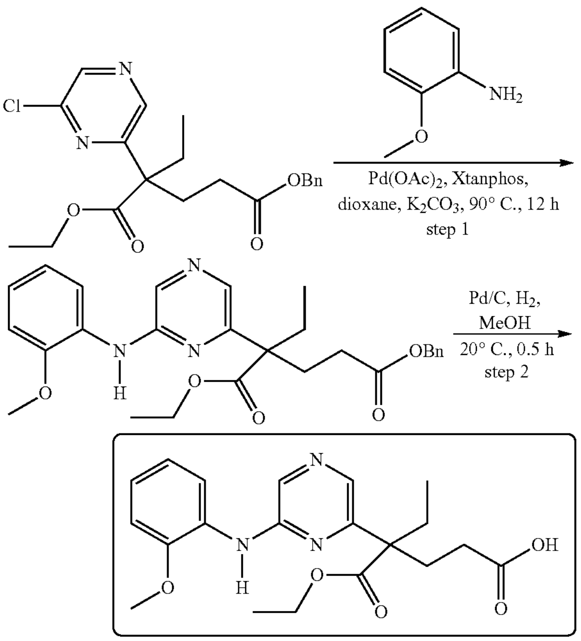

Cmp. 17

Step 1. Synthesis of O5-benzyl O1-ethyl 2-ethyl-2-[6-(2-methoxyanilino)pyrazin-2-yl]pentanedioate To a solution of O5-benzyl O1-ethyl 2-(6-chloropyrazin-2-yl)-2-ethyl-pentanedioate (170 mg, 434.94 umol, 1 eq) in dioxane (3 mL) was added 2-methoxyaniline (66.95 mg, 543.67 umol, 61.43 uL, 1.25 eq), Xantphos (62.92 mg, 108.73 umol, 0.25 eq), $K_2CO_3$ (180.34 mg, 1.30 mmol, 3 eq) and $Pd(OAc)_2$ (9.76 mg, 43.49 umol, 0.1 eq). The mixture was stirred at 90° C. for 12 h under $N_2$. It was cooled to the room temperature and poured into water (15 mL), extracted with EtOAc (15 mL*3), washed with brine (15 mL*3), dried over anhydrous $Na_2SO_4$ and concentrated. The residue was purified by MPLC ($SiO_2$, PE:EtOAc=10/1 to 2/1) to afford the title compound (200 mg, 276.41 umol, 63.55% yield, 66% purity) as brown oil.

LCMS: $(M+H^+)$: 478.2@1.552 min (10-90% ACN in $H_2O$, 2 min).

Step 2. Synthesis of 4-ethoxycarbonyl-4-[6-(2-methoxyanilino)pyrazin-2-yl]hexanoic acid (Cmp. 17, (RS))

To a solution of O5-benzyl O1-ethyl 2-ethyl-2-[6-(2-methoxyanilino)pyrazin-2-yl]pentanedioate (170 mg, 355.98 umol, 1 eq) in MeOH (10 mL) was added Pd/C (0.2 g, 10% purity) under $N_2$. The suspension was degassed under vacuum and purged with $H_2$ several times. The mixture was stirred at 20° C. for 0.5 h (15 psi). It was filtered and the filtrate was concentrated. The residue was purified by prep-HPLC (HCl condition) to afford the title compound (27.1 mg, 99.09% purity, as a HCl salt) as yellow solid.

LCMS: $(M+H^+)$: 388.2@2.696 min (0-100% ACN in $H_2O$, 4.5 min).

1H NMR: (400 MHz, METHANOL-d4) δ ppm 8.30-8.23 (m, 1H), 8.14 (s, 1H), 7.86 (s, 1H), 7.03-6.99 (m, 2H), 6.94-6.88 (m, 1H), 4.21-4.11 (m, 2H), 3.92 (s, 3H), 2.50-2.28 (m, 2H), 2.20-2.06 (m, 4H), 1.17 (t, J=7.2 Hz, 3H), 0.85 (t, J=7.5 Hz, 3H).

Example 18. Synthesis of 4-[6-(2,4-difluoroanilino) pyrazin-2-yl]-4-ethyl-hexanoic acid (Cmp. 18)

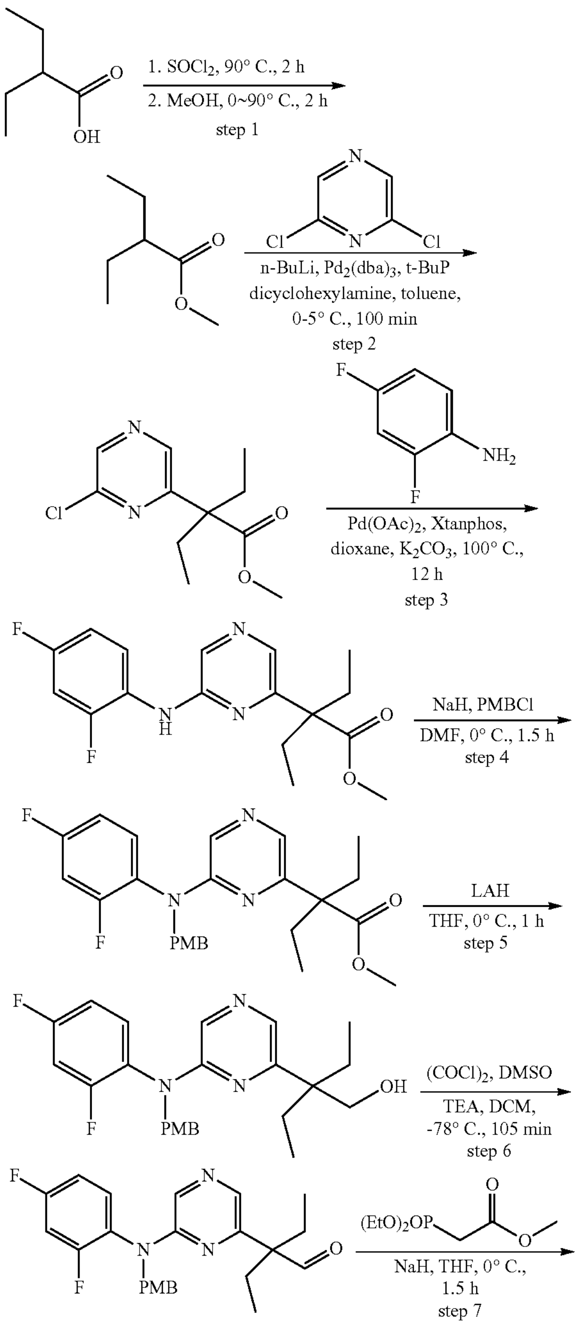

-continued

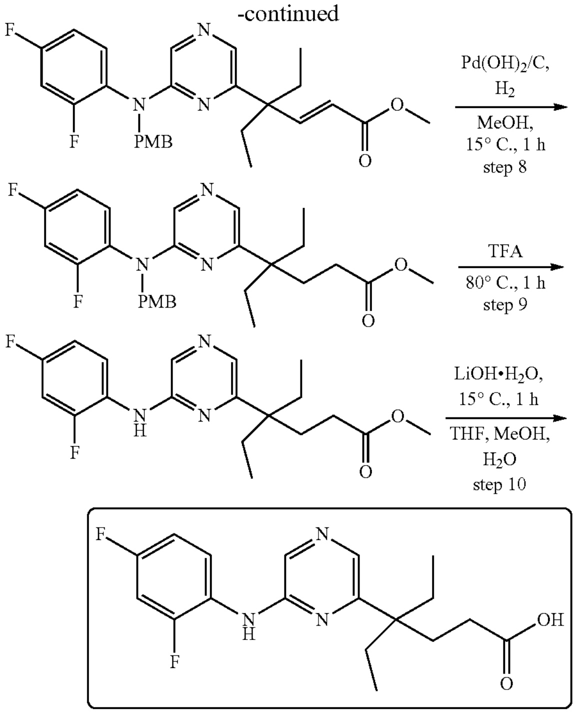

Cmp. 18

Step 1. Synthesis of Methyl 2-ethylbutanoate

A mixture of 2-ethylbutanoic acid (25 g, 215.22 mmol, 27.11 mL, 1 eq) and $SOCl_2$ (43.53 g, 365.88 mmol, 26.54 mL, 1.7 eq) was stirred at 90° C. for 2 h. Then it was cooled to room temperature and concentrated in vacuum to give a residue. The residue was cooled to 0° C. and MeOH (20.69 g, 645.67 mmol, 26.13 mL, 3 eq) was added carefully. Then the resulting mixture was stirred at 90° C. for 2 h. It was concentrated under vacuum below 30° C. to give a residue. The residue was distilled to afford the title compound (20 g, 153.63 mmol, 71.38% yield) as colorless oil.

$^1H$ NMR: (400 MHz, METHANOL-d4) δ ppm 3.75-3.60 (m, 3H), 2.22 (tt, J=5.5, 8.6 Hz, 1H), 1.73-1.39 (m, 4H), 0.89 (t, J=7.4 Hz, 6H).

Step 2. Synthesis of Methyl 2-(6-chloropyrazin-2-yl)-2-ethyl-butanoate

To a solution of N-cyclohexylcyclohexanamine (3.34 g, 18.44 mmol, 3.67 mL, 1.2 eq) in toluene (40 mL) was added n-BuLi (2.5 M, 7.37 mL, 1.2 eq) dropwise at 0° C. The mixture was stirred at 0° C. for 10 min before methyl 2-ethylbutanoate (2 g, 15.36 mmol, 1 eq) in toluene (5 mL) was added, after 0.5 h, the mixture was added to a solution of 2,6-dichloropyrazine (2.29 g, 15.36 mmol, 1 eq) and $Pd_2(dba)_3$ (140.68 mg, 153.63 umol, 0.01 eq) in toluene (10 mL). Finally, tritert-butylphosphane (621.63 mg, 307.26 umol, 721.15 uL, 10% purity, 0.02 eq) was added to the above mixture and stirred at 5° C. for 1 h. It was poured into water (100 mL). The aqueous phase was extracted with ethyl acetate (50 mL*3). The combined organic phase was dried over anhydrous $Na_2SO_4$, filtered and concentrated under vacuum. The residue was purified by silica gel chromatography (100-200 mesh silica gel, Petroleum ether/Ethyl acetate=100/1, 3/1) to afford the title compound (2.4 g, 6.82 mmol, 44.41% yield, 69% purity) as yellow oil.

LCMS: $(M+H^+)$: 243.3@1.170 min (5-95% ACN in $H_2O$, 2.0 min).

Step 3. Synthesis of Methyl 2-[6-(2,4-difluoroanilino)pyrazin-2-yl]-2-ethyl-butanoate To a solution of methyl 2-(6-chloropyrazin-2-yl)-2-ethyl-butanoate (2.4 g, 9.89 mmol, 1 eq) and 2,4-difluoroaniline (1.92 g, 14.83 mmol, 1.5 eq) in dioxane (30 mL) was added $Pd(OAc)_2$ (222.01 mg, 988.87 umol, 0.1 eq), Xantphos (1.14 g, 1.98 mmol, 0.2 eq) and $K_2CO_3$ (2.73 g, 19.78 mmol, 2 eq). The mixture was stirred at 100° C. for 12 h. It was poured into water (100 mL). The aqueous phase was extracted with ethyl acetate (50 mL*3). The combined organic phase was washed with brine (50 mL*2), dried over anhydrous $Na_2SO_4$, filtered and concentrated under vacuum. The residue was purified by silica gel chromatography (100-200 mesh silica gel, Petroleum ether/Ethyl acetate=10/1, 3/1) to afford the title compound (3 g, 8.95 mmol, 90.47% yield) as brown solid.

Step 4. Synthesis of Methyl 2-[6-[2,4-difluoro-N-[(4-methoxyphenyl)methyl]anilino]pyrazin-2-yl]-2-ethyl-butanoate To a solution of methyl 2-[6-(2,4-difluoroanilino)pyrazin-2-yl]-2-ethyl-butanoate (1 g, 2.98 mmol, 1 eq) in DMF (10 mL) was added NaH (155.05 mg, 3.88 mmol, 60% purity, 1.3 eq) at 0° C. After 0.5 h, 1-(chloromethyl)-4-methoxybenzene (560.41 mg, 3.58 mmol, 487.31 uL, 1.2 eq) was added to the above and the resulting mixture was stirred at 0° C. for 1 h. The residue was poured into water (50 mL). The aqueous phase was extracted with ethyl acetate (30 mL*3). The combined organic phase was washed with brine (50 mL*2), dried over anhydrous $Na_2SO_4$, filtered and concentrated under vacuum. The residue was purified by silica gel chromatography (100-200 mesh silica gel, Petroleum ether/Ethyl acetate=10/1, 3/1) to afford the title compound (1 g, 2.20 mmol, 73.62% yield) as brown solid.

$^1H$ NMR: (400 MHz, METHANOL-d4) δ ppm 7.86 (s, 1H), 7.50 (s, 1H), 7.36-7.22 (m, 1H), 7.18-7.07 (m, 3H), 7.07-6.96 (m, 1H), 6.80 (d, J=8.6 Hz, 2H), 5.02 (s, 2H), 3.74 (s, 3H), 3.64 (s, 3H), 2.16-2.06 (m, 4H), 0.75 (t, J=7.4 Hz, 6H).

Step 5. Synthesis of 2-[6-[2,4-difluoro-N-[(4-methoxyphenyl)methyl]anilino]pyrazin-2-yl]-2-ethyl-butan-1-ol To a solution of methyl 2-[6-[2,4-difluoro-N-[(4-methoxyphenyl)methyl]anilinomethyl 2-[6-[2,4-difluoro-N-[(4-methoxyphenyl)methyl]anilino]pyrazin-2-yl]-2-ethyl-butanoate (0.9 g, 1.98 mmol, 1 eq) in THF (30 mL) was added $LiAlH_4$ (149.99 mg, 3.95 mmol, 2 eq) at 0° C., then the mixture was stirred at 0° C. for 1 h. It was quenched with aqueous HCl (50 mL, 1 N), extracted with ethyl acetate (30 mL*3). The combined organic phase was dried over anhydrous $Na_2SO_4$, filtered and concentrated in vacuum to afford the title compound (1 g, crude) as yellow oil and used directly in the next step.

Step 6. Synthesis of 2-[6-[2,4-difluoro-N-[(4-methoxyphenyl)methyl]anilino]pyrazin-2-yl]-2-ethyl-butanal To a solution of $(COCl)_2$ (593.83 mg, 4.68 mmol, 409.53 uL, 2 eq) in DCM (15 mL) was added DMSO (365.55 mg, 4.68 mmol, 365.55 uL, 2 eq) at −78° C., after the reaction was stirred for 15 min 2-[6-[2,4-difluoro-N-[(4-methoxyphenyl)methyl]anilino]pyrazin-2-yl]-2-ethyl-butan-1-ol (1 g, 2.34 mmol, 1 eq) in DCM (3 mL) was added to the above solution and stirred for 30 min. Then TEA (1.18 g, 11.70 mmol, 1.63 mL, 5 eq) was added dropwise. The mixture was allowed to warm to 0° C. and stirred at this temperature for 1 h. It was quenched with Sat. $NH_4Cl$ solution (50 mL), extracted with DCM (30 mL*3). The combined organic phase was dried over anhydrous $Na_2SO_4$, filtered and concentrated in vacuum. The residue was purified by silica gel chromatography (100-200 mesh silica gel, Petroleum ether/Ethyl acetate=10/1, 3/1) to afford the title compound (0.7 g, 1.41 mmol, 60.49% yield, 86% purity) as yellow oil.

LCMS: (M+1-1±): 426.1@1.597 min (5-95% ACN in $H_2O$, 2.0 min).

Step 7. Synthesis of Methyl (E)-4-[6-[2,4-difluoro-N-[(4-methoxyphenyl)methyl]anilino]pyrazin-2-yl]-4-ethyl-hex-2-enoate To a solution of 2-[6-[2,4-difluoro-N-[(4-methoxyphenyl)methyl]anilino]pyrazin-2-yl]-2-ethyl-butanal (0.3 g, 705.10 umol, 1 eq) in THF (10 mL) was added NaH (56.41 mg, 1.41 mmol, 60% purity, 2 eq) at 0° C. After 0.5 h, methyl 2-diethoxyphosphorylacetate (296.38 mg, 1.41 mmol, 2 eq) was added to the above and the mixture was stirred at 0° C. for 1 h. It was poured into water (20 mL). The aqueous phase was extracted with ethyl acetate (30 mL*3). The combined organic phase was washed with brine (50 mL*2), dried over anhydrous $Na_2SO_4$, filtered and concentrated in vacuum. The residue was purified by silica gel chromatography (100-200 mesh silica gel, Petroleum ether/Ethyl acetate=10/1, 2/1) to afford the title compound (0.28 g, 523.33 umol, 74.22% yield, 90% purity) as yellow oil.

Step 8. Synthesis of Methyl 4-[6-[2,4-difluoro-N-[(4-methoxyphenyl)methyl]anilino]pyrazin-2-yl]-4-ethyl-hexanoate To a solution of methyl (E)-4-[6-[2,4-difluoro-N-[(4-methoxyphenyl)methyl]anilino]pyrazin-2-yl]-4-ethyl-hex-2-enoate (0.2 g, 415.34 umol, 1 eq) in MeOH (10 mL) was added $Pd(OH)_2/C$ (500.00 mg, 20% purity) under $N_2$. The suspension was degassed under vacuum and purged with $H_2$ several times. The mixture was stirred under $H_2$ (15 psi) at 15° C. for 1 h. It was filtered and the filtrate was concentrated in vacuum to afford the title compound (0.2 g, crude) as yellow oil and used directly in next step.

LCMS: $(M+H^+)$: 484.2@1.440 min (5-95% ACN in $H_2O$, 2.0 min).

Step 9. Synthesis of Methyl 4-[6-(2,4-difluoroanilino)pyrazin-2-yl]-4-ethyl-hexanoate A mixture of methyl 4-[6-[2,4-difluoro-N-[(4-methoxyphenyl)methyl]anilino]pyrazin-2-yl]-4-ethyl-hexanoate (0.2 g, 413.61 umol, 1 eq) in TFA (5 mL) was stirred at 80° C. for 1 h.

It was concentrated in vacuum to give a residue and the pH was adjusted to 9 with Sat. $NaHCO_3$ solution and the aqueous phase was extracted with ethyl acetate (20 mL*3). The combined organic phase was washed with brine (30 mL*2), dried over anhydrous $Na_2SO_4$, filtered and concentrated in vacuum. The residue was purified by silica gel chromatography (100-200 mesh silica gel, Petroleum ether/Ethyl acetate=10/1, 2/1) to afford the title compound (0.13 g) as yellow oil.

Step 10. Synthesis of 4-[6-(2,4-difluoroanilino) pyrazin-2-yl]-4-ethyl-hexanoic acid (Cmp. 18)

To a solution of methyl 4-[6-(2,4-difluoroanilino)pyrazin-2-yl]-4-ethyl-hexanoate (0.1 g, 275.18 umol, 1 eq) in MeOH (1 mL)/THF (5 mL)/$H_2O$ (1 mL) was added LiOH·$H_2O$ (57.74 mg, 1.38 mmol, 5 eq) and the reaction was stirred at 15° C. for 1 h. The pH of the reaction mixture was adjusted to 5 with aqueous HCl (1 N), the mixture was extracted with ethyl acetate (20 mL*2). The combined organic phase was dried over anhydrous $Na_2SO_4$, filtered and concentrated in vacuum. The residue was purified by prep-HPLC (HCl) to afford the title compound (63.2 mg, 95.1% purity, as a HCl salt) as yellow oil.

LCMS: (M+H$^+$): 350.2@2.820 min (10-100% ACN in $H_2O$, 4.5 min).

$^1$H NMR: (400 MHz, METHANOL-d4) δ ppm 8.09-8.00 (m, 2H), 7.93 (s, 1H), 7.05 (ddd, J=2.8, 8.6, 11.2 Hz, 1H), 6.99-6.89 (m, 1H), 2.07 (s, 4H), 1.87-1.68 (m, 4H), 0.74 (t, J=7.4 Hz, 6H).

Example 19. Synthesis of 4-[6-(2,4-difluoroanilino)-3-ethyl-pyrazin-2-yl]-4-ethyl-hexanoic acid (Cmp. 19)

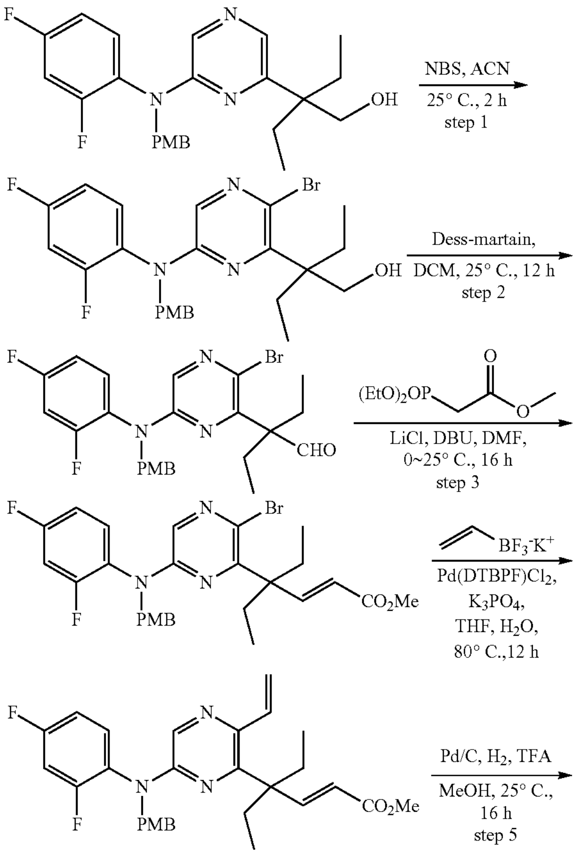

-continued

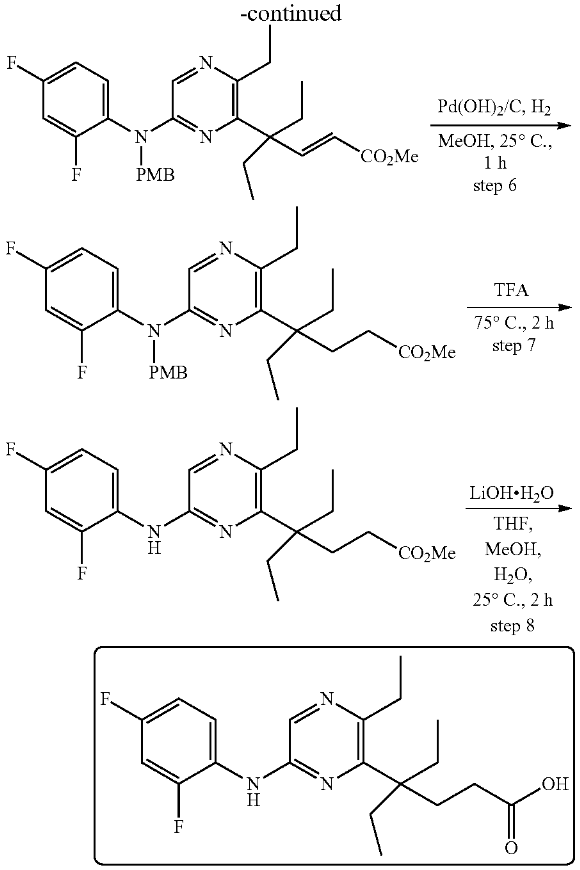

Cmp. 19

Step 1. Synthesis of 2-[3-bromo-6-[2,4-difluoro-N-[(4-methoxyphenyl)methyl]anilino]pyrazin-2-yl]-2-ethyl-butan-1-ol To a solution of 2-[6-[2,4-difluoro-N-[(4-methoxyphenyl) methyl]anilino]pyrazin-2-yl]-2-ethyl-butan-1-ol (1.7 g, 3.98 mmol, 1 eq) in ACN (20 mL) was added NBS (743.19 mg, 4.18 mmol, 1.05 eq). The mixture was stirred at 25° C. for 2 h. After completion of the reaction, the mixture was poured into water (50 mL). The aqueous phase was extracted with ethyl acetate (20 mL*3). The combined organic phase was washed with brine (30 mL*2), dried over anhydrous $Na_2SO_4$, filtered and concentrated in vacuum. The residue was purified by silica gel chromatography (Petroleum ether/Ethyl acetate=10/1, 3/1) to afford the title compound (0.85 g, 1.51 mmol, 37.99% yield, 90% purity) as yellow oil.

Step 2. Synthesis of 2-[3-bromo-6-[2,4-difluoro-N-[(4-methoxyphenyl)methyl]anilino]pyrazin-2-yl]-2-ethyl-butanal To a solution of 2-[3-bromo-6-[2,4-difluoro-N-[(4-methoxyphenyl)methyl]anilino]pyrazin-2-yl]-2-ethyl-butan-1-ol (0.85 g, 1.68 mmol, 1 eq) in DCM (20 mL) was added Dess-Martin periodinate (854.34 mg, 2.01 mmol, 623.61 uL, 1.2 eq). The mixture was stirred at 25° C. for 12 h. After completion of the reaction, it was quenched with Sat. $NaHCO_3$ (20 mL), extracted with DCM (20 mL*2). The combined organic phase was dried with anhydrous $Na_2SO_4$, filtered and concentrated in vacuum. The residue was purified by silica gel chromatography (Petroleum ether/Ethyl acetate=10/1, 3/1) to afford the title compound (0.6 g, 1.19 mmol, 70.87% yield) as yellow oil Step 3. Synthesis of Methyl (E)-4-[3-bromo-6-[2,4-difluoro-N-[(4-methoxyphenyl)methyl]anilino]pyrazin-2-yl]-4-ethyl-hex-2-enoate To a solution of methyl 2-diethoxyphosphorylacetate (412.82 mg, 1.96 mmol, 2 eq) in DMF (10 mL) was added LiCl (41.64 mg, 982.14 umol, 20.11 uL, 1 eq) and DBU (299.04 mg, 1.96 mmol, 296.08 uL, 2 eq). The mixture was stirred at 0° C. for 30 min, then a mixture of 2-[3-bromo-6-[2,4-difluoro-N-[(4-methoxyphenyl)methyl]anilino]pyrazin-2-yl]-2-ethyl-butanal and methyl (E)-4-[3-bromo-6-[2,4-difluoro-N-[(4-methoxyphenyl)methyl]anilino]pyrazin-2-yl]-4-ethyl-hex-2-enoate (0.55 g, 982.14 umol, 1 eq) was added to the above solution and the resulting mixture was stirred at 25° C. for 15.5 h. After completion of the reaction, it was poured into water (30 mL). The aqueous phase was extracted with ethyl acetate (20 mL*3). The combined organic phase was washed with brine (30 mL*2), dried over anhydrous $Na_2SO_4$, filtered and concentrated in vacuum. The residue was purified by silica gel chromatography (Petroleum ether/Ethyl acetate=10/1, 3/1) to afford the title compound (0.6 g, crude) as yellow oil.

Step 4. Synthesis of Synthesis of Methyl (E)-4-[6-[2,4-difluoro-N-[(4-methoxyphenyl)methyl]anilino]-3-vinyl-pyrazin-2-yl]-4-ethyl-hex-2-enoate To a solution of methyl (E)-4-[3-bromo-6-[2,4-difluoro-N-[(4-methoxyphenyl)methyl]anilino]pyrazin-2-yl]-4-ethyl-hex-2-enoate (0.6 g, 1.07 mmol, 1 eq), potassium trifluoro(vinyl) boranuide (717.04 mg, 5.35 mmol, 5 eq) in THF (10 mL)/$H_2O$ (2 mL) was added $K_3PO_4$ (454.52 mg, 2.14 mmol, 2 eq) and ditert-butyl(cyclopentyl)phosphane; dichloropalladium; iron (34.89 mg, 53.53 umol, 0.05 eq). The mixture was stirred at 80° C. under $N_2$ for 12 h. After completion of the reaction, it was cooled to room temperature and poured into water (30 mL). The aqueous phase was extracted with ethyl acetate (30 mL*3). The combined organic phase was washed with brine (40 mL*2), dried over anhydrous $Na_2SO_4$, filtered and concentrated in vacuum. The residue was purified by silica gel chromatography (Petroleum ether/Ethyl acetate=10/1, 3/1) to afford the title compound (0.3 g, crude) as yellow oil.

LCMS: ($M+H^+$): 508.2@1.516 min (5-95% ACN in $H_2O$, 2.0 min).

Step 5. Synthesis of Methyl (E)-4-[6-[2,4-difluoro-N-[(4-methoxyphenyl)methyl]anilino]-3-ethyl-pyrazin-2-yl]-4-ethyl-hex-2-enoate To a solution of methyl (E)-4-[6-[2,4-difluoro-N-[(4-methoxyphenyl)methyl]anilino]-3-vinyl-pyrazin-2-yl]-4-ethyl-hex-2-enoate (0.3 g, 591.05 umol, 1 eq) in MeOH (10 mL) was added Pd/C (0.3 g, 10% purity) and TFA (134.78 mg, 1.18 mmol, 87.52 uL, 2 eq) under $N_2$. The suspension was degassed under vacuum and purged with $H_2$ several times. The mixture was stirred under $H_2$ (15 psi) at 25° C. for 16 h. After completion of the reaction, it was filtered and the filtrate was concentrated in vacuum. The residue was purified by silica gel chromatography (Petroleum ether/Ethyl acetate=10/1, 3/1) to afford the title compound (0.14 g, 274.73 umol, 46.48% yield) as colorless oil.

LCMS: ($M+H^+$): 510.3@1.327 min (5-95% ACN in $H_2O$, 2.0 min).

Step 6. Synthesis of Methyl 4-[6-[2,4-difluoro-N-[(4-methoxyphenyl)methyl]anilino]-3-ethyl-pyrazin-2-yl]-4-ethyl-hexanoate To a solution of methyl (E)-4-[6-[2,4-difluoro-N-[(4-methoxyphenyl)methyl]anilino]-3-ethyl-pyrazin-2-yl]-4-ethyl-hex-2-enoate (0.14 g, 274.73 umol, 1 eq) in MeOH (4 mL) was added $Pd(OH)_2/C$ (0.2 g, 284.83 umol, 20% purity) under $N_2$. The suspension was degassed under vacuum and purged with $H_2$ several times. The mixture was stirred under $H_2$ (15 psi) at 25° C. for 1 h. After completion of the reaction, it was filtered and the filtrate was concentrated to afford the title compound (0.1 g, crude) as yellow oil.

LCMS: ($M+H^+$): 512.3@1.409 min (5-95% ACN in $H_2O$, 2.0 min).

Step 7. Synthesis of Methyl 4-[6-(2,4-difluoroanilino)-3-ethyl-pyrazin-2-yl]-4-ethyl-hexanoate A solution of methyl 4-[6-[2,4-difluoro-N-[(4-methoxyphenyl)methyl]anilino]-3-ethyl-pyrazin-2-yl]-4-ethyl-hexanoate (0.1 g, 195.46 umol, 1 eq) in TFA (2 mL) was stirred at 75° C. for 2 h. After completion of the reaction, it was concentrated in vacuum and the pH of the residue was adjusted to 9 with Sat. $NaHCO_3$. The aqueous phase was extracted with ethyl acetate (20 mL*3). The combined organic phase was dried over anhydrous $Na_2SO_4$, filtered and concentrated in vacuum. The residue was purified by silica gel chromatography (Petroleum ether/Ethyl acetate=10/1, 3/1) to afford the title compound (60 mg, 153.27 umol, 78.42% yield) as yellow oil.

Step 8. Synthesis of 4-[6-(2,4-difluoroanilino)-3-ethyl-pyrazin-2-yl]-4-ethyl-hexanoic acid (Cmp. 19)

To a solution of methyl 4-[6-(2,4-difluoroanilino)-3-ethyl-pyrazin-2-yl]-4-ethyl-hexanoate (0.04 g, 102.18 umol, 1 eq) in THF (3 mL)/MeOH (1 mL)/$H_2O$ (1 mL) was added $LiOH{\cdot}H_2O$ (21.44 mg, 510.92 umol, 5 eq). The mixture was stirred at 25° C. for 2 h. After completion of the reaction, the pH was adjusted to 3 with aqueous HCl (1N) and extracted with ethyl acetate (20 mL*2). The combined organic phase was dried over anhydrous $Na_2SO_4$, filtered and concentrated in vacuum. The residue was purified by prep-HPLC (HCl condition) to afford the title compound (32.2 mg, 100% purity, as a HCl salt) as yellow solid.

LCMS: ($M+H^+$): 378.2@2.532 min (5-95% ACN in $H_2O$, 6.0 min).

$^1H$ NMR: (400 MHz, METHANOL-d4) δ ppm 8.12-8.05 (m, 1H), 8.01 (s, 1H), 7.06-6.89 (m, 2H), 2.96 (q, J=7.5 Hz, 2H), 2.24-2.15 (m, 2H), 2.11-2.04 (m, 2H), 1.98-1.79 (m, 4H), 1.28 (t, J=7.4 Hz, 3H), 0.70 (t, J=7.4 Hz, 6H).

Example 20. Synthesis of 4-[6-(2,5-difluoroanilino)pyrazin-2-yl]-4-ethoxycarbonyl-hexanoic acid (Cmp. 20, (RS))

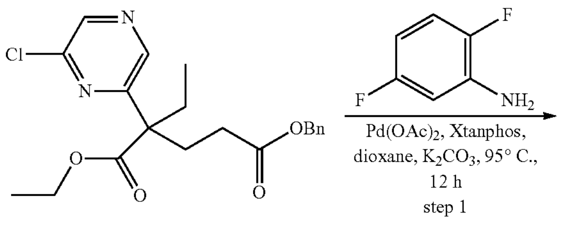

-continued

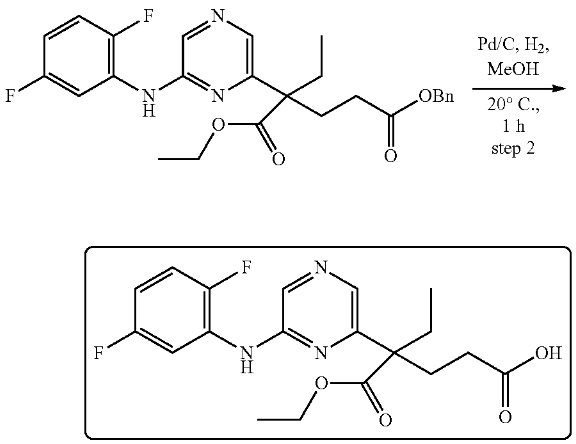

Cmp. 20

Step 1. Synthesis of O5-benzyl O1-ethyl 2-[6-(2,5-difluoroanilino)pyrazin-2-yl]-2-ethyl-pentanedioate To a solution of O5-benzyl O1-ethyl 2-(6-chloropyrazin-2-yl)-2-ethyl-pentanedioate (200 mg, 511.69 umol, 1 eq) in dioxane (2 mL) was added 2,5-difluoroaniline (82.58 mg, 639.62 umol, 64.51 uL, 1.25 eq), Xantphos (74.02 mg, 127.92 umol, 0.25 eq), $K_2CO_3$ (212.16 mg, 1.54 mmol, 3 eq) and $Pd(OAc)_2$ (11.49 mg, 51.17 umol, 0.1 eq). The mixture was stirred at 95° C. for 12 h under $N_2$. After the completion of the reaction, it was poured into water (15 mL), extracted with EtOAc (15 mL*3), washed with brine (15 mL*3), dried over anhydrous $Na_2SO_4$ and concentrated. The residue was purified by MPLC ($SiO_2$, PE:EtOAc=10/1 to 2/1) to afford the title compound (160 mg, 277.97 umol, 54.32% yield, 84% purity) as brown oil.

LCMS: (M+H$^+$): 484.3@1.264 min (5-95% ACN in $H_2O$, 2 min).

Step 2. Synthesis of 4-[6-(2,5-difluoroanilino) pyrazin-2-yl]-4-ethoxycarbonyl-hexanoic acid (Cmp. 20)

To a solution of O5-benzyl O1-ethyl 2-[6-(2,5-difluoroanilino)pyrazin-2-yl]-2-ethyl-pentanedioate (160 mg, 330.92 umol, 1 eq) in MeOH (5 mL) was added Pd/C (0.1 g, 10% purity) under $N_2$. The suspension was degassed under vacuum and purged with $H_2$ several times. The mixture was stirred at 20° C. for 1 h under $H_2$ (15 psi). After the completion of the reaction, it was filtered and the filtrate was concentrated. The residue was purified by prep-HPLC (HCl condition) to afford the title compound (27.4 mg, 63.55 umol, 19.21% yield, 99.70% purity, as a HCl salt) as yellow solid.

LCMS: (M+H$^+$): 394.1@2.782 min (0-100% ACN in $H_2O$, 4.5 min).

$^1$H NMR: (400 MHz, METHANOL-d4) δ ppm 8.29-8.16 (m, 2H), 8.02 (s, 1H), 7.14 (ddd, J=5.1, 9.1, 11.0 Hz, 1H), 6.79-6.64 (m, 1H), 4.20 (q, J=7.1 Hz, 2H), 2.52-2.41 (m, 1H), 2.41-2.30 (m, 1H), 2.21-2.11 (m, 4H), 1.19 (t, J=7.1 Hz, 3H), 0.86 (t, J=7.5 Hz, 3H).

Example 21. Synthesis of 4-[2-(2,4-difluoroanilino)-5-methyl-thiazol-4-yl]-4-ethyl-hexanoic acid (Cmp. 21)

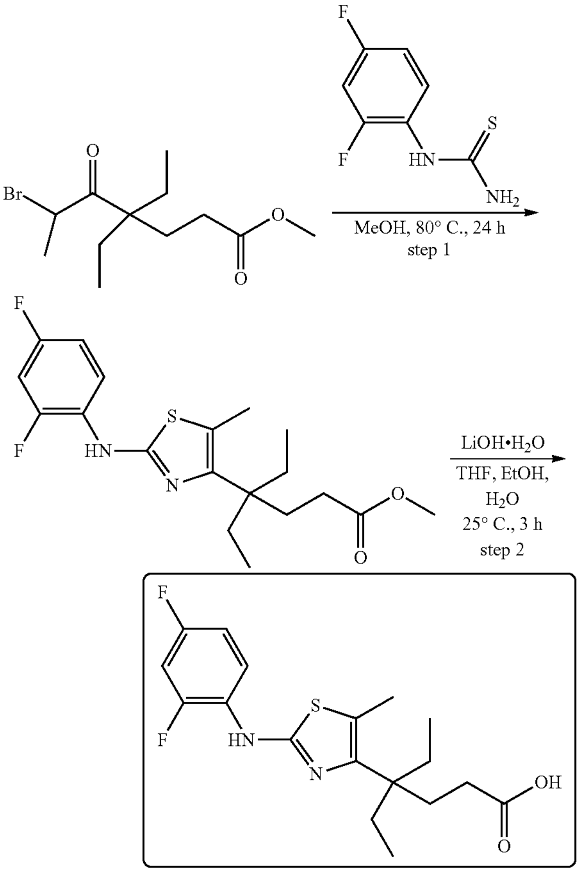

Cmp. 21

Step 1. Synthesis of methyl 4-[2-(2,4-difluoroanilino)-5-methyl-thiazol-4-yl]-4-ethyl-hexanoate To a solution of methyl 6-bromo-4,4-diethyl-5-oxo-heptanoate (400 mg, 1.36 mmol, 1 eq) in MeOH (4 mL) was added (2,4-difluorophenyl)thiourea (308.10 mg, 1.64 mmol, 1.2 eq). The mixture was stirred at 80° C. for 24 h. After the completion of the reaction, it was cooled to the room temperature and concentrated. The residue was purified by MPLC ($SiO_2$, PE:EtOAc=5/1 to 1/1) to afford the title compound (0.18 g, 376.50 umol, 27.60% yield, 80% purity) as yellow oil.

LCMS: (M+H$^+$): 383.2@2.385 min (5-95% ACN in $H_2O$, 4.5 min).

Step 2. Synthesis of 4-[2-(2,4-difluoroanilino)-5-methyl-thiazol-4-yl]-4-ethyl-hexanoic acid (Cmp. 21)

To a solution of methyl 4-[2-(2,4-difluoroanilino)-5-methyl-thiazol-4-yl]-4-ethyl-hexanoate (0.18 g, 470.63 umol, 1 eq) in EtOH (1 mL), THF (4 mL) and $H_2O$ (1 mL) was added LiOH·$H_2O$ (59.25 mg, 1.41 mmol, 3 eq). The mixture was stirred at 25° C. for 3 h. After the completion of the reaction, it was poured into water (10 mL) and the pH was adjusted to 3 with aq. HCl (1N), extracted with EtOAc (10 mL*3). The combined organic layers were washed with brine (10 mL*3), dried over anhydrous $Na_2SO_4$ and concentrated. The residue was purified by prep-HPLC (neutral condition) to afford the title compound (7.5 mg, 19.39 umol, 4.12% yield, 95.27% purity) as white solid.

LCMS: ($M+H^+$): 369.1@2.486 min (5-95% ACN in $H_2O$, 6 min).

$^1$H NMR: (400 MHz, METHANOL-d4) δ ppm 8.41 (dt, J=6.0, 9.4 Hz, 1H), 6.95 (ddd, J=2.9, 8.7, 11.6 Hz, 1H), 6.91-6.83 (m, 1H), 2.36 (s, 3H), 2.24-2.01 (m, 4H), 1.90-1.69 (m, 4H), 0.80 (t, J=7.4 Hz, 6H).

Example 22. Synthesis of methyl 4-[5-bromo-2-(2,4-difluoroanilino)thiazol-4-yl]-4-ethyl-hexanoate and 4-[5-bromo-2-(2,4-difluoroanilino)thiazol-4-yl]-4-ethyl-hexanoic acid (Cmp. 22a), and 4-[5-bromo-2-(2,4-difluoroanilino)thiazol-4-yl]-4-ethyl-hexanoic acid (Cmp. 22B)

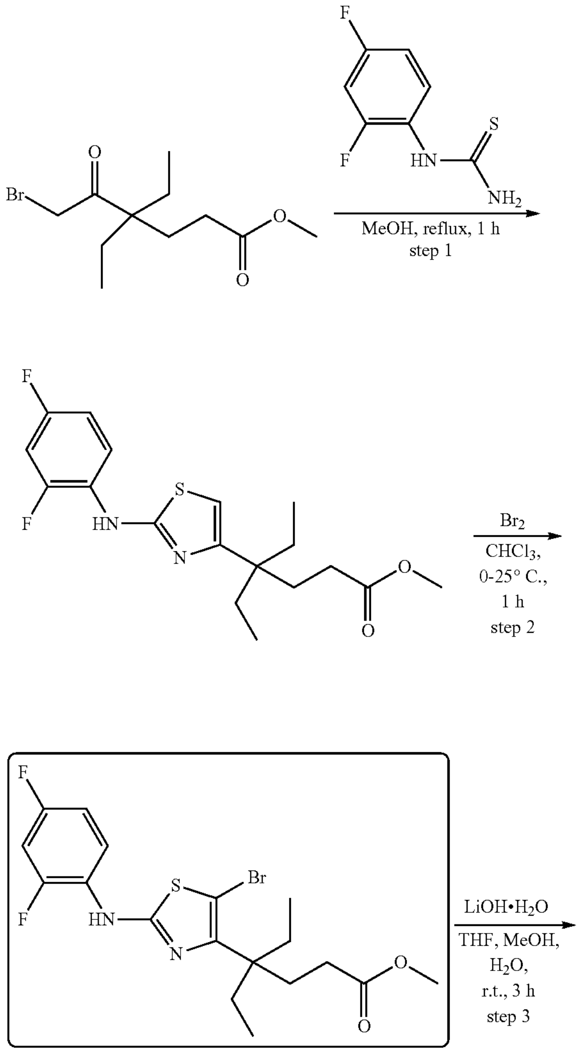

Cmp. 22a

-continued

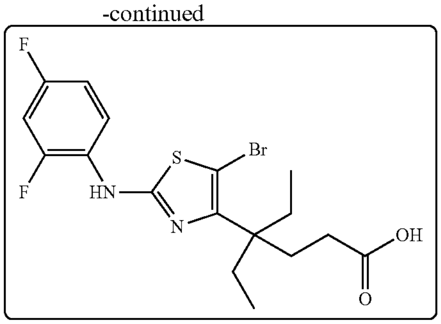

Cmp. 22b

Step 1. Synthesis of methyl 4-[2-(2,4-difluoroanilino)thiazol-4-yl]-4-ethyl-hexanoate To a solution of methyl 6-bromo-4,4-diethyl-5-oxo-hexanoate (670 mg, 2.40 mmol, 1 eq) in MeOH (8 mL) was added (2,4-difluorophenyl)thiourea (496.84 mg, 2.64 mmol, 1.1 eq). The mixture was stirred at 70° C. for 1 h. After the completion of the reaction, it was concentrated. The residue was purified by MPLC ($SiO_2$, PE:EtOAc=10/1 to 1/1) to afford the title compound (400 mg, 70% purity) as yellow solid.

$^1$H NMR: (400 MHz, CHLOROFORM-d) δ ppm 8.21-8.06 (m, 1H), 6.96-6.81 (m, 2H), 6.25 (s, 1H), 3.64 (s, 3H), 2.16-2.09 (m, 2H), 2.04-1.98 (m, 2H), 1.69 (qd, J=7.0, 12.1 Hz, 4H), 0.74 (t, J=7.5 Hz, 6H).

Step 2. Synthesis of methyl 4-[5-bromo-2-(2,4-difluoroanilino)thiazol-4-yl]-4-ethyl-hexanoate (Cmp. 22a)

To a solution of methyl 4-[2-(2,4-difluoroanilino)thiazol-4-yl]-4-ethyl-hexanoate (0.31 g, 841.38 umol, 1 eq) in $CHCl_3$ (3 mL) was added Bra (161.35 mg, 1.01 mmol, 52.05 uL, 1.2 eq) at 0° C. The mixture was stirred at 25° C. for 1 h. After the completion of the reaction, it was poured into sat. $NaHCO_3$ (30 mL), extracted with EtOAc (30 mL*3). The combined organic layers were washed with brine (30 mL*3), dried over anhydrous $Na_2SO_4$ and concentrated. The residue was purified by MPLC ($SiO_2$, PE:EtOAc=5/1 to 1/1) to afford the title compound (90 mg, 100.60 umol, 11.96% yield, 50% purity) as brown oil and used directly in the next step. 30 mg of crude product was purified by prep-HPLC (HCl condition) to afford the title compound (2 mg, 3.98 umol, 5.93% yield, 96.24% purity, HCl) as yellow solid.

LCMS: ($M+H^+$): 449.1@3.214 min (5-95% ACN in $H_2O$, 6 min).

$^1$H NMR: (400 MHz, METHANOL-d4) δ ppm 8.36 (dt, J=6.1, 9.3 Hz, 1H), 6.99 (ddd, J=2.8, 8.6, 11.4 Hz, 1H), 6.94-6.87 (m, 1H), 3.63 (s, 3H), 2.19 (q, J=5.6 Hz, 4H), 2.01-1.80 (m, 4H), 0.87-0.71 (m, 6H).

Step 3. Synthesis of 4-[5-bromo-2-(2,4-difluoroanilino)thiazol-4-yl]-4-ethyl-hexanoic acid (Cmp. 22b)

To a solution of methyl 4-[5-bromo-2-(2,4-difluoroanilino)thiazol-4-yl]-4-ethyl-hexanoate (70 mg, 156.48 umol, 1 eq) in THF (2 mL), MeOH (0.4 mL) and $H_2O$ (0.4 mL) was added $LiOH{\cdot}H_2O$ (19.70 mg, 469.45 umol, 3 eq). The mixture was stirred at 25° C. for 3 h. After the completion of the reaction, the pH was adjusted to 6 with aqueous HCl (1 N) and concentrated. The mixture was purified by prep-HPLC (HCl condition) to afford the title compound (7.5 mg, 100% purity, HCL salt) as white solid.

LCMS: $(M+H^+)$: 432.9@2.881 min (5-95% ACN in $H_2O$, 6 min).

$^1H$ NMR: (400 MHz, METHANOL-d4) δ ppm 8.38 (dt, J=6.0, 9.3 Hz, 1H), 6.99 (ddd, J=2.8, 8.6, 11.5 Hz, 1H), 6.93-6.87 (m, 1H), 2.18 (s, 4H), 2.01-1.82 (m, 4H), 0.87-0.77 (m, 6H).

Example 23. Synthesis of 4-[2-(2,4-dichloroanilino)-5-methyl-thiazol-4-yl]-4-ethoxycarbonyl-hexanoic acid (Cmp. 23 (RS))

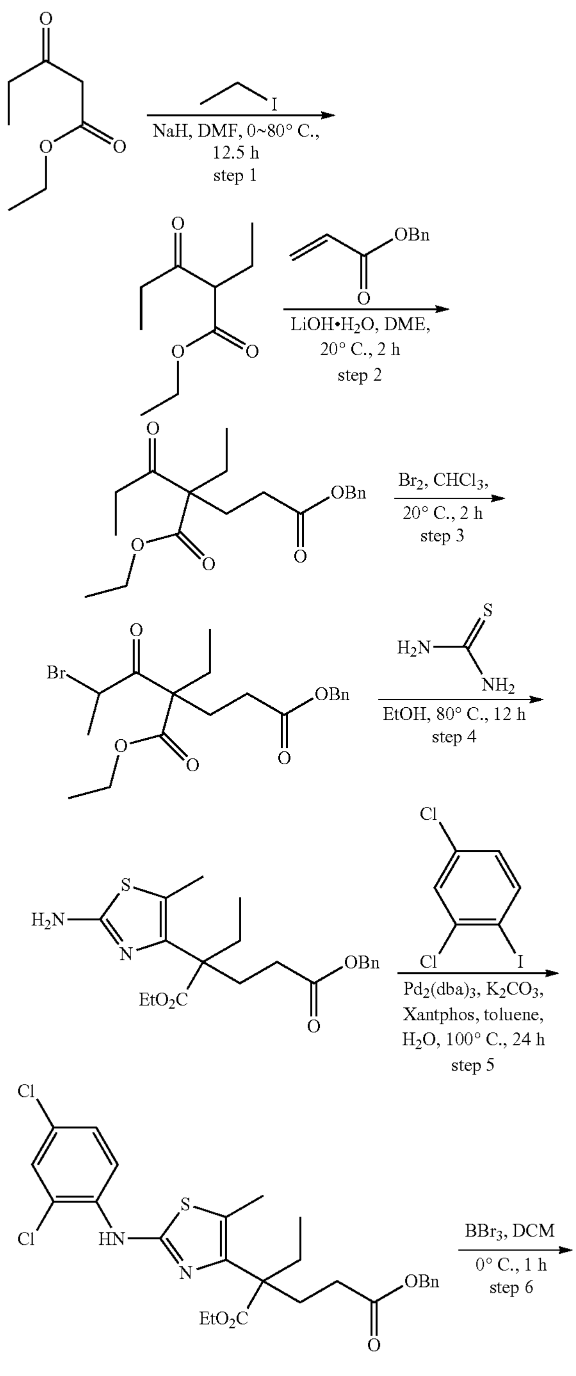

-continued

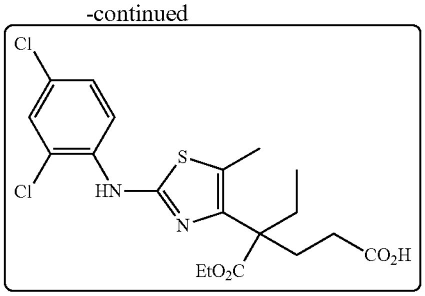

Cmp. 23

Step 1. Synthesis of Ethyl 2-ethyl-3-oxo-pentanoate

To a solution of ethyl 3-oxopentanoate (5 g, 34.68 mmol, 1 eq) in THF (50 mL) was added NaH (1.53 g, 38.15 mmol, 60% purity, 1.1 eq) at 0° C. and the reaction was stirred for 0.5 h, then ethyl iodide (5.95 g, 38.15 mmol, 3.05 mL, 1.1 eq) was added and the resulting mixture was heated to 80° C. and stirred at this temperature for 12 h. It was cooled to 15° C. and poured into water (50 mL), the aqueous phase was extracted with ethyl acetate (30 mL*3). The combined organic phase was washed with brine (30 mL*2), dried over anhydrous $Na_2SO_4$, filtered and concentrated in vacuum. The residue was purified by silica gel chromatography (Petroleum ether/Ethyl acetate=0/1, 50/1) to afford the title compound (4 g, 20.90 mmol, 60.27% yield, 90% purity) as colorless oil.

$^1H$ NMR: (400 MHz, CHLOROFORM-d) δ ppm 4.24-4.11 (m, 2H), 3.36 (t, J=7.4 Hz, 1H), 2.68-2.44 (m, 2H), 1.95-1.83 (m, 2H), 1.27 (t, J=7.1 Hz, 3H), 1.08 (t, J=7.3 Hz, 3H), 0.93 (t, J=7.4 Hz, 3H).

Step 2. Synthesis of O5-benzyl O1-ethyl 2-ethyl-2-propanoyl-pentanedioate

A mixture of ethyl 2-ethyl-3-oxo-pentanoate (1.2 g, 6.97 mmol, 1 eq), benzyl prop-2-enoate (1.70 g, 10.45 mmol, 1.5 eq) and $LiOH \cdot H_2O$ (584.79 mg, 13.94 mmol, 2 eq) in DME (10 mL) was stirred at 20° C. for 2 h. The reaction mixture was poured into water (10 mL), the aqueous phase was extracted with ethyl acetate (10 mL*3). The combined organic phase was washed with brine (10 mL*2), dried over anhydrous $Na_2SO_4$, filtered and concentrated in vacuum. The residue was purified by silica gel chromatography (Petroleum ether/Ethyl acetate=0/1, 10/1) to afford the title compound (1 g, 2.69 mmol, 38.63% yield, 90% purity) as yellow oil.

$^1H$ NMR: (400 MHz, CHLOROFORM-d) δ ppm 7.43-7.30 (m, 5H), 5.11 (s, 2H), 4.25-4.14 (m, 2H), 2.50-2.35 (m, 2H), 2.29-2.14 (m, 4H), 1.95-1.84 (m, 2H), 1.29-1.20 (m, 3H), 1.06 (t, J=7.2 Hz, 3H), 0.78 (t, J=7.6 Hz, 3H).

Step 3. Synthesis of O5-benzyl O1-ethyl 2-(2-bromopropanoyl)-2-ethyl-pentanedioate To a solution of O5-benzyl O1-ethyl 2-ethyl-2-propanoyl-pentanedioate (0.4 g, 1.20 mmol, 1 eq) in $CHCl_3$ (5 mL) was added $Br_2$ (210.27 mg, 1.32 mmol, 67.83 uL, 1.1 eq) dropwise and the mixture was stirred at 20° C. for 2 h. It was quenched with sat. $NaHCO_3$ (20 mL), the aqueous phase was extracted with EtOAc (20 mL*3). The combined organic phase was dried over anhydrous $Na_2SO_4$, filtered and concentrated in vacuum to afford the title compound (0.5 g, crude) as yellow oil and it will be used directly in the next step.

Step 4. Synthesis of O5-benzyl O1-ethyl 2-(2-amino-5-methyl-thiazol-4-yl)-2-ethyl-pentanedioate A mixture of O5-benzyl O1-ethyl 2-(2-bromopropanoyl)-2-ethyl-pentanedioate (0.45 g, 1.09 mmol, 1 eq) and thiourea (82.88 mg, 1.09 mmol, 1 eq) in EtOH (5 mL) was stirred at 80° C. for 12 h. It was concentrated in vacuum. The residue was purified by silica gel chromatography (100-200 mesh silica gel, Petroleum ether/Ethyl acetate=10/1, 0/1, contained 5% MeOH) to afford the title compound (0.37 g, 540.08 umol, 49.60% yield, 57% purity) as yellow oil.

LCMS: $(M+H^+)$: 391.1 @1.102 min (5-95% ACN in $H_2O$, 2.0 min).

Step 5. Synthesis of O5-benzyl O1-ethyl 2-[2-(2,4-dichloroanilino)-5-methyl-thiazol-4-yl]-2-ethyl-pentanedioate To a solution of 2,4-dichloro-1-iodo-benzene (314.48 mg, 1.15 mmol, 1.5 eq) and O5-benzyl O1-ethyl 2-(2-amino-5-methylthiazol-4-yl)-2-ethyl-pentanedioate (0.3 g, 768.25 umol, 1 eq) in toluene (10 mL)/$H_2O$ (1 mL) was added $K_2CO_3$ (318.53 mg, 2.30 mmol, 3 eq), $Pd_2(dba)_3$ (70.35 mg, 76.83 umol, 0.1 eq) and Xantphos (88.91 mg, 153.65 umol, 0.2 eq). The mixture was purged with $N_2$ several time and stirred at 100° C. for 24 h. The residue was poured into water (15 mL). The aqueous phase was extracted with ethyl acetate (20 mL*3). The combined organic phase was washed with brine (15 mL*2), dried over anhydrous $Na_2SO_4$, filtered and concentrated in vacuum. The residue was purified by silica gel chromatography (100-200 mesh silica gel, Petroleum ether/Ethyl acetate=0/1, 5/1) to afford the title compound (0.18 g, 215.13 umol, 28.00% yield, 64% purity) as yellow oil.

LCMS: $(M+H^+)$: 535.1 @1.363 min (5-95% ACN in $H_2O$, 2.0 min).

Step 6. Synthesis of 4-[2-(2,4-dichloroanilino)-5-methyl-thiazol-4-yl]-4-ethoxycarbonyl-hexanoic acid (Cmp. 23)

To a solution of O5-benzyl O1-ethyl 2-[2-(2,4-dichloroanilino)-5-methyl-thiazol-4-yl]-2-ethyl-pentanedioate (0.15 g, 280.12 umol, 1 eq) in DCM (10 mL) was added $BBr_3$ (350.88 mg, 1.40 mmol, 134.96 uL, 5 eq) dropwise at 0° C., the mixture was stirred at 0° C. for 1 h. It was concentrated in vacuum. The residue was washed with a mixture of PE:EtOAc (5:1, 10 mL), yellow solid was formed and filtered to collect the cake. Then the cake was dissolved into ACN (3 mL) and the pH was adjusted to 9 with $NH_3.H_2O$ (30%). It was purified by prep-HPLC (neutral condition) to afford the title compound (47.5 mg, 100% purity) as colorless oil LCMS: $(M+H^+)$: 444.9@2.852 min (5-95% ACN in $H_2O$, 6.0 min).

$^1$H NMR: (400 MHz, METHANOL-d4) δ ppm 8.41 (d, J=8.9 Hz, 1H), 7.39 (d, J=2.4 Hz, 1H), 7.24 (dd, J=2.4, 8.9 Hz, 1H), 4.25-4.15 (m, 2H), 2.38-2.31 (m, 2H), 2.24-2.19 (m, 2H), 2.18 (s, 3H), 2.11 (quin, J=7.1 Hz, 2H), 1.26 (t, J=7.1 Hz, 3H), 0.85 (t, J=7.4 Hz, 3H).

Example 24. Synthesis of 4-[2-(2,4-dichloroanilino)-5-methyl-thiazol-4-yl]-4-ethyl-hexanoic acid (cmp. 24)

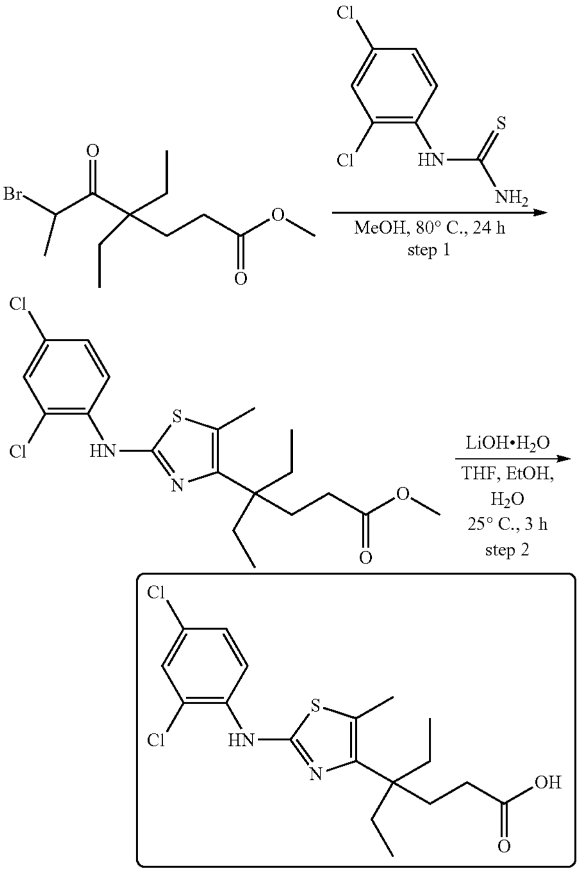

Cmp. 24

Step 1. Synthesis of methyl 4-[2-(2,4-dichloroanilino)-5-methyl-thiazol-4-yl]-4-ethyl-hexanoate To a solution of methyl 6-bromo-4,4-diethyl-5-oxo-heptanoate (400 mg, 1.36 mmol, 1 eq) in MeOH (4 mL) was added (2,4-dichlorophenyl)thiourea (331.81 mg, 1.50 mmol, 1.1 eq). The mixture was stirred at 80° C. for 24 h. After the completion of the reaction, it was concentrated. The residue was purified by MPLC ($SiO_2$, PE:EtOAc=5/1 to 1/1) to afford the title compound (150 mg, 234.73 umol, 17.21% yield, 65% purity) as yellow oil.

LCMS: $(M+H^+)$: 415.1@2.609 min (5-95% ACN in $H_2O$, 4.5 min).

Step 2. Synthesis of 4-[2-(2,4-dichloroanilino)-5-methyl-thiazol-4-yl]-4-ethyl-hexanoic acid (Cmp. 24)

To a solution of methyl 4-[2-(2,4-dichloroanilino)-5-methyl-thiazol-4-yl]-4-ethyl-hexanoate (150 mg, 361.12 umol, 1 eq) in THF (4 mL), EtOH (1 mL) and $H_2O$ (1 mL) was added $LiOH{\cdot}H_2O$ (45.46 mg, 1.08 mmol, 3 eq). The mixture was stirred at 25° C. for 3 h. After the completion of the reaction, it was poured into water (30 mL) and the pH was adjusted to 3 with aq. HCl (1M), extracted with EtOAc (30 mL*3). The combined organic layers were washed with brine (30 mL*3), dried over anhydrous $Na_2SO_4$ and concentrated. The residue was purified by MPLC ($SiO_2$, PE:EtOAc=5/1 to 1/1) to afford the title compound (11.6 mg, 28.66 umol, 7.94% yield, 99.17% purity) as yellow oil.

LCMS: $(M+H^+)$: 401.1/403.1@2.865 min (5-95% ACN in $H_2O$, 6 min).

$^1H$ NMR: (400 MHz, METHANOL-d4) δ ppm 8.40 (d, J=9.0 Hz, 1H), 7.39 (d, J=2.4 Hz, 1H), 7.23 (dd, J=2.5, 8.9 Hz, 1H), 2.38 (s, 3H), 2.22-1.97 (m, 4H), 1.81 (tdd, J=7.1, 14.3, 18.0 Hz, 4H), 0.80 (t, J=7.4 Hz, 6H).

Example 25. Synthesis of 4-[5-cyano-2-(2,4-difluoroanilino)thiazol-4-yl]-4-ethoxycarbonyl-hexanoic acid (Cmp. 25 (RS))

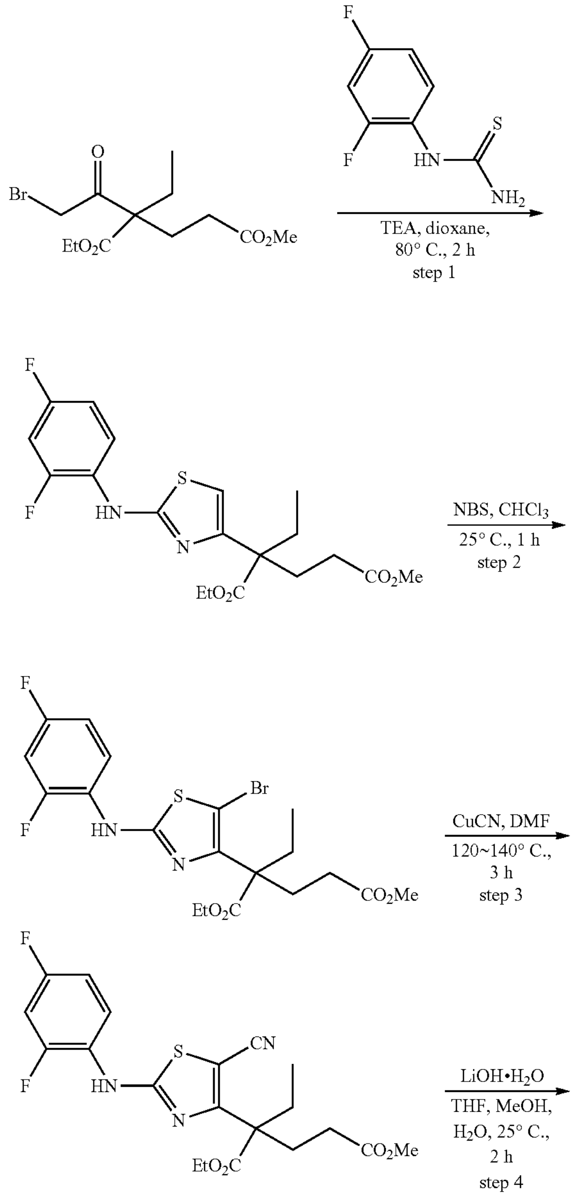

-continued

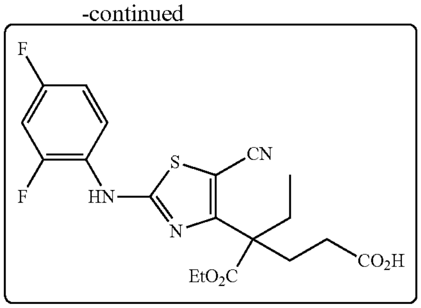

Cmp.

Step 1. Synthesis of O1-ethyl O5-methyl 2-[2-(2,4-difluoroanilino)thiazol-4-yl]-2-ethyl-pentanedioate To a solution of (2,4-difluorophenyl)thiourea (1.60 g, 8.51 mmol, 1.1 eq) and O1-ethyl O5-methyl 2-(2-bromoacetyl)-2-ethylpentanedioate (2.5 g, 7.74 mmol, 1 eq) in dioxane (30 mL) was added TEA (2.35 g, 23.21 mmol, 3.23 mL, 3 eq). The mixture was stirred at 80° C. for 2 h. The mixture was concentrated in vacuum. The residue was purified by silica gel chromatography (100-200 mesh silica gel, Petroleum ether/Ethyl acetate=10/1, 3/1) to afford the title compound (2 g, 80% purity) as yellow oil Step 2. Synthesis of O1-ethyl O5-methyl 2-[5-bromo-2-(2,4-difluoroanilino)thiazol-4-yl]-2-ethyl-pentanedioate To a solution of O1-ethyl O5-methyl 2-[2-(2,4-difluoroanilino)thiazol-4-yl]-2-ethyl-pentanedioate (1.9 g, 4.61 mmol, 1 eq) in $CHCl_3$ (2 mL) was added NBS (901.89 mg, 5.07 mmol, 1.1 eq) and the mixture was stirred at 25° C. for 1 h. The residue was poured into water (20 mL). The aqueous phase was extracted with DCM (20 mL*2). The combined organic phase was dried over anhydrous $Na_2SO_4$, filtered and concentrated in vacuum. The residue was purified by silica gel chromatography (100-200 mesh silica gel, Petroleum ether/Ethyl acetate=20/1, 5/1) to afford the title compound (1 g, 1.42 mmol, 30.93% yield, 70% purity) as yellow oil.

Step 3. Synthesis of O1-ethyl O5-methyl 2-[5-cyano-2-(2,4-difluoroanilino)thiazol-4-yl]-2-ethyl-pentanedioate To a solution of O1-ethyl O5-methyl 2-[5-bromo-2-(2,4-difluoroanilino)thiazol-4-yl]-2-ethyl-pentanedioate (0.3 g, 610.57 umol, 1 eq, Reactant 1) in DMF (5 mL) was added CuCN (109.37 mg, 1.22 mmol, 266.75 uL, 2 eq) and the mixture was stirred at 120° C. for 1 h. LCMS showed Reactant 1 was remained and trace desired compound was detected. Then the mixture was heated to 140° C. for 2 h. After completion of the reaction, the residue was cooled to 25° C. and poured into EDTA disodium solution (30 mL, 5%) and stirred for 5 min. The aqueous phase was extracted with ethyl acetate (20 mL*3). The combined organic phase was washed with brine (30 mL*2), dried over anhydrous $Na_2SO_4$, filtered and concentrated in vacuum. The residue was purified by silica gel chromatography (Petroleum ether/Ethyl acetate=10/1, 0/1) to afford the title compound (30 mg, 85% purity) as yellow oil.

LCMS: $(M+H^+)$: 438.1@1.206 min (5-95% ACN in $H_2O$, 2.0 min).

Step 4. Synthesis of 4-[5-cyano-2-(2,4-difluoroanilino)thiazol-4-yl]-4-ethoxycarbonyl-hexanoic acid (Cmp. 25)

To a solution of O1-ethyl O5-methyl 2-[5-cyano-2-(2,4-difluoroanilino)thiazol-4-yl]-2-ethyl-pentanedioate (30 mg, 68.58 umol, 1 eq) in THF (1 mL)/MeOH (0.5 mL)/$H_2O$ (0.5 mL) was added LiOH·$H_2O$ (14.39 mg, 342.89 umol, 5 eq). The mixture was stirred at 25° C. for 2 h. It was poured into water (10 mL). The aqueous phase was extracted with ethyl acetate (10 mL*2). The combined organic phase was discarded. The aqueous phase pH was adjusted to 5 with aqueous HCl (1 N), extracted with ethyl acetate (10 mL*2). The combined organic phase was dried over anhydrous $Na_2SO_4$, filtered and concentrated in vacuum. The residue was purified by prep-HPLC (FA condition) to afford the title compound (9 mg, 19.17 umol, 27.96% yield, 100% purity, as a FA salt) as yellow solid.

LCMS: $(M+H^+)$: 424.0@2.527 min (5-95% ACN in $H_2O$, 6.0 min).

$^1H$ NMR: (400 MHz, METHANOL-d4) δ ppm 8.22 (dt, J=5.9, 9.2 Hz, 1H), 7.07 (ddd, J=2.8, 8.5, 11.3 Hz, 1H), 7.01-6.94 (m, 1H), 4.28-4.17 (m, 2H), 2.44-2.38 (m, 2H), 2.30-2.08 (m, 4H), 1.27 (t, J=7.1 Hz, 3H), 0.88 (t, J=7.4 Hz, 3H).

Example 26. Synthesis of 4-[6-[(3,5-difluoro-2-pyridyl)amino]pyrazin-2-yl]-4-ethyl-hexanoic acid (Cmp. 26)

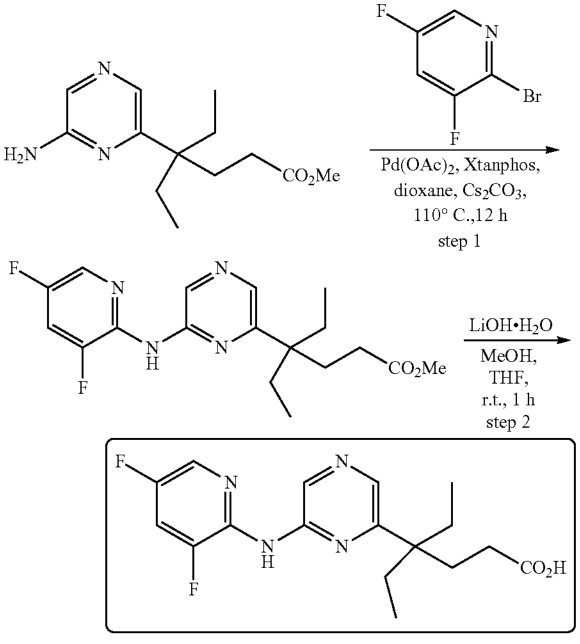

Cmp. 26

Step 1. Synthesis of methyl 4-[6-[(3,5-difluoro-2-pyridyl)amino]pyrazin-2-yl]-4-ethyl-hexanoate To a solution of methyl 4-(6-aminopyrazin-2-yl)-4-ethyl-hexanoate (100 mg, 397.89 umol, 1 eq) in dioxane (2 mL) was added 2-bromo-3,5-difluoro-pyridine (92.62 mg, 477.47 umol, 1.2 eq), Xantphos (34.53 mg, 59.68 umol, 0.15 eq), $Pd_2(dba)_3$ (36.44 mg, 39.79 umol, 0.1 eq), and $Cs_2CO_3$ (259.28 mg, 795.79 umol, 2 eq). The mixture was stirred at 110° C. for 12 h under $N_2$. After the completion of the reaction, it was poured into water (30 mL), extracted with EtOAc (30 mL*3). The combined organic layers were washed with brine (30 mL*3), dried over anhydrous $Na_2SO_4$ and concentrated. The residue was purified by MPLC ($SiO_2$, PE:EtOAc=5/1 to 1/1) to afford the title compound (100 mg, 200.34 umol, 50.35% yield, 73% purity) as yellow oil.

LCMS: $(M+H^+)$: 365.1@2.849 min (10-80% ACN in $H_2O$, 4.5 min).

Step 2. Synthesis of 4-[6-[(3,5-difluoro-2-pyridyl)amino]pyrazin-2-yl]-4-ethyl-hexanoic acid (Cmp. 26)

To a solution of methyl 4-[6-[(3,5-difluoro-2-pyridyl)amino]pyrazin-2-yl]-4-ethyl-hexanoate (60 mg, 164.66 umol, 1 eq) in THF (1.2 mL), MeOH (0.3 mL) and $H_2O$ (0.3 mL) was added LiOH·$H_2O$ (13.82 mg, 329.32 umol, 2 eq). The mixture was stirred at 25° C. for 1 h. After the completion of the reaction, it was poured into water (30 mL) and the pH was adjusted to 2 with aqueous HCl (1M), extracted with EtOAc(10 mL*3). The combined organic layers were washed with brine (10 mL*3), dried over anhydrous $Na_2SO_4$ and concentrated. The residue was purified by prep-HPLC (HCl condition) to afford the title compound (20.2 mg, 100% purity, HCl) as yellow solid.

LCMS: $(M+H^+)$: 351.1@2.370 min (5-95% ACN in $H_2O$, 6 min).

$^1H$ NMR: (400 MHz, METHANOL-d4) δ ppm 9.22 (s, 1H), 8.27 (s, 1H), 8.19 (d, J=2.4 Hz, 1H), 7.78-7.66 (m, 1H), 2.14 (s, 4H), 1.92-1.81 (m, 4H), 0.77 (t, J=7.4 Hz, 6H).

Example 27. Synthesis of 4-[5-chloro-2-(2-chloroanilino) thiazol-4-yl]-4-ethoxycarbonyl-hexanoic acid (Cmp. 27 (RS))

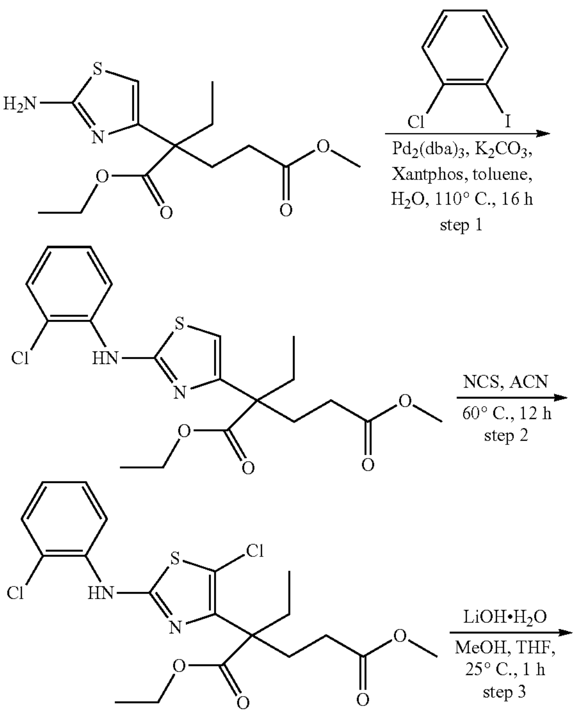

-continued

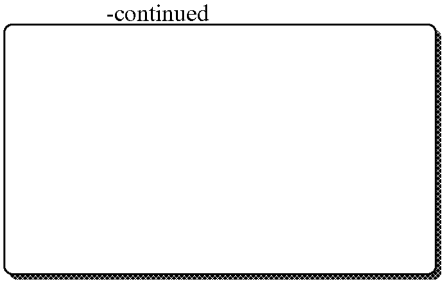

Cmp.27

Step 1. Synthesis of O1-ethyl O5-methyl 2-[2-(2-chloroanilino)thiazol-4-yl]-2-ethyl-pentanedioate To a solution of O1-ethyl O5-methyl 2-(2-aminothiazol-4-yl)-2-ethyl-pentanedioate (0.35 g, 1.17 mmol, 1 eq) and 1-chloro-2-iodo-benzene (361.20 mg, 1.51 mmol, 1.3 eq) in toluene (5 mL)/$H_2O$ (0.5 mL) was added $Pd_2(dba)_3$ (53.35 mg, 58.26 umol, 0.05 eq), Xantphos (67.42 mg, 116.52 umol, 0.1 eq) and $K_2CO_3$ (322.08 mg, 2.33 mmol, 2 eq). The mixture was stirred at 110° C. for 16 h. The resulting mixture was poured into water (30 mL) and then extracted with ethyl acetate (30 mL*3). The combined organic phase was washed with brine (50 mL*2), dried over anhydrous $Na_2SO_4$, filtered and concentrated in vacuum. The residue was purified by silica gel chromatography (Petroleum ether/Ethyl acetate=0/1, 10/1) to afford the title compound (0.35 g, 681.41 umol, 58.48% yield, 80% purity) as yellow oil.

$^1H$ NMR: (400 MHz, CHLOROFORM-) δ ppm 8.18 (d, J=8.3 Hz, 1H), 7.51 (s, 1H), 7.38 (d, J=8.0 Hz, 1H), 6.95 (t, J=7.7 Hz, 1H), 6.64 (s, 1H), 4.21 (q, J=7.1 Hz, 2H), 3.65 (s, 3H), 2.47-2.33 (m, 2H), 2.25-2.14 (m, 2H), 2.14-2.07 (m, 1H), 2.05-1.99 (m, 1H), 1.31-1.25 (m, 3H), 0.82 (t, J=7.4 Hz, 3H).

Step 2. Synthesis of O1-ethyl O5-methyl 2-[5-chloro-2-(2-chloroanilino)thiazol-4-yl]-2-ethyl-pentanedioate A mixture of O1-ethyl O5-methyl 2-[2-(2-chloroanilino) thiazol-4-yl]-2-ethyl-pentanedioate (0.15 g, 365.04 umol, 1 eq) and NCS (53.62 mg, 401.54 umol, 1.1 eq) in ACN (8 mL) was stirred 60° C. for 12 h. It was concentrated in vacuum. The residue was purified by silica gel chromatography (100-200 mesh silica gel, Petroleum ether/Ethyl acetate=0/1, 5/1) to afford the title compound (0.15 g, 336.81 umol, 92.27% yield) as yellow oil.

Step 3. Synthesis of 4-[5-chloro-2-(2-chloroanilino) thiazol-4-yl]-4-ethoxycarbonyl-hexanoic acid (Cmp. 27)

To a solution of O1-ethyl O5-methyl 2-[5-chloro-2-(2-chloroanilino) thiazol-4-yl]-2-ethyl-pentanedioate (0.15 g, 336.81 umol, 1 eq) in THF (5 mL)/MeOH (1 mL)/$H_2O$ (1 mL) was added $LiOH{\cdot}H_2O$ (70.67 mg, 1.68 mmol, 5 eq). The mixture was stirred at 25° C. for 1 h. The pH of the reaction mixture was adjusted to 5 by aqueous HCl (1 N), extracted with ethyl acetate (20 mL*2). The combined organic phase was dried over anhydrous $Na_2SO_4$, filtered and concentrated in vacuum. The residue was purified by prep-HPLC (HCl condition) to afford the title compound (101.1 mg, 100% purity, as a HCl salt) as white solid.

LCMS: ($M+H^+$): 431.1/433.0@2.751 min (5-95% ACN in $H_2O$, 6.0 min).

$^1H$ NMR: (400 MHz, METHANOL-d4) δ ppm 8.30 (dd, J=1.3, 8.3 Hz, 1H), 7.39 (dd, J=1.4, 8.0 Hz, 1H), 7.30-7.21 (m, 1H), 6.99 (dt, J=1.4, 7.7 Hz, 1H), 4.20 (ttd, J=3.5, 7.1, 10.6 Hz, 2H), 2.43-2.32 (m, 2H), 2.29-2.15 (m, 3H), 2.12-1.99 (m, 1H), 1.26 (t, J=7.1 Hz, 3H), 0.86 (t, J=7.5 Hz, 3H).

Example 28. Synthesis of 4-[6-(2-chloroanilino) pyrazin-2-yl]-4-ethyl-hexanoic acid (Cmp. 28)

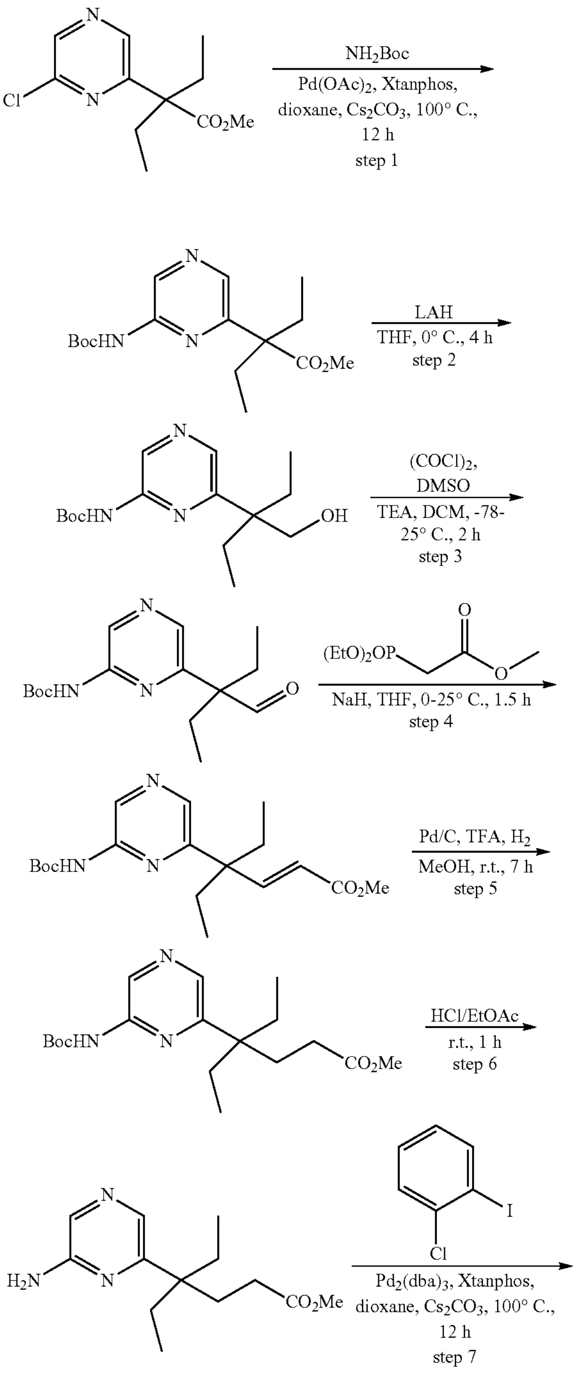

-continued

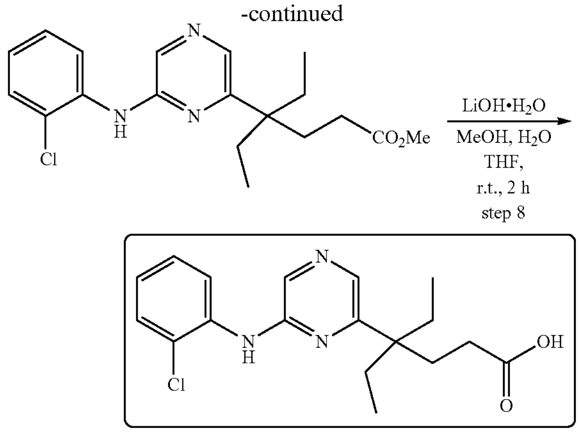

Cmp.28

Step 1. Synthesis of methyl 2-[6-(tert-butoxycarbonylamino)pyrazin-2-yl]-2-ethyl-butanoate To a solution of methyl 2-(6-chloropyrazin-2-yl)-2-ethylbutanoate (16 g, 65.92 mmol, 1 eq) in dioxane (160 mL) was added $NH_2Boc$ (11.58 g, 98.89 mmol, 1.5 eq), Xantphos (7.63 g, 13.18 mmol, 0.2 eq), $Cs_2CO_3$ (42.96 g, 131.85 mmol, 2 eq) and $Pd(OAc)_2$ (1.48 g, 6.59 mmol, 0.1 eq). The mixture was stirred at 100° C. for 12 h under $N_2$. After the completion of the reaction, it was cooled to the room temperature and poured into water (300 mL), extracted with EtOAc (100 mL*3). The combined organic layers were washed with brine (100 mL*3), dried over anhydrous $Na_2SO_4$ and concentrated to afford a residue. The residue was purified by MPLC ($SiO_2$, PE:EtOAc=5/1 to 1/1) to afford the title compound (14.3 g, 40.24 mmol, 61.04% yield, 91% purity) as yellow solid.

Step 2. Synthesis of tert-butyl N-[6-[1-ethyl-1-(hydroxymethyl)propyl]pyrazin-2-yl]carbamate To a solution of methyl 2-[6-(tert-butoxycarbonylamino) pyrazin-2-yl]-2-ethyl-butanoate (14.3 g, 44.22 mmol, 1 eq) in THF (140 mL) was added LAH (2.01 g, 53.06 mmol, 1.2 eq) at 0° C. The mixture was stirred at 0° C. for 4 h under $N_2$. After the completion of the reaction, it was quenched by addition Sat. $NH_4Cl$ solution (100 mL), and aqueous HCl (20 mL, 1M), extracted with EtOAc (100 mL*3). The combined organic layers were washed with brine (100 mL*3), dried over anhydrous $Na_2SO_4$ and concentrated to afford a residue. The residue was purified by MPLC ($SiO_2$, PE:EtOAc=5/1 to 1/1) to afford the title compound (7.9 g, 25.14 mmol, 56.85% yield, 94% purity) as white solid.

Step 3. Synthesis of tert-butyl N-[6-(1-ethyl-1-formyl-propyl)pyrazin-2-yl]carbamate To a solution of $(COCl)_2$ (6.79 g, 53.49 mmol, 4.68 mL, 2 eq) in DCM (60 mL) was added DMSO (4.18 g, 53.49 mmol, 4.18 mL, 2 eq) at −78° C. The mixture was stirred at −78° C. for 0.5 h. Then tert-butyl N-[6-[1-ethyl-1-hydroxymethyl)propyl]pyrazin-2-yl]carbamate (7.9 g, 26.75 mmol, 1 eq) in DCM (20 mL) was added. The mixture was stirred at −78° C. for 1 h. Then TEA (13.53 g, 133.73 mmol, 18.61 mL, 5 eq) was added at −78° C. and the mixture was warmed to 25° C. over 30 min. TLC indicated completion of the reaction. The solution was poured into saturated $NaHCO_3$ (100 mL), extracted with EtOAc (100 mL*3). The combined organic layers were washed with brine (100 mL*3), dried over anhydrous $Na_2SO_4$ and concentrated to afford a residue. The residue was purified by MPLC ($SiO_2$, PE:EtOAc=5/1 to 1/1) to afford the title compound (5.5 g, 14.81 mmol, 55.38% yield, 79% purity) as white solid.

Step 4. Synthesis of methyl (E)-4-[6-(tert-butoxycarbonylamino)pyrazin-2-yl]-4-ethyl-hex-2-enoate To a solution of methyl 2-diethoxyphosphorylacetate (4.73 g, 22.50 mmol, 1.2 eq) in THF (60 mL) was added NaH (1.12 g, 28.12 mmol, 60% purity, 1.5 eq) at 0° C. The mixture was stirred at 0° C. for 0.5 h. Then tert-butyl N-[6-(1-ethyl-1-formyl-propyl) pyrazin-2-yl]carbamate (5.5 g, 18.75 mmol, 1 eq) was added at 0° C. It was stirred at 25° C. for 1 h. After the completion of the reaction, it was poured into water (50 mL), extracted with EtOAc (40 mL*3). The combined organic layers were washed with brine (40 mL*3), dried over anhydrous $Na_2SO_4$ and concentrated to afford a residue. The residue was purified by MPLC ($SiO_2$, PE:EtOAc=5/1 to 1/1) to afford the title compound (5.5 g, 13.99 mmol, 74.64% yield, 88.9% purity) as yellow oil.

LCMS: ($M+H^+$): 350.3@2.237 min (5-95% ACN in $H_2O$, 4.5 min).

Step 5. Synthesis of methyl 4-[6-(tert-butoxycarbonylamino)pyrazin-2-yl]-4-ethyl-hexanoate To a solution of methyl (E)-4-[6-(tert-butoxycarbonylamino)pyrazin-2-yl]-4-ethyl-hex-2-enoate (2.5 g, 7.15 mmol, 1 eq) in MeOH (20 mL) was added Pd/C (2 g, 10% purity) and TFA (1.22 g, 10.73 mmol, 794.60 uL, 1.5 eq) under $N_2$. The suspension was degassed under vacuum and purged with $H_2$ several times. The mixture was stirred at 25° C. for 7 h under $H_2$ (15 psi). After the completion of the reaction, it was filtered and the filtrate was concentrated to afford the title compound (6 g, crude) as yellow oil and used directly next step.

Step 6. Synthesis of methyl 4-(6-aminopyrazin-2-yl)-4-ethyl-hexanoate

To a solution of methyl 4-[6-(tert-butoxycarbonylamino) pyrazin-2-yl]-4-ethyl-hexanoate (6 g, 17.07 mmol, 1 eq) in EtOAc (10 mL) was added HCl/EtOAc (4M, 40 mL). The mixture was stirred at 25° C. for 1 h. After the completion of the reaction, it was concentrated. The residue was purified reversed-phase HPLC (0.1% TFA condition). The pH of the solution was adjusted to 9 with saturated $NaHCO_3$, extracted with EtOAc (150 mL*3). The combined organic layers were washed with brine (150 mL*3), dried over anhydrous $Na_2SO_4$ and concentrated under vacuum to afford the title compound (2.6 g, 8.79 mmol, 51.51% yield, 85% purity) as yellow solid.

$^1H$ NMR: (400 MHz, CHLOROFORM-d) δ ppm 7.88 (s, 1H), 7.78 (s, 1H), 3.63 (s, 3H), 2.08-2.00 (m, 4H), 1.73 (tdd, J=7.1, 14.5, 17.6 Hz, 4H), 0.70 (t, J=7.5 Hz, 6H).

Step 7. Synthesis of methyl 4-[6-(2-chloroanilino) pyrazin-2-yl]-4-ethyl-hexanoate To a solution of methyl 4-(6-aminopyrazin-2-yl)-4-ethylhexanoate (0.15 g, 596.84 umol, 1 eq) in dioxane (2 mL) was added 1-chloro-2-iodo-benzene (170.78 mg, 716.21 umol, 1.2 eq), Xantphos (51.80 mg, 89.53 umol, 0.15 eq), $Pd_2(dba)_3$ (54.65 mg, 59.68 umol, 0.1 eq) and $Cs_2CO_3$ (388.92 mg, 1.19 mmol, 2 eq). The suspension was degassed under vacuum and purged with $N_2$ several times. The mixture was stirred at 100° C. for 12 h under $N_2$. After the completion of the reaction, it was cooled to the room temperature and poured into water (20 mL), extracted with EtOAc (20 mL*3). The combined organic layers were washed with brine (20 mL*3), dried over anhydrous $Na_2SO_4$ and concentrated to afford a residue. The residue was purified by MPLC ($SiO_2$, PE:EtOAc=5/1 to 1/1) to afford the title compound (150 mg) as brown oil.

LCMS: (M+H$^+$): 362.2@2.199 min (5-95% ACN in $H_2O$, 4.5 min).

Step 8. Synthesis of 4-[6-(2-chloroanilino)pyrazin-2-yl]-4-ethyl-hexanoic acid (Cmp. 28)

To a solution of methyl 4-[6-(2-chloroanilino)pyrazin-2-yl]-4-ethyl-hexanoate (150 mg, 414.52 umol, 1 eq) in THF (2 mL), MeOH (0.5 mL) and $H_2O$ (0.5 mL) was added $LiOH{\cdot}H_2O$ (52.18 mg, 1.24 mmol, 3 eq). The mixture was stirred at 25° C. for 2 h. After the completion of the reaction, it was poured into water (10 mL) and pH was adjusted to 3 with aqueous HCl (1M), extracted with EtOAc (10 mL*3). The combined organic layers were washed with brine (10 mL*3), dried over anhydrous $Na_2SO_4$ and concentrated to afford a residue. The residue was purified by prep-HPLC (HCl condition) to afford the title compound (48.3 mg, 125.68 umol, 30.32% yield, 100% purity, HCl salt) was as yellow solid.

LCMS: (M+H$^+$): 348.1@2.529 min (5-95% ACN in $H_2O$, 6 min).

$^1$H NMR: (400 MHz, METHANOL-d4) δ ppm 8.15-8.04 (m, 2H), 7.95 (s, 1H), 7.46 (d, J=7.9 Hz, 1H), 7.31 (t, J=7.8 Hz, 1H), 7.10 (t, J=7.7 Hz, 1H), 2.07 (s, 4H), 1.86-1.67 (m, 4H), 0.74 (t, J=7.4 Hz, 6H).

Example 29. Synthesis of 4-Ethyl-4-[6-(2,4,5-Trifluoroanilino)Pyrazin-2-yl]Hexanoic Acid (Cmp. 29)

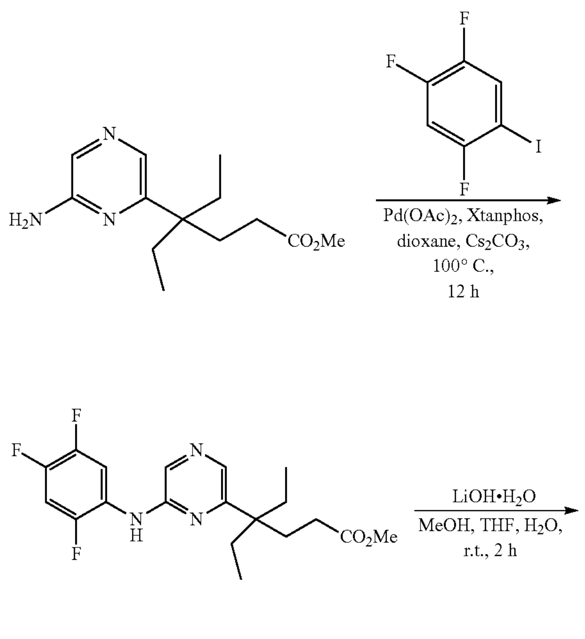

-continued

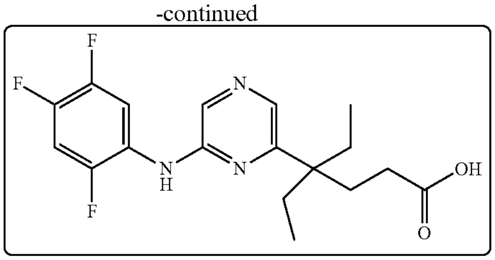

Cmp. 29

Step 1. Synthesis of methyl 4-ethyl-4-[6-(2,4,5-trifluoroanilino)pyrazin-2-yl]hexanoate To a solution of methyl 4-(6-aminopyrazin-2-yl)-4-ethyl-hexanoate (0.15 g, 596.84 umol, 1 eq) in dioxane (2 mL) was added 1,2,4-trifluoro-5-iodo-benzene (184.77 mg, 716.21 umol, 1.2 eq), Xantphos (51.80 mg, 89.53 umol, 0.15 eq), $Pd_2(dba)_3$ (54.65 mg, 59.68 umol, 0.1 eq) and $Cs_2CO_3$ (388.92 mg, 1.19 mmol, 2 eq). The suspension was degassed under vacuum and purged with $N_2$ several times. The mixture was stirred at 100° C. for 12 h under $N_2$. After the completion of the reaction, it was poured into water (10 mL), extracted with EtOAc (10 mL*3). The combined organic layers were washed with brine (10 mL*3), dried over anhydrous $Na_2SO_4$ and concentrated to afford a residue. The residue was purified by MPLC ($SiO_2$, PE:EtOAc=5/1 to 1/1) to afford the title compound (150 mg, 369.70 umol, 61.94% yield, 94% purity) as brown oil.

LCMS: (M+H$^+$): 538.2@2.130 min (5-95% ACN in $H_2O$, 4.5 min).

Step 2. Synthesis of 4-ethyl-4-[6-(2,4,5-trifluoroanilino)pyrazin-2-yl]hexanoic acid (Cmp. 29)

To a solution of methyl 4-ethyl-4-[6-(2,4,5-trifluoroanilino)pyrazin-2-yl]hexanoate (120 mg, 314.64 umol, 1 eq) in MeOH (0.5 mL), THF (2 mL) and $H_2O$ (0.5 mL) was added $LiOH{\cdot}H_2O$ (39.61 mg, 943.91 umol, 3 eq). The mixture was stirred at 25° C. for 2 h. After the completion of the reaction, it was poured into water (30 mL) and the pH was adjusted to 3 with aqeuous HCl (1M), extracted with EtOAc (30 mL*3). The combined organic layers were washed with brine (30 mL*3), dried over anhydrous $Na_2SO_4$ and concentrated to afford a residue. The residue was purified by prep-HPLC (HCl condition) to afford the title compound (36 mg, 97.4% purity, HCl salt) as yellow solid.

LCMS: (M+H$^+$): 368.2@3.540 min (5-95% ACN in $H_2O$, 6 min).

$^1$H NMR: (400 MHz, METHANOL-d4) δ ppm 8.36 (td, J=8.0, 13.0 Hz, 1H), 8.13 (s, 1H), 7.99 (s, 1H), 7.24 (dt, J=7.3, 10.6 Hz, 1H), 2.17-2.01 (m, 4H), 1.90-1.76 (m, 4H), 0.76 (t, J=7.4 Hz, 6H).

Example 30. Additional Compounds of the Disclosure

Additional compounds of the disclosure are prepared via the methods demonstrated in examples 1-29 using ariations in starting materials and reaction conditions that are readily apparent to those in the art of organic chemistry synthesis.

TABLE 1
| Cmp. No. | Structure | Name |
|---|---|---|
| 30 | 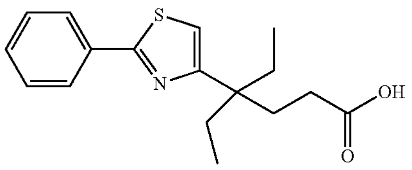 [SMILES: CCC(CC)(CCC(=O)O)c1csc(-c2ccccc2)n1] | 4-ethyl-4-(2-phenylthiazol-4-yl)hexanoic acid |
| 31 | 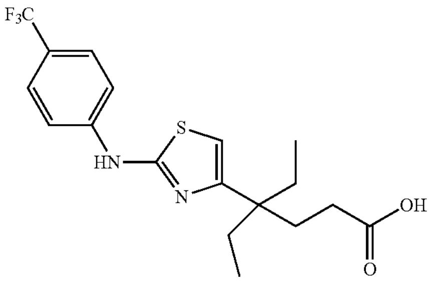 [SMILES: CCC(CC)(CCC(=O)O)c1csc(Nc2ccc(C(F)(F)F)cc2)n1] | 4-ethyl-4-(2-((4-(trifluoromethyl)phenyl)amino)thiazol-4-yl)hexanoic acid |
| 32 | 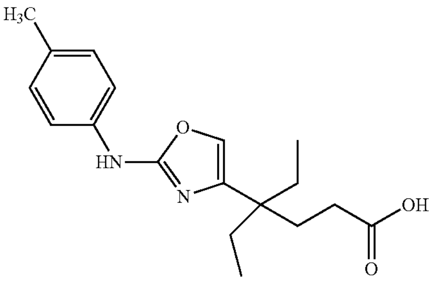 [SMILES: CCC(CC)(CCC(=O)O)c1coc(Nc2ccc(C)cc2)n1] | 4-ethyl-4-(2-(p-tolylamino)oxazol-4-yl)hexanoic acid |
| 33 | 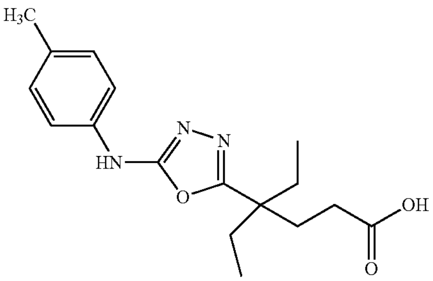 [SMILES: CCC(CC)(CCC(=O)O)c1nnc(Nc2ccc(C)cc2)o1] | 4-ethyl-4-(5-(p-tolylamino)-1,3,4-oxadiazol-2-yl)hexanoic acid |
| 34 (RS) | 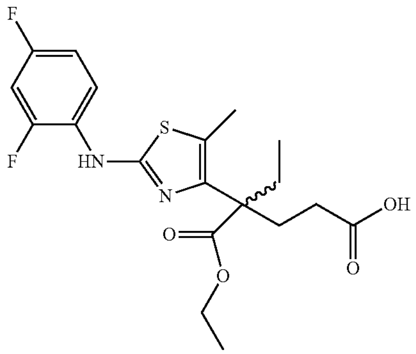 [SMILES: CCOC(=O)C(CC)(CCC(=O)O)c1nc(Nc2ccc(F)cc2F)sc1C] | 4-(2-((2,4-difluorophenyl)amino)-5-methylthiazol-4-yl)-4-(ethoxycarbonyl)hexanoic acid |

TABLE 1-continued

| Cmp. No. | Structure | Name |
| --- | --- | --- |
| 35 (RS) | 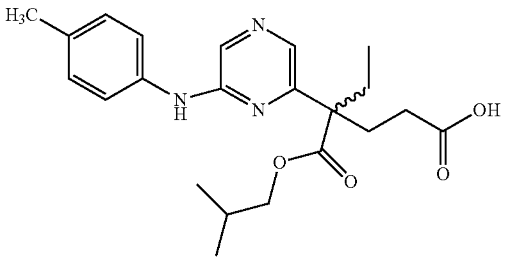 [SMILES: CCC(CCC(=O)O)(C(=O)OCC(C)C)c1cncc(Nc2ccc(C)cc2)n1] | 4-(isobutoxycarbonyl)-4-(6-(p-tolylamino)pyrazin-2-yl)hexanoic acid |
| 36 (RS) | 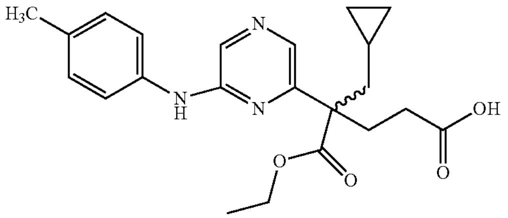 [SMILES: CCOC(=O)C(CCC(=O)O)(CC1CC1)c1cncc(Nc2ccc(C)cc2)n1] | 4-(cyclopropylmethyl)-5-ethoxy-5-oxo-4-(6-(p-tolylamino)pyrazin-2-yl)pentanoic acid |
| 37 (RS) | 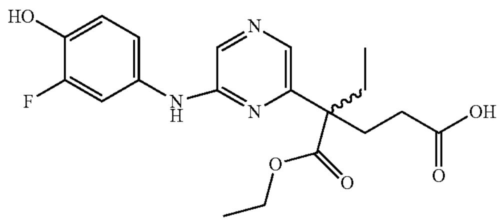 [SMILES: CCOC(=O)C(CC)(CCC(=O)O)c1cncc(Nc2ccc(O)c(F)c2)n1] | 4-(ethoxycarbonyl)-4-(6-((3-fluoro-4-hydroxyphenyl)amino)pyrazin-2-yl)hexanoic acid |
| 38 (RS) | 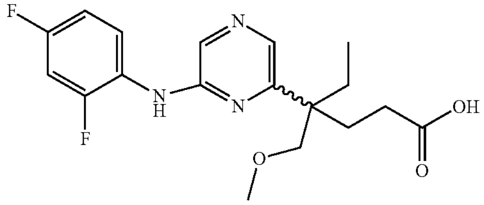 [SMILES: CCC(CCC(=O)O)(COC)c1cncc(Nc2ccc(F)cc2F)n1] | 4-(6-((2,4-difluorophenyl)amino)pyrazin-2-yl)-4-(methoxymethyl)hexanoic acid |
| 39 (RS) | 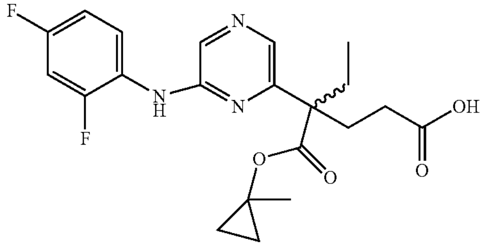 [SMILES: CCC(CCC(=O)O)(C(=O)OC1(C)CC1)c1cncc(Nc2ccc(F)cc2F)n1] | 4-(6-((2,4-difluorophenyl) amino)pyrazin-2-yl)-4-((1-methylcyclopropoxy)carbonyl)hexanoic acid |
| 40 (RS) | 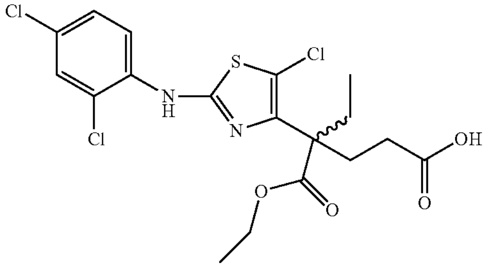 [SMILES: CCOC(=O)C(CC)(CCC(=O)O)c1nc(Nc2ccc(Cl)cc2Cl)sc1Cl] | 4-(5-chloro-2-((2,4-dichlorophenyl)amino)thiazol-4-yl)-4-(ethoxycarbonyl)hexanoic acid |

Example 31. PGT Inhibitory Properties of Compounds

MDCK cells stably transfected with rat PGT ae seeded at 15-20% confluence on 96-well deepwell plates. The day on which the cells are seeded is considered day 1. PGE2 uptake experiments are conducted on day 4. All of the PGE2 uptake experiments are conducted at room temperature. On day 4, cells are washed twice with Waymouth buffer (135 mM NaCl, 13 mM H-Hepes, 13 mM Na-Hepes, 2.5 mM $CaCl_2$, 1.2 mM $MgCl_2$, 0.8 mM $MgSO_4$, 5 mM KCl, and 28 mM D-glucose). Then 200 μL of Waymouth buffer containing [$^3$H]PGE2 (available from Perkin Elmer) is added to each well. At the designed time, the uptake of [$^3$H]PGE2 is stopped by aspiration of uptake buffer; followed by immediate washing twice with 500 μL of chilled Waymouth buffer. Cells are then lysed with 100 μL lysis buffer containing 0.25% SDS and 0.05 N NaOH. 1.5 mL of scintillation solution is added to each well, and intracellular [$^3$H] PGE2 is counted via a Beta Counter.

For preliminary testing of the compounds, 20 μL of Waymouth buffer containing the compound is added to each well; this was immediately followed by the addition of 180 μL of Waymouth buffer containing [$^3$H]PGE2. In each well, the total volume of uptake medium is 200 μL. Test compounds are first dissolved in organic solvent, such as EtOH, and then diluted in Waymouth buffer. The percent inhibition of [$^3$H]PGE2 uptake by compounds is calculated as [(uptakevehicle−uptakeinhibitor)÷(uptakevehicle)]×100.

To determine IC50 of each compound, Waymouth buffer containing various concentrations of the compound is added to each well; immediately followed by the addition of 180 μL of Waymouth buffer containing [$^3$H]PGE2. IC50 was calculated by fitting the following equation.

$$y=m1-m1*(m0/(m2+m0)).$$

Results for certain exemplified compounds are presented in Table 2. * indicates an IC50 of <100 μM, <20 μM, *<10 μM, and ****<1 μM.

TABLE 2

| Cmp. No. | Activity |
|---|---|
| 1 | **** |
| 2 | * |
| 3 | ** |
| 5 | *** |
| 6 | *** |
| 7 | *** |
| 8 | *** |
| 9 | *** |
| 10 | **** |
| 11 | **** |
| 13 | *** |
| 14a | **** |
| 14b | **** |
| 17 | **** |
| 18 | **** |
| 19 | **** |
| 20 | **** |
| 21 | **** |
| 22b | **** |
| 23 | **** |
| 24 | **** |
| 27 (RS) | **** |
| 27 (enantiomer 1) | **** |
| 27 (enantiomer 2) | **** |
| 28 | **** |
| 29 | **** |
| 30 | *** |
| 31 | ** |

TABLE 2-continued

| Cmp. No. | Activity |
|---|---|
| 32 | * |
| 33 | *** |
| 34 | *** |
| 35 | *** |
| 36 | *** |
| 37 | **** |
| 38 | *** |
| 39 | **** |
| 40 | **** |

What is claimed is:

1. A compound of Formula 1:

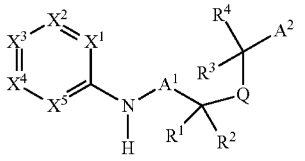

(1)

or a pharmaceutically acceptable salt thereof, wherein:

$R^1$ and $R^2$ are independently chosen from $C_1$-$C_6$alkyl, ($C_1$-$C_4$alkoxy) ($C_1$-$C_4$alkyl), ($C_3$-$C_7$cycloalkyl)$C_0$-$C_2$alkyl, —$CO_2C_1$-$C_6$alkyl, and —$CO_2C_0$-$C_2$alkyl($C_3$-$C_7$cycloalkyl), or $R^1$ and $R^2$ together may be a 3-6 membered carbocyclic ring or a 4-6-membered heterocycloalkyl ring containing one heteroatom or substituted heteroatom chosen from NH, N—$C_1$-$C_6$alkyl, NCO—$C_1$-$C_6$-alkyl, $NCO_2$—$C_1$-$C_6$-alkyl, $NSO_2$—$C_1$-$C_6$-alkyl, O, S and $SO_2$;

$R^3$ and $R^4$ are independently chosen from hydrogen, fluoro, and methyl or $R^3$ and $R^4$ can be taken together to form a $C_3$-$C_5$ saturated or partially unsaturated carbocyclic ring or an oxetanyl ring which is optionally 2,2 or 3,3 disubstituted with halogen or $C_1$-$C_2$alkyl;

$A^1$ is a pyrazinyl or pyrimidinyl heteroarylene group optionally substituted with one or more substituents independently chosen from halogen, hydroxyl, cyano, $C_1$-$C_6$-alkyl, $C_1$-$C_6$alkoxy, ($C_3$-$C_7$-cycloalkyl) $C_0$-$C_2$alkyl, $C_1$-$C_2$haloalkyl, and $C_1$-$C_2$haloalkoxy;

$A^2$ is —$CO_2H$;

$X^1$, $X^2$, $X^3$, $X^4$, and $X^5$ are aromatic ring atoms chosen from N and C, where up to 3 of $X^1$, $X^2$, $X^3$, $X^4$, and $X^5$ are N ring atoms and each C ring atom is optionally substituted with $R^6$ where each $R^6$ is independently chosen from halogen, hydroxyl, cyano, amino, —$CONH_2$, $C_1$-$C_6$alkyl, $C_1$-$C_6$alkoxy, $C_1$-$C_2$haloalkyl, $C_1$-$C_2$haloalkoxy, mono- or di-($C_1$-$C_6$alkylamino) $C_0$-$C_2$alkyl, ($C_3$-$C_7$cycloalkyl) $C_0$-$C_2$alkyl, ($C_3$-$C_7$cycloalkyl) $C_0$-$C_2$alkoxy, ($C_1$-$C_6$alkyl$SO_2$) $C_0$-$C_2$alkyl, $C_1$-$C_6$alkylNHCO—, and ($C_1$-$C_6$alkyl)$_2$NCO—; and Q is absent or is —$CH_2$—, or —$CH_2CH_2$—.

2. The compound or salt of claim 1, or a pharmaceutically acceptable salt thereof, wherein:

$R^1$ and $R^2$ are independently chosen from $C_1$-$C_6$alkyl, and —$CO_2$—$C_1$-$C_6$alkyl;

$R^3$ and $R^4$ are independently chosen from hydrogen, fluoro, and methyl;

$X^1$, $X^2$, $X^3$, $X^4$, and $X^5$ are aromatic ring atoms chosen from N and C, where up to 3 of $X^1$, $X^2$, $X^3$, $X^4$, and $X^5$ are N ring atoms and each C ring atom is optionally substituted with $R^6$ where each $R^6$ is independently chosen from halogen, hydroxyl, cyano, amino, —$CONH_2$, $C_1$-$C_6$alkyl, $C_1$-$C_6$-alkoxy, $C_1$-$C_2$haloalkyl, $C_1$-$C_2$haloalkoxy, $C_3$-$C_7$-cycloalkyl, and $C_3$-$C_7$-cycloalkyl-O—.

3. The compound or salt of claim 1, wherein $R^1$ is —$CO_2$—$C_1$-$C_6$alkyl or $C_1$-$C_6$alkyl and $R^2$ is $C_1$-$C_6$alkyl;

$R^3$ and $R^4$ are hydrogen or methyl;

$A^1$ is a pyrimidyl or pyrazinyl heteroarylene, group, each of which is optionally substituted with one or more substituents independently chosen from halogen, hydroxyl, cyano, $C_1$-$C_2$alkyl, $C_1$-$C_2$alkoxy, trifluoromethyl, and trifluoromethoxy;

$X^1$, $X^2$, $X^3$, $X^4$, and $X^5$ are aromatic ring atoms chosen from N and C, where 0 or 1 of $X^1$, $X^2$, $X^3$, $X^4$, and $X^5$ are N ring atoms and each C ring atom is optionally substituted with $R^6$ where each Re is independently chosen from fluoro, chloro, hydroxyl, cyano, —$CONH_2$, $C_1$-$C_2$alkyl, $C_1$-$C_2$alkoxy, trifluoromethyl, trifluoromethoxy, $C_1$-$C_2$alkyl$SO_2$—, $C_1$-$C_2$alkylNHCO—, and $(C_1$-$C_2$alkyl$)_2$NCO—; and Q is —$CH_2$—.

4. The compound or salt of claim 1 of the Formula 1B, or 1C;

(1B)

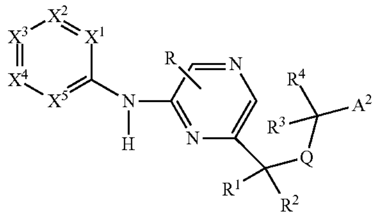

(1C)

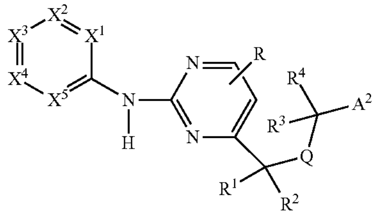

where R is absent or is one or more substituents independently chosen from halogen, cyano, and $C_1$-$C_2$alkyl, or $C_1$-$C_2$alkoxy.

5. The compound or salt of claim 4, where the $X^1$-$X^5$ containing ring is a phenyl or pyridyl and is optionally substituted with 1, 2, or 3 substituents independently chosen from fluoro, chloro, bromo, hydroxyl, cyano, $CH_3SO_2$-$C_1$-$C_3$alkyl, $C_1$-$C_3$alkoxy, trifluormethyl, and trifluromethoxy.

6. The compound or salt of claim 4, where the $X^1$-$X^5$ containing ring is a phenyl or 2-pyridyl and is optionally substituted with 1, 2, or 3 substituents independently chosen from fluoro, chloro, hydroxyl, methyl, methoxy, and $CH_3SO_2$—.

7. The compound or salt of claim 5, where $R^1$ is ethyl, —$CO_2$-ethyl, or —$CO_2$-t-butyl; and $R^2$ is ethyl.

8. The compound or salt of claim 5, where Q is —$CH_2$— and $R^3$ and $R^4$ are both hydrogen.

9. The compound of claim 1, or a pharmaceutically acceptable salt thereof 4-ethoxycarbonyl-4-[6-(4-methylanilino)pyrazin-2-yl]hexanoic acid;

4-[6-(2,4-difluoroanilino)pyrazin-2-yl]-4-ethoxycarbonyl-hexanoic acid;

(4R)-4-[6-(2,4-difluoroanilino)pyrazin-2-yl]-4-ethoxy-carbonyl-hexanoic acid;

(4S)-4-[6-(2,4-difluoroanilino)pyrazin-2-yl]-4-ethoxycarbonyl-hexanoic acid;

4-ethoxycarbonyl-4-[2-(4-methylanilino)pyrimidin-4-yl]hexanoic acid;

4-tert-butoxycarbonyl-4-[6-(4-methylanilino)pyrazin-2-yl]hexanoic acid;

4-ethoxycarbonyl-4-[6-(2-methoxyanilino)pyrazin-2-yl]hexanoic acid;

4-[6-(2,4-difluoroanilino)pyrazin-2-yl]-4-ethyl-hexanoic acid;

4-[6-(2,4-difluoroanilino)-3-ethyl-pyrazin-2-yl]-4-ethyl-hexanoic acid;

4-[6-(2,5-difluoroanilino)pyrazin-2-yl]-4-ethoxycarbonyl-hexanoic acid;

4-[6-[(3,5-difluoro-2-pyridyl)amino]pyrazin-2-yl]-4-ethyl-hexanoic acid;

4-[6-(2-chloroanilino)pyrazin-2-yl]-4-ethyl-hexanoic acid;

4-ethyl-4-[6-(2,4,5-trifluoroanilino)pyrazin-2-yl]hexanoic acid;

4-(isobutoxycarbonyl)-4-(6-(p-tolylamino)pyrazin-2-yl)hexanoic acid;

4-(cyclopropylmethyl)-5-ethoxy-5-oxo-4-(6-(p-tolylamino)pyrazin-2-yl)pentanoic acid;

4-(ethoxycarbonyl)-4-(6-((3-fluoro-4-hydroxyphenyl)amino)pyrazin-2-yl) hexanoic acid;

4-(6-((2,4-difluorophenyl)amino)pyrazin-2-yl)-4-(methoxymethyl)hexanoic acid; or 4-(6-((2,4-difluorophenyl)amino)pyrazin-2-yl)-4-((1-methylcyclopropoxy)carbonyl)hexanoic acid.

10. A pharmaceutical composition comprising a compound of claim 4 and a pharmaceutically acceptable carrier.

11. A method of treating obesity, pulmonary arterial hypertension, or non-alcoholic steatohepatitis (NASH) in a subject, comprising administering a therapeutically effective amount of a compound of salt of claim 4 to the subject.

12. A method of preventing or delaying the onset of pulmonary arterial hypertension in a subject at risk for pulmonary arterial hypertension comprising administering an effective amount of a compound or salt claim 4 to the subject.

13. A method of treating pain or inflammation in a subject, comprising administering a therapeutically effective amount of a compound of salt of claim 4 to the subject.

14. A method of treating or preventing cisplatin nephrotoxicity in a patient, comprising administering a therapeutically effective amount of a compound or salt of claim 4 to the patient prior to cisplatin administration, concurrently with cisplatin administration, or following cisplatin administration.

15. A method of treating ARDS or hyperinflammation associated with SARS-CoV-2 infection in a subject comprising administering an effective amount of a compound or salt of claim 4 in a subject.

* * * * *